US007064244B2

(12) United States Patent
Jakobovits et al.

(10) Patent No.: US 7,064,244 B2
(45) Date of Patent: Jun. 20, 2006

(54) TRANSGENIC MAMMALS HAVING HUMAN IG LOCI INCLUDING PLURAL $V_H$ AND $V_K$ REGIONS AND ANTIBODIES PRODUCED THEREFROM

(75) Inventors: Aya Jakobovits, Menlo Park, CA (US); Raju Kucherlapati, Darien, CT (US); Susan Klapholz, Stanford, CA (US); Michael J Mendez, El Granada, CA (US); Larry Green, San Francisco, CA (US)

(73) Assignee: Abgenix, Inc., Fremont, CA (US)

( * ) Notice: Subject to any disclaimer, the term of this patent is extended or adjusted under 35 U.S.C. 154(b) by 315 days.

(21) Appl. No.: 10/078,958

(22) Filed: Feb. 19, 2002
(Under 37 CFR 1.47)

(65) Prior Publication Data

US 2003/0070185 A1   Apr. 10, 2003

Related U.S. Application Data

(63) Continuation of application No. 08/759,620, filed on Dec. 3, 1996, now abandoned.

(51) Int. Cl.
A01K 67/027 (2006.01)
A01K 67/033 (2006.01)
C12P 21/00 (2006.01)
(52) U.S. Cl. .............................. 800/18; 800/13; 800/6
(58) Field of Classification Search ................ 800/13, 800/18
See application file for complete search history.

(56) References Cited

U.S. PATENT DOCUMENTS

| 5,545,806 | A | * | 8/1996 | Lonberg et al. .............. 800/6 |
| 5,545,807 | A | | 8/1996 | Surani et al. ................ 800/13 |
| 5,569,825 | A | | 10/1996 | Lonberg et al. .............. 800/13 |
| 6,150,584 | A | * | 11/2000 | Kucherlapati et al. ........ 800/18 |

FOREIGN PATENT DOCUMENTS

| EP | 0 463 151 B1 | 2/1992 |
| WO | WO 91/00906 | 1/1991 |
| WO | WO 92/03918 | 3/1992 |
| WO | WO 92/22645 | 12/1992 |
| WO | WO 93/12227 | 6/1993 |
| WO | WO 94/02602 | 2/1994 |
| WO | WO 94/25585 | 11/1994 |
| WO | WO 96/34096 | 10/1996 |

OTHER PUBLICATIONS

Green et al. (1994) Nat. Genet., vol. 7, pp. 13-21.*
Matsuda et al. (1993) Nat. Genet., vol. 3, pp. 88-94.*
Campbell (1997) Theriogenology, vol. 47 (1), pp. 63-72.*
Bruggemann, et al., "Stategies for expressing human antibody repertoires in transgenic mice," *Immunology Today*, 17:391-397 (1996).
Bruggemann, et al., "Human antibody production in transgenic mice: expression from 100kb of the human IgH locus," *Eur. J. Immunol.*, 21:1323-1326 (1991).
Cai, et al., "Extensive and selective mutation of a rearranged $V_H 5$ gene in human B cell chronic lymphocytic leukemia," J. Exp. Med., 176:1073-1081 (1992).
Campbell, et al., "Totipotency or Multipotentiality of Cultured Cells: Applications and Progress," *Theriogenology*, 47:63-72 (1997).
Chen, et al., "Immunoglobulin gene rearrangement in B-cell deficient mice generated by targeted deletion of the $J_H$ locus," *International Immunology*, 5: 647-656 (1993).
Choi, et al., "Transgenic mice containing a human heavy chain immunoglobulin gene fragment cloned in a yeast artificial chromosome," *Nature Genetics*, 4:117-123 (1993).
Cook, G.P. and Tomlinson, I.M., "The human immunoglobulin $V_H$ repertoire," *Immunology Today*, 16:237-242 (1995).
Corvalon, et al., "Generation of fully human high affinity monoclonal antibodies to EGF receptor in mice," *Journal of Allergy and Clinical Immunology* 99:S214 (1997).
Cox, et al., "A directory of human germ-line $V_x$ segments reveals a strong bias in their usage," *Eur. J. Immunol.*, 24:827-836 (1994).
Ellison, et al., Nucleic Acids Research, 10:4071-4079 (1982).
Fishwild, et al., "High-avidity human IgGk monoclonal antibodies from a novel strain of minilocus transgenic mice," *Nature Biotech.*, 14:845-851 (1996).
Green, et al., "Antigen-specific human monoclonal antibodies from mice engineered with human Ig heavy and light chain YACs," *Nature Genetics*, 7:13-21 (1994).
Huber, et al., "The human immunoglobulin κ locus. Characterization of the partially duplicated L regions," *Eur. J. Immunol.* 23:2860-2967 (1993).
Inaki, S., "Multiple mechanisms particpate 1 the generation of divertiy of human H chain CDR3 regions," the Journal of Immunology, 147:1720-1729 (1991).
Jakobovits, et al., "Human immunity in mice engineered with megabase human heavy and kappa light chain YACs," *Journal of Allergy and Clinical Immunology*, 99:S113 (1997).

(Continued)

*Primary Examiner*—Anne M. Wehbe'
(74) *Attorney, Agent, or Firm*—Fish & Neave IP Group Ropes & Gray LLP; Jane Gunnison; R. Minako Pazdera

(57) ABSTRACT

The present invention relates to transgenic non-human animals that are engineered to contain human immunoglobulin gene loci. In particular, animals in accordance with the invention possess human Ig loci that include plural variable ($V_H$ and Vκ) gene regions. Advantageously, the inclusion of plural variable region genes enhances the specificity and diversity of human antibodies produced by the animal. Further, the inclusion of such regions enhances and reconstitutes B-cell development to the animals, such that the animals possess abundant mature B-cells secreting extremely high affinity antibodies.

6 Claims, 53 Drawing Sheets

OTHER PUBLICATIONS

Jakobovits, et al. "Production of antigen-specific human antibodies from mice engineered with human heavy and light chain YACs," *Annals of the New York Academy of Sciences*, 764:525-535 (1995).

Jakobovits, A., "Production of fully human antibodies by transgenic mice," *Current Opinion in Biotechnology*, 6:561-566 (1995).

Jakobovits, "Humanizing the mouse genome," *Current Biology*, 4:761-763 (1994).

Jakobovits, et al., "Germ-line transmission and expression of a human-derived yeast artificial-chromosome," *Nature*, 362:255-258 (1993).

Jakobovits, et al., "Analysis of homozygous mutant chimeric mice: Deletion of the immunoglobulin heavy-chain joining region blocks B-cell development and antibody production," *Proc. Natl. Acad. Sci. USA*, 90:2551-2555 (1993).

Lonberg, et al., "Antigen-specific human antibodies from mice comprising four distinct genetic modifications," *Nature*, 368:856-859 (1994).

Matsuda, et al., "Structure and physical map of 64 variable segments in the 3' 0.8-megabase region of the human immunoglobulin heavy-chain locus," *Nature Genetics*, 3:88-94 (1993).

Mendez, et al., "Analysis of the structural integrity of PACs comprising human immunoglobulin gen s in yeast and in embryonic stem cells," *Genomics*, 26:294-307 (1995).

Mendez, et al., "Functional transport of megabase human immunoglobulin loci recapitulates human antibody response in mice," *Nature Genetics*, 15:146-156 (1997).

Takahashi, et al., "Structure of Human Immunoglobulin Gamma Genes: Implications for Evolution of a Gene Family," *Cell*, 29:671-679 (1982).

Taylor, et al., "Human immunoglobulin transgenes undergo rearrangement, somatic mutation and class switching in mice that lack endogenous IgM," *International Immunology*, 6:579-591 (1994).

Taylor, et al., "A transgenic mouse that expresses a diversity of human sequence heavy and light chain immunoglobulins," *Nucleic Acids Research*, 20:6287-6295 (1992).

Tuaillon, et al., "Analysis of direct and inverted $DJ_H$ rearrangements in a human Ig heavy chain transgenic minilocus," *J. Immunol.*, 154:6453-6465 (1995).

Tuaillon, et al., "Human immunoglobulin heavy-chain minilocus recombination in transgenic mice: gene-segment use in μ and γ transcripts," *Proc. Natl. Acad. Sci. USA*, 90:3720-3724 (1993).

Wagner, et al., "The diversity of antigen-specific monoclonal antibodies from transgenic mice bearing human immunoglobulin gene miniloci," *Eur. J. Immunol.* 24:2672-2681 (1994).

Weichhold, et al., "The human immunoglobulin κ locus consists of two copies that are organized in opposite polarity," *Genomics*, 16:503-511 (1993).

Yamada, M., et al., "Preferential utilization of specific immunoglobulin heavy chain diversity and joining segments in adult human peripheral blood B lymphocytes," *J. Exp. Med.*, 173:395-407 (1991).

Yang, et al., "Human monoclonal antibodies to human TNF-alpha generated from mice carrying human Ig loci," *Journal of Allergy and Clinical Immunology*, 99:S15 (1997).

\* cited by examiner

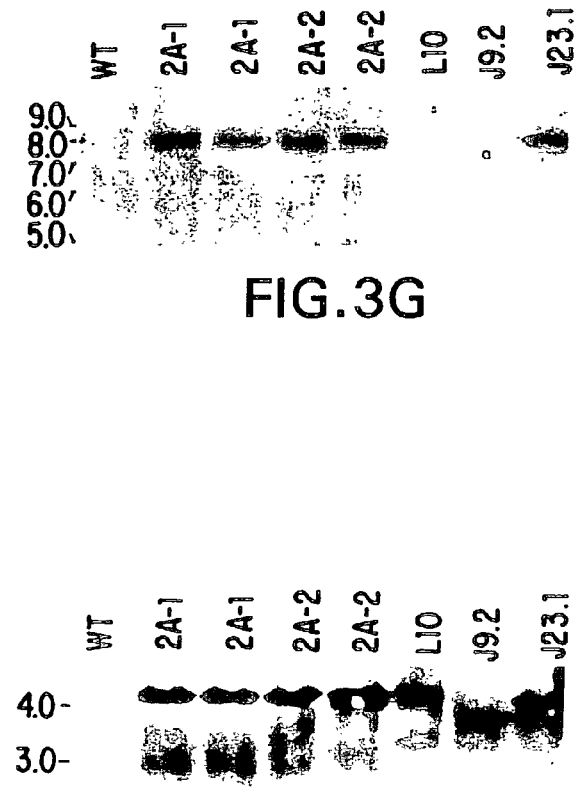
FIG.3G
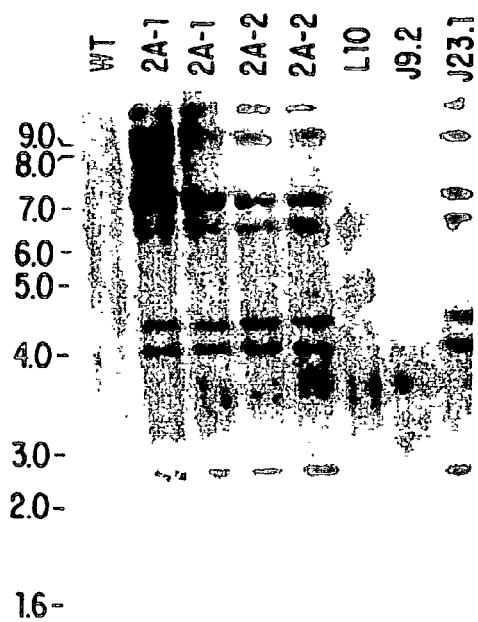
FIG.3F
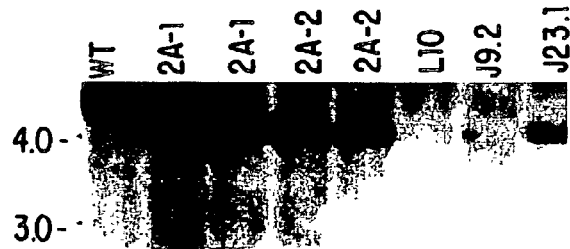
FIG.3H
FIG.3I

FIG. 6A

```
Human γ2
VH(DH/JH)
                      ┌──CDR1──┐                    ┌─────────CDR2─────────┐
 4-34      LSLTCAVYGGSFSGYYWSWIRQPPGKGLEWIGEINHSGSTNYNPSLKSRVTISVDTSKNQFSLKLSSVTAADTAVYYCAR
    D1.1   ----------------------------------------Q------------------------------T-------
(D21-10rc/JH3)
    K2.2   ---------------------------T------------I-H-N--------------S------------T-------
 (DK1/JH4)
                   ┌──CDR1──┐                      ┌────────CDR2────────┐
 5-51      SLKISCKGSGYSFTSYWIGWVRQMPGKGLEWMGIIYPGDSDTRYSPSFQGQVTISADKSISTAYLQWSSLKASDTAMYYC
    K4.3   ----------------------------------------------------------------------E---------
(DA1/A4/JH4)
                   ┌──DR1──┐                        ┌────────CDR2────────┐
 3-30      RSLRLSCAASGFTFSSYGMHWXRQAPGKGLEWVAVISYDGSNKYYADSVKGRFTISRDNSKNTLYLQMNSLRAEDTAVYY
    K4.2   ----------------------------------------E-------------------------V-------L-----
(Dir3rc/JH4)

ASTKGPSVFPLAPCSRSTST
                                    -------------------
                                    -------------------

┌─CDR3─┐
           ETPH AFDI  WGQGTMVTVSS
           GGAVAAFDY  WGQGTLVTVSS
              ┌─CDR3─┐
           AR — QDGDSFDY  WGQGTLVTVSS
              ┌─CDR3─┐
          CAR —— DRLGIFDY  WGQGTLVTVSS
```

```
HUMAN C κ                                                                                                                    RTVAAPSVFIFPPSDEQ
Vk(Jk)
              ┌─────CDR1──────┐                        ┌──CDR2──┐                                  ┌─CDR3─┐
O8      TITCQASQDISNYLNWYQQKPGKAPKLLIYDASNLETGVPSRFSGSGSGTDFTFTISSLQPEDIATYYCQQDNLP
D1.1    ----KF-S-F-----------------------------GT-Y------S--------------L------V-F---D-YTFGPGTKVDIK------
(Jκ3)
K4.2    -------------------A---------------------A---V--A----------------------------H-------LTFGGGTKVEIK------
(Jκ4)
              ┌─────CDR1──────┐                        ┌──CDR2──┐                                  ┌─CDR3─┐
O2      TCRASQSISSYLNWYQQKPGKAPKLLIYAASSLQSGVPSRFSGSGSGTDFTLTISSLQPEDFATYYCQQSYSTP
K4.3    ------N----------------------------------F--G-----E---------------------------N------LTFGGGTXVEIK------
(Jκ4)
              ┌───CDR1────┐                           ┌──CDR2──┐                                   ┌─CDR3─┐
B3      TINCKSSQSVLYSSNNKNYLAWYQQKPGQPPKKLLIYWASTRESGVPDRFSGSGSGTDFTLTISSLQAEDVAVYYCQQYYSTP
K2.2    ----I---------------------------------S------------K------------------------D---FTFGPGTKVDIK------
(Jκ3)
```

Kde $V_\kappa$ II $V_\kappa$ III

Cκ

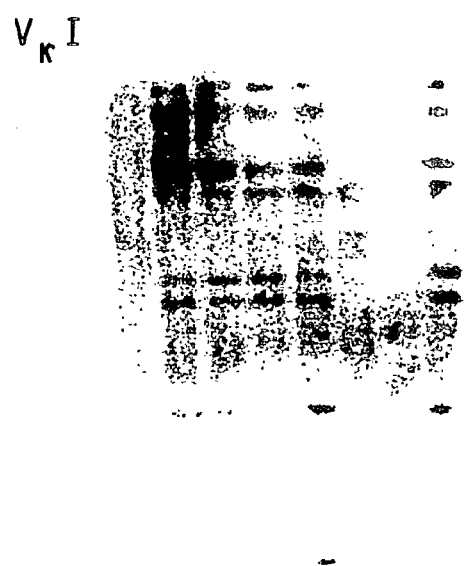
FIG.12F
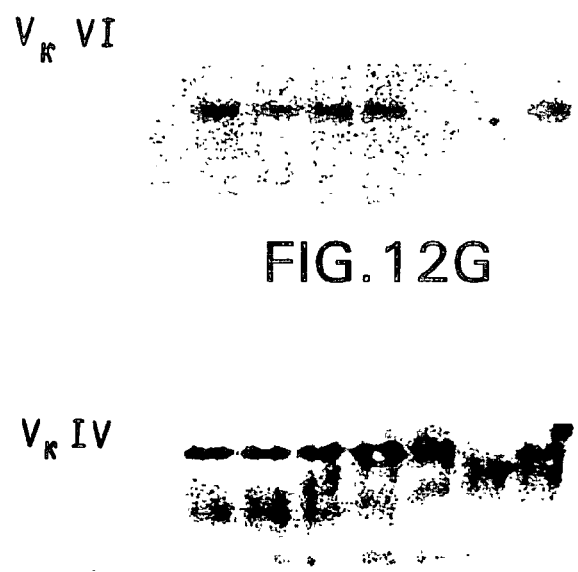
FIG.12G
FIG.12H
FIG.12I

| XENOMOUSE* (HUMAN Ig μg/μl) | WILD TYPE MOUSE (B6x129)* (MOUSE Ig μg/μl) |
|---|---|
| μ   700 | 400 |
| γ   600 (hγ2) | 2000 (ALL γ ISOTYPES) |
| κ   800 | 2000 |

\* KEPT IN PATHOGEN-FREE CONDITIONS

FIG. 14

| CLONE | V_H | | N | D_H | | N | J_H | |
|---|---|---|---|---|---|---|---|---|
| A2.2.1 | 5-51 (DP73) | TTACTGTGCGAGACA | 4 (TAGG) | XP5rc | AATCAT | 12 (GGGAGCTACGGG) | JH4 | GACTACTGGGGC |
| B2.1.5 | 3-33 (DP-50) | TTACTGTGCGAGAGA | 7 (TCGGGGA) | 3rc | AATAGCA | 7 (CTGGCCT) | JH4 | CTTTGACTACTGGGGC |
| B4.2.4 | 3-15 (DP-38) | TTACTGTACCACAGA | 1 (G) | K1 | GCCTAC | 11 (ACTAACTACCC) | JH6 | CTACTACTACTACGGT |
| B4.2.5 | 4-59 (DP-71) | TTACTGTGCGAGAGA | 10 (TAGGAGTGTT) | 4 | GTAGTACCAGCTGCTAT | 6 (ACCCAA) | JH6 | ACTACTACTACTACGGT |
| D2.2.5 | 4-34 (DP-63) | TTACTGTGCGAGAG_ | 2 (GG) | N1 | GCAGCAGCTG | 4 (CCCT) | JH4 | CTTTGACTACTGGGGC |
| D2.1.3 | 3-48 (DP51) | TTACTGTGCGAGAGA | 4 (TCTT) | XP1 | GATATTTTGACTGGT | 2 (CT) | JH6 | CTACTACTACGGT |
| D2.2.8 | 4-31 (DP-65) | TTACTGTGCGAGACA | 2 (GA) | A4 | GACTGCAG | 5 (CCGTT) | JH4 | TTTGACTACTGGGGC |
| A2.2.4 | 3-21 (DP-77) | TTACTGTGCGAGAGA | 2 (TT) | IR3 | GGGGCTGG | 3 (ACC) | JH6 | TACTACTACTACTACGGT |
| D4.2.11 | 4-4/4.35 | ATTACTGTGCGA | 1 (A) | N1 | TATAGCAGTGGCTGGT | 2 (GT) | JH4 | CTTTGACTACTGGGGC |
| C1.2.1 | 1-18/(DP-14) | TATTACTGTGCGGAG_ | 0 | XP'1/21-7 | GTTA | 0 | JH4 | GACTACTGGGGC |
| C3.1.2 | 4-39/(DP-79) | TATTACTGTGCG | 3 (GCC) | 2 | GGATATAGTAGTGG | 6 (TCGGGC) | JH4 | CTTTGACTACTGGGGC |
| D2.2.7 | 5-51 (DP73) | TTACTGTGCGAGACA | 4 (TGGC) | K1 | AGTGGCT | 9 (GGTACTCTG) | JH3 | ATGCTTTTGATATCTGGGG |

FIG. 15

| CLONE | V<sub>K</sub> | | N | J<sub>K</sub> | |
|---|---|---|---|---|---|
| F2.2.3 | O2/(DPK9) | TTAAACGAACAGTACCCC | 0 | JK5 | GATCACCTTCGGCCAA |
| F4.1.8 | L5/(DPK5) | ACAGGCTAACAGTTTCCCTC | 0 | JK1 | GGACGTTCGGCCAA |
| F4.1.6 | A20/(DPK4) | AAGTATAACAGTGCCCC | 0 | JK3 | ATTCACTTTCGGCCCT |
| F2.2.5 | O8 | ACAGTATGATAATCTCCC | 0 | JK4 | GCTCACTTTCGGCGGA |
| F2.1.5 | L1 | AAAGTATAATAGTTACCC | 0 | JK5 | GATCACCTTCGGCCAA |
| F2.1.4 | A30 | CAGCATAATAGTTACCC | 0 | JK3 | ATTCACTTTCGGCCCT |
| F2.1.3 | B3/(DPK24) | AATATTATAGTACTCC | 0 | JK4 | GCTCACTTTCGGCCGA |
| F4.1.3 | A27/DPK22 | CAGTATGGTAGCTCACCTC | 1(G) | JK2 | CACTTTGGCCAG |

FIG. 16

TITER

| ANTIGEN | hIgM | hIgG | hIgκ |
|---|---|---|---|
| HUMAN IL-8 | $7 \times 10^5$ | $1 \times 10^6$ | $4 \times 10^6$ |
| HUMAN EGFR | $4 \times 10^5$ | $7.5 \times 10^5$ | $3 \times 10^6$ |
| HUMAN TNFα | $4 \times 10^5$ | $4 \times 10^5$ | $3 \times 10^5$ |

FIG. 18

| ANTIBODY | VH | D | JH | Vκ | Jκ |
|---|---|---|---|---|---|
| D1.1 | 4-34 | 21-10rc | JH3 | O18 | Jκ3 |
| K2.2 | 4-21 | ir3rc | JH4 | B3 | Jκ3 |
| K4.2 | 3-30 | K1 | JH4 | O18 | Jκ4 |
| K4.3 | 5-51 | M5-a/M5-b | JH4 | O12 | Jκ4 |

FIG. 19

```
                                                                                    ASTKGPSVFPLAPCSRSTST
HUMAN γ2                          CDR1                            CDR2                                              CDR3
VH(DH/JH)       LSLTCAVYGGSFSGYYWSWIRQPPGKGLEWIGEINHSGSTNYNPSLKSRVTISVDTSKNQFSLKLSSVTAADTAVYYCAR
4-34/4-21
D1.1            ----------------------Q-------------------T-----I-------T-----------------------        ETPH AFDI WGQGTMVTVSS
(D21-10rc/JH 3)
                                                                        -I-H-N------S--------T--------            GGAVAAFDY WGQGTLVTVSS
K4.2                                CDR1                                CDR2                                       CDR3
(DK1-JH 4)      SLKISCKGSGYSFTSYWIGWVRQMPGKGLEWMGIIYPGDSDTRYSPSFQGQVTISADKSISTAYLQWSSLKASDTAMYYCAR
5-51                                                                                                               QDCDSFDY WGQGTLVTVSS
K4.3                                CDR1                                 CDR2                                      CDR3
(A1/A4/JH 4)    RSLRLSCAASGFTFSSYGMHWXRQAPGKGLEWVAVISYDGSNKYYADSVKGRFTISRDNSKNTLYLQMNSLRAEDTAVYYCAR
3-30
K2.2            -----------------------------E-----V--L----------------------------------------         DRLGIFDY WGQGTLVTVSS
(Dir3rc/JH 4)
```

FIG. 20

```
HUMAN Cκ                                                                                                    RTVAAPSVF IFPPSDEQ

Vκ(Jκ)          CDR1                              CDR2                                       CDR3
   O8    TITCQASQDISNYLNWYQQKPGKAPKLLIYDASNLETGVPSRFSGSGSGTDFTFTISSLQPEDIATYYCQQDNLP

D1.1     --------KF-S-F-------------------GT-Y------------------------------------V---F----D--YTFGPGTKVDIK--------
(Jκ3)

K4.2     ------------------------------------------A----V---A-----------------------------H----LTFGGGTKVEIK--------
(Jκ4)

CDR1                              CDR2                                       CDR3
   O2    TCRASQSISSYLNWYQQKPGKAPKLLIYAASSLQSGVPSRFSGSGSGTDFTLTISSLQPEDFATYYCQQSYSTP

K4.3     --------------N-------------------F--G--E---------------------------------------N---LTFGGGTXVEIK--------
(Jκ4)

CDR1                              CDR2                                       CDR3
   B3    TINCKSSQSVLYSSNNKNYLAWYQQKPGQPPKLLIYWASTRESGVPDRFSGSGSGTDFTLTISSLQAEDVAVYYCQQYYSTP

K2.2     --------------I-------------------S----------K-----------------------------------D--FTFGPGTKVDIK--------
(Jκ3)
```

FIG. 21

| IMPLANT | ANGIOGENESIS (# CORNEAS) | |
|---|---|---|
| | POSITIVE | NEGATIVE |
| IL-8 ALONE | 15 | 1 |
| IL-8 + CONTROL MAb | 4 | 1 |
| IL-8 + D1.1 | 0 | 6 |
| IL-8 + K2.2 | 1 | 5 |
| IL-8 + K4.3 | 2 | 4 |

FIG. 28

| ANTIBODY | VH | D | JH | Vκ | Jκ |
|---|---|---|---|---|---|
| E1.1 | 4-31 | 2 | JH5 | 018 | Jκ4 |
| E2.4 | 4-31 | A1/A4 | JH3 | 018 | Jκ4 |
| E2.5 | 4-31 | XP1/21-10 | JH4 | 018 | Jκ4 |
| E2.11 | 4-61 | XP1/21-10 | JH4 | 018 | Jκ2 |

FIG. 29

TRANSGENIC MAMMALS HAVING HUMAN IG LOCI INCLUDING PLURAL $V_H$ AND $V_K$ REGIONS AND ANTIBODIES PRODUCED THEREFROM

This application is a continuation of U.S. application Ser. No. 08/759,620, filed Dec. 3, 1996 now abandoned, the disclosure of which is incorporated herein by its entirety.

BACKGROUND OF THE INVENTION

1. Field of the Invention

The present invention relates to transgenic non-human animals that are engineered to contain human immunoglobulin gene loci. In particular, animals in accordance with the invention possess human Ig loci that include plural variable ($V_H$ and Vκ) gene regions. Advantageously, the inclusion of plural variable region genes enhances the specificity and diversity of human antibodies produced by the animal. Further, the inclusion of such regions enhances and reconstitutes B-cell development to the animals, such that the animals possess abundant mature B-cells secreting extremely high affinity antibodies.

2. Background of the Technology

The ability to clone and reconstruct megabase-sized human loci in YACs and to introduce them into the mouse germline provides a powerful approach to elucidating the functional components of very large or crudely mapped loci as well as generating useful models of human disease. Furthermore, the utilization of such technology for substitution of mouse loci with their human equivalents could provide unique insights into the expression and regulation of human gene products during development, their communication with other systems, and their involvement in disease induction and progression.

An important practical application of such a strategy is the "humanization" of the mouse humoral immune system. Introduction of human immunoglobulin (Ig) loci into mice in which the endogenous Ig genes have been inactivated offers the opportunity to study of the mechanisms underlying programmed expression and assembly of antibodies as well as their role in B-cell development. Furthermore, such a strategy could provide an ideal source for production of fully human monoclonal antibodies (Mabs)—an important milestone towards fulfilling the promise of antibody therapy in human disease. Fully human antibodies are expected to minimize the immunogenic and allergic responses intrinsic to mouse or mouse-derivatized Mabs and thus to increase the efficacy and safety of the administered antibodies. The use of fully human antibodies can be expected to provide a substantial advantage in the treatment of chronic and recurring human diseases, such as inflammation, autoimmunity, and cancer, which require repeated antibody administrations.

One approach towards this goal was to engineer mouse strains deficient in mouse antibody production with large fragments of the human Ig loci in anticipation that such mice would produce a large repertoire of human antibodies in the absence of mouse antibodies. Large human Ig fragments would preserve the large variable gene diversity as well as the proper regulation of antibody production and expression. By exploiting the mouse machinery for antibody diversification and selection and the lack of immunological tolerance to human proteins, the reproduced human antibody repertoire in these mouse strains should yield high affinity antibodies against any antigen of interest, including human antigens. Using the hybridoma technology, antigen-specific human Mabs with the desired specificity could be readily produced and selected.

This general strategy was demonstrated in connection with our generation of the first XenoMouse™ strains as published in 1994. See Green et al. *Nature Genetics* 7:13–21 (1994). The XenoMouse™ strains were engineered with 245 kb and 190 kb-sized germline configuration fragments of the human heavy chain loci and kappa light chain loci, respectively, which contained core variable and constant region sequences. Id. The human Ig containing yeast artificial chromosomes (YACs) proved to be compatible with the mouse system for both rearrangement and expression of antibodies, and were capable of substituting for the inactivated mouse Ig genes. This was demonstrated by their ability to induce B-cell development and to produce an adult-like human repertoire of fully human antibodies and to generate antigen-specific human Mabs. These results also suggested that introduction of larger portions of the human Ig loci containing greater numbers of V genes, additional regulatory elements, and human Ig constant regions might recapitulate substantially the full repertoire that is characteristic of the human humoral response to infection and immunization.

Such approach is further discussed and delineated in U.S. patent application Ser. No. 07/466,008, filed Jan. 12, 1990, Ser. No. 07/610,515, filed Nov. 8, 1990, Ser. No. 07/919,297, filed Jul. 24, 1992, Ser. No. 07/922,649, filed Jul. 30, 1992, Ser. No. 08/031,801, filed Mar. 15, 1993, Ser. No. 08/112,848, filed Aug. 27, 1993, Ser. No. 08/234,145, filed Apr. 28, 1994, Ser. No. 08/376,279, filed Jan. 20, 1995, Ser. No. 08/430,938, Apr. 27, 1995, Ser. No. 08/464,584, filed Jun. 5, 1995, Ser. No. 08/464,582, filed Jun. 5, 1995, Ser. No. 08/463,191, filed Jun. 5, 1995, Ser. No. 08/462,837, filed Jun. 5, 1995, Ser. No. 08/486,853, filed Jun. 5, 1995, Ser. No. 08/486,857, filed Jun. 5, 1995, Ser. No. 08/486,859, filed Jun. 5, 1995, Ser. No. 08/462,513, filed Jun. 5, 1995, and 08/724,752, filed Oct. 2, 1996. See also European Patent No., EP 0 463 151 B1, grant published Jun. 12, 1996, International Patent Application No., WO 94/02602, published Feb. 3, 1994, International Patent Application No., WO 96/34096, published Oct. 31, 1996, and PCT Application No. PCT/US96/05928, filed Apr. 29, 1996. The disclosures of each of the above-cited patents and applications are hereby incorporated by reference in their entirety.

In an alternative approach, others, including GenPharm International, Inc., have utilized a "minilocus" approach. In the minilocus approach, an exogenous Ig locus is mimicked through the inclusion of pieces (individual genes) from the Ig locus. Thus, one or more $V_H$ genes, one or more $D_H$ genes, one or more $J_H$ genes, a mu constant region, and a second constant region (preferably a gamma constant region) are formed into a construct for insertion into an animal. This approach is described in U.S. Pat. No. 5,545,807 to Surani et al. and U.S. Pat. Nos. 5,545,806 and 5,625,825, both to Lonberg and Kay, and GenPharm International U.S. patent application Ser. No. 07/574,748, filed Aug. 29, 1990, Ser. No. 07/575,962, filed Aug. 31, 1990, Ser. No. 07/810,279, filed Dec. 17, 1991, Ser. No. 07/853,408, filed Mar. 18, 1992, Ser. No. 07/904,068, filed Jun. 23, 1992, Ser. No. 07/990,860, filed Dec. 16, 1992, Ser. No. 08/053,131, filed Apr. 26, 1993, Ser. No. 08/096,762, filed Jul. 22, 1993, Ser. No. 08/155,301, filed Nov. 18, 1993, Ser. No. 08/161,739, filed Dec. 3, 1993, Ser. No. 08/165,699, filed Dec. 10, 1993, Ser. No. 08/209,741, filed Mar. 9, 1994, the disclosures of which are hereby incorporated by reference. See also International Patent Application Nos. WO 94/25585, published Nov. 10, 1994, WO 93/12227, published Jun. 24, 1993, WO 92/22645, published Dec. 23, 1992, WO 92/03918, published Mar. 19, 1992, the disclosures of which are hereby incorporated by reference in their entirety. See further Taylor et al., 1992, Chen et al., 1993, Tuaillon et al., 1993, Choi et al., 1993, Lonberg et al., (1994), Taylor et al., (1994), and Tuaillon et al., (1995), the disclosures of which are hereby incorporated by reference in their entirety.

The inventors of Surani et al., cited above, and assigned to the Medical Research Counsel (the "MRC"), produced a transgenic mouse possessing an Ig locus through use of the minilocus approach. The inventors on the GenPharm International work, cited above, Lonberg and Kay, following the lead of the present inventors, proposed inactivation of the endogenous mouse Ig locus coupled with substantial duplication of the Surani et al. work.

An advantage of the minilocus approach is the rapidity with which constructs including portions of the Ig locus can be generated and introduced into animals. Commensurately, however, a significant disadvantage of the minilocus approach is that, in theory, insufficient diversity is introduced through the inclusion of small numbers of V, D, and J genes. Indeed, the published work appears to support this concern. B-cell development and antibody production of animals produced through use of the minilocus approach appear stunted. Therefore, the present inventors have consistently urged introduction of large portions of the Ig locus in order to achieve greater diversity and in an effort to reconstitute the immune repertoire of the animals.

Accordingly, it would be desirable to provide transgenic animals containing more complete germline sequences and configuration of the human Ig locus. It would be additionally desirable to provide such locus against a knockout background of endogenous Ig.

SUMMARY OF THE INVENTION

Provided in accordance with the present invention are transgenic animals having a near complete human Ig locus, including both a human heavy chain locus and a human kappa light chain locus. Preferably, the heavy chain locus includes greater than about 20%, more preferably greater than about 40%, more preferably greater than about 50%, and even more preferably greater than about 60% of the human heavy chain variable region. In connection with the human kappa light chain, preferably, the locus includes greater than about 20%, more preferably greater than about 40%, more preferably greater than about 50%, and even more preferably greater than about 60% of the human kappa light chain variable region. Such percentages preferably refer to percentages of functional variable region genes.

Further, preferably such animals include the entire $D_H$ region, the entire $J_H$ region, the human mu constant region, and can additionally be equipped with genes encoding other human constant regions for the generation of additional isotypes. Such isotypes can include genes encoding $\gamma_1$, $\gamma_2$, $\gamma_3$, $\alpha$, $\epsilon$, $\beta$, and other constant region encoding genes. Alternative constant regions can be included on the same transgene, i.e., downstream from the human mu constant region, or, alternatively, such other constant regions can be included on another chromosome. It will be appreciated that where such other constant regions are included on the same chromosome as the chromosome including the human mu constant region encoding transgene, cis-switching to the other isotype or isotypes can be accomplished. On the other hand, where such other constant region is included on a different chromosome from the chromosome containing the mu constant region encoding transgene, trans-switching to the other isotype or isotypes can be accomplished. Such arrangement allows tremendous flexibility in the design and construction of mice for the generation of antibodies to a wide array of antigens.

Preferably, such mice additionally do not produce functional endogenous immunoglobulins. This is accomplished in a preferred embodiment through the inactivation (or knocking out) of endogenous heavy and light chain loci. For example, in a preferred embodiment, the mouse heavy chain J-region and mouse kappa light chain J-region and $C_\kappa$-region are inactivated through utilization of homologous recombination vectors that replace or delete the region. Such techniques are described in detail in our earlier applications and publications.

Unexpectedly, transgenic mice in accordance with the invention appear to possess an almost entirely reconstituted immune system repertoire. This is dramatically demonstrated when four separate mouse strains are compared: a first strain contains extensive human heavy chain variable regions and human kappa light chain variable regions and encodes only a mu isotype, a second strain contains extensive human heavy chain variable regions and human kappa light chain variable regions and encodes a mu and gamma-2 isotypes, a third strain contains significantly less human heavy and kappa light chain variable regions, and a fourth strain contains a double-inactivated mouse Ig locus. The first and second strains undergo similar, if not identical, B-cell development, whereas the third strain has a reduced development and maturation of B-cells, and the fourth strain contains no mature B-cells. Further, it is interesting to note that production of human antibodies in preference to mouse antibodies is substantially elevated in mice having a knockout background of endogenous Ig. That is to say that mice that contain a human Ig locus and a functionally inactivated endogenous Ig produce human antibodies at a rate of approximately 100 to 1000 fold as efficiently as mice that contain only a human Ig locus.

Thus, in accordance with a first aspect of the present invention there is provided a transgenic non-human mammal having a genome, the genome comprising modifications, the modifications comprising: an inactivated endogenous immunoglobulin (Ig) locus, such that the mammal would not display normal B-cell development; an inserted human heavy chain Ig locus in substantially germline configuration, the human heavy chain Ig locus comprising a human mu constant region and regulatory and switch sequences thereto, a plurality of human $J_H$ genes, a plurality of human $D_H$ genes, and a plurality of human $V_H$ genes; and an inserted human kappa light chain Ig locus in substantially germline configuration, the human kappa light chain Ig locus comprising a human kappa constant region, a plurality of J$\kappa$ genes, and a plurality of V$\kappa$ genes, wherein the number of $V_H$ and V$\kappa$ genes inserted are selected to substantially restore normal B-cell development in the mammal. In a preferred embodiment, the heavy chain Ig locus comprises a second constant region selected from the group consisting of human gamma-1, human gamma-2, human gamma-3, human gamma-4, alpha, delta, and epsilon. In another preferred embodiment, the number of $V_H$ genes is greater than about 20. In another preferred embodiment, the number of V$\kappa$ genes is greater than about 15. In another preferred embodiment, the number of $D_H$ genes is greater than about 25, the number of $J_H$ genes is greater than about 4, the number of $V_H$ genes is greater than about 20, the number of J$\kappa$ genes is greater than about 4, and the number of V$\kappa$ genes is greater than about 15. In another preferred embodiment, the number of $D_H$ genes, the number of $J_H$ genes, the number of $V_H$ genes, the number of Jκ genes, and the number of Vκ genes are selected such that the Ig loci are capable of encoding greater than about $1\times10^5$ different functional antibody sequence combinations. In a preferred embodiment, in a population of mammals B-cell function is reconstituted on average to greater than about 50% as compared to wild type.

In accordance with a second aspect of the present invention there is provided an improved transgenic non-human mammal having a genome that comprises modifications, the modifications rendering the mammal capable of producing human immunoglobulin molecules but substantially incapable of producing functional endogenous immunoglobulin molecules, the improvement comprising: insertion into the genome of the mammal of sufficient human $V_H$, $D_H$, $J_H$, Vκ, and Jκ genes such that the mammal is capable encoding greater than about $1\times10^6$ different functional human immunoglobulin sequence combinations.

In accordance with a third aspect of the present invention, there is provided an improved transgenic non-human mammal having a genome that comprises modifications, the modifications rendering the mammal capable of producing human immunoglobulin molecules but substantially incapable of producing functional endogenous immunoglobulin molecules, which modifications, with respect to the mammal's incapacity to produce functional endogenous immunoglobulin molecules would not allow the mammal to display normal B-cell development, the improvement comprising: insertion into the genome of the mammal of sufficient human $V_H$, $D_H$, $J_H$, Vκ, and Jκ genes such that the mammal is capable of encoding greater than about $1\times10^6$ different functional human immunoglobulin sequence combinations and sufficient $V_H$ and Vκ genes to substantially restore normal B-cell development in the mammal. In a preferred embodiment, in a population of mammals B-cell function is reconstituted on average to greater than about 50% as compared to wild type.

In accordance with a fourth aspect of the present invention, there is provided a transgenic non-human mammal having a genome, the genome comprising modifications, the modifications comprising: an inactivated endogenous heavy chain immunoglubulin (Ig) locus; an inactivated endogenous kappa light chain Ig locus; an inserted human heavy chain Ig locus, the human heavy chain Ig locus comprising a nucleotide sequence substantially corresponding to the nucleotide sequence of yH2; and an inserted human kappa light chain Ig locus, the human kappa light chain Ig locus comprising a nucleotide sequence substantially corresponding to the nucleotide sequence of yK2.

In accordance with a fifth aspect of the present invention there is provided a transgenic non-human mammal having a genome, the genome comprising modifications, the modifications comprising: an inactivated endogenous heavy chain immunoglubulin (Ig) locus; an inserted human heavy chain Ig locus, the human heavy chain Ig locus comprising a nucleotide sequence substantially corresponding to the nucleotide sequence of yH2; and an inserted human kappa light chain Ig locus, the human kappa light chain Ig locus comprising a nucleotide sequence substantially corresponding to the nucleotide sequence of yK2.

In accordance with a sixth aspect of the present invention, there is provided a transgenic non-human mammal having a genome, the genome comprising modifications, the modifications comprising: an inactivated endogenous heavy chain immunoglubulin (Ig) locus; an inactivated endogenous kappa light chain Ig locus; an inserted human heavy chain Ig locus, the human heavy chain Ig locus comprising a nucleotide sequence substantially corresponding to the nucleotide sequence of yH2 without the presence of a human gamma-2 constant region; and an inserted human kappa light chain Ig locus, the human kappa light chain Ig locus comprising a nucleotide sequence substantially corresponding to the nucleotide sequence of yK2.

In accordance with a seventh aspect of the present invention, there is provided a transgenic non-human mammal having a genome, the genome comprising modifications, the modifications comprising: an inactivated endogenous heavy chain immunoglubulin (Ig) locus; an inserted human heavy chain Ig locus, the human heavy chain Ig locus comprising a nucleotide sequence substantially corresponding to the nucleotide sequence of yH2 without the presence of a human gamma-2 constant region; and an inserted human kappa light chain Ig locus, the human kappa light chain Ig locus comprising a nucleotide sequence substantially corresponding to the nucleotide sequence of yK2.

In accordance with an eighth aspect of the present invention, there is provided a method for the production of human antibodies, comprising: inoculating any of the mammals of the first through fifth aspects of the invention discussed above with an antigen; collecting and immortalizing lymphocytic cells to obtain an immortal cell population secreting human antibodies that specifically bind to the antigen with an affinity of greater than $10^9$ $M^{-1}$; and isolating the antibodies from the immortal cell populations.

In a preferred embodiment, the antigen is IL-8. In another preferred embodiment, the antigen is EGFR. In another preferred embodiment, the antigen is TNF-α.

In accordance with a ninth aspect of the present invention, there is provided an antibody produced by the method of the sixth aspect of the invention, including antibodies to IL-8, EGFR, and TNF-α.

In accordance with a tenth aspect of the present invention, there is provided an improved method for the production of transgenic mice, the transgenic mice having a genome, the genome comprising modifications, the modifications comprising insertion of a plurality of human variable regions, the improvement comprising: insertion of the human variable regions from a yeast artificial chromosome.

In accordance with an eleventh aspect of the present invention, there are provided transgenic mice and transgenic offspring therefrom produced through use of the improvement of the eighth aspect of the present invention.

In accordance with a twelfth aspect of the present invention, there is provided a transgenic mammal, the transgenic mammal comprising a genome, the genome comprising modifications, the modifications comprising an inserted human heavy chain immunoglobulin transgene, the improvement comprising: the transgene comprising selected sets of human variable region genes that enable human-like junctional diversity and human-like complementarity determining region 3 (CDR3) lengths. In a preferred embodiment, the human-like junctional diversity comprises average N-addition lengths of 7.7 bases. In another preferred embodiment, the human-like CDR3 lengths comprise between about 2 through about 25 residues with an average of about 14 residues.

BRIEF DESCRIPTION OF THE DRAWING FIGURES

FIGS. 1A–1B are a schematic representation of the reconstructed human heavy chain and human kappa light chain loci YACs introduced into preferred mice in accordance with the invention. YACs spanning the human heavy chain (1H, 2H, 3H, and 4H) and the human kappa light chain proximal (1K, 2K, and 3K) loci were cloned from human-YAC libraries. The locations of the different YACs with respect to the human Ig loci (adopted from Cook and Tomlinson, 1995, and Cox et al., 1994), their sizes, and non-Ig sequences are indicated (not shown to scale). The YACs were recombined into yeast in a two-step procedure (see Materials and Methods) to reconstruct the human heavy and kappa light chain YACS. yH2, the human heavy chain containing YAC, was further retrofitted with a human γgene sequence. yK2, was the human kappa light chain containing YAC. The YAC vector elements: telomere ▲, centromere ●, mammalian (HPRT, Neo) and yeast selectable markers (TRP1, ADE2, LYS2, LEU2, URA3, HIS3) on the YAC vector arms are indicated. $V_H$ segments are classified as genes with open reading frame ●, pseudogenes □, and unsequenced genes ○. $V_\kappa$ segments are classified as genes with open reading frames ●, and pseudogenes □. The V genes that we have found to be utilized by the XenoMouse II are marked (*). The VH gene region contained on yH2 is marked by arrows.

FIGS. 2A–2I show a series of Southern Blot analyses and characterizations of the human heavy chain YAC, yH2, integrated in ES cells and in XenoMouse strains. FIGS. 2A–2E show a series of Southern Blot analyses of EcoRI (FIGS. 2A, 2C) and BamHI (FIGS. 2B, 2D, 2E) digested DNA (2 μg) prepared from the CGM1 immortalized B-lymphoblast cell line derived from the Washington University YAC library source (Brownstein et al., 1989), yH2 YAC (0.5 μg YAC added to 2 μg of 3B1 DNA), unmodified E14TG.3B1 (3B1), and yH2-containing ES cell lines: L10, J9.2, L18, L17, and J17. The probes used for blotting were human $V_H 1$ (FIG. 2A), $D_H$ (FIG. 2B) [18 kb fragment in CGM1 lane represents D segments on chromosome 16], $V_H 3$ (FIG. 2C), Cμ (FIG. 2D) and $J_H$ (FIG. 2E). FIGS. 2F–2G show a series of Southern Blot analyses of EcoRI (FIGS. 2F, 2G) and BamHI (FIGS. 2H, 2I) digested DNA (10 μg) that was prepared from the tails of wildtype (WT, 129xB57BL/6J), XM2A-1, and XM2A-2 (2 individual offspring) mice or from the parental yH2-containing ES cell lines L10 (slightly underloaded relative to other samples), J9.2, and yK2-containing ES cell line J23.1. The probes used were human $V_H 1$ (FIG. 2F), $V_H 4$ (FIG. 2G), human γ-2) (FIG. 2H), and mouse 3'-enhancer (FIG. 2I, the 5 kb band represents the endogenous mouse 3'-enhancer fragment). Fragment sizes of molecular weight markers (in kb) are indicated.

FIGS. 3A–3I show a series of Southern Blot analyses characterizing the human kappa light chain YAC, yK2, integrated in ES cells and in XenoMouse 2A Strains. FIGS. 3A–E show a series of Southern Blot analyses of EcoRI (FIGS. 3A, 3C, 3D) and BamHI (FIGS. 3B, 3E) digested DNA (2 μg) prepared from CGM1 cell line (Brownstein et al., 1989, supra), yK2 YAC (0.5 μg YAC DNA added to 2 μg of 3B1 DNA), unmodified E14TG.3B1 (3B1), and yK2-containing ES cell lines: J23.1 and J23.7. The probes used were human Va (FIG. 3A), Kde (FIG. 3B), $V_\kappa II$ (FIG. 3C), $V_\kappa III$ (FIG. 3D), and $C_\kappa$ (FIG. 3E). FIG. 3F–3I show a series of Southern Blot analyses of EcoRI-digested DNA (2 μg) that was prepared from the tails of wildtype (WT, 129xB6), XM2A-1, and XM2A-2 (2 individual offspring) mice or from the parental yH2-containing ES cell lines L10 (slightly underloaded relative to other samples), J9.2, and yK2-containing ES cell line J23.1. The probes that were used were human $V_\kappa I$ (FIG. 3F), $V_\kappa IV$ (FIG. 3G), $V_\kappa VI$ (FIG. 3H) and 3'-enhancer (FIG. 3I). Fragment sizes of molecular weight markers (in kb) are indicated.

FIGS. 4A–4T shows B-cell reconstitution and surface expression of human μ, δ, and κ chains on XenoMouse-derived B-cells and shows flow cytometry analysis of peripheral blood (FIGS. 4A–4H) and spleen (FIGS. 4I–4T) lymphocytes from wildtype mice (WT), double inactivated mice (DI), and XenoMouse strains 2A-1 and 2A-2 (XM2A-1, XM2A-2). Four-color flow cytometry analysis was carried out using antibodies to the B-cell-specific marker B220 in combination with anti-human μ, δ, κ, or mouse μ, δ, κ, or λ. The percentage of positively-stained cells is shown in each quadrant. Isolation and staining of cells were performed as described in Materials and Methods. Populations of human $\kappa^+$ and mouse $\lambda^+$ cells were determined after first gating for $B220^+\mu^+$ populations in the indicated region. Populations of $\mu^+$ and $\delta^+$ cells were determined after first gating for $B220^+$ cells. The percentage of positive cells within a region or quadrant is indicated. The FACS profiles shown are representative of several experiments performed on each of the strains.

FIGS. 5A–5C show that XenoMouse-derived human antibodies block the binding of their specific antigens to cells. FIG. 5A shows the inhibition of labeled $[I^{125}]$IL-8 binding to human neutrophils by the mouse anti-human IL-8 antibody (R&D Systems) (□) and the fully human Mabs D1.1 (♦), K2.2 (●),K4.2 (▲), and K4.3 (▼). The background binding of labeled $[I^{125}]$IL-8 in the absence of antibody was 2657 cpm. FIG. 5B shows the inhibition of labeled $[I^{125}]$EGF to its receptors on A431 cells by mouse anti-human EGFR antibodies 225 and 528 (□, ∇, respectively; Calbiochem) and the fully human antibodies E1.1(●), E2.4 (▲), E2.5 (▼) and E2.11 (♦). The background binding of $[I^{125}]$EGF in the absence of antibodies was 1060 cpm. FIG. 5C shows inhibition of labeled $[I^{125}]$TNF-α binding to its receptors on U937 cells by the mouse anti-human TNF-α antibody (R&D Systems) (□) and fully human Mabs T22.1 (♦), T22.4 (●), T22.8 (▲), and T22.9 (■). The background binding of $[I^{125}]$TNF-α in the absence of antibody was 4010 cpm. Control human IgG2 myeloma antibody (⊠)

FIGS. 6A–6D (SEQ ID NODS 1–29, respectively, in order of appearance) show repertoire and somatic hypermutation in XenoMouse-derived fully human Mabs. Predicted amino acid sequences of four anti-IL-8 (FIGS. 6A, 6B) and four anti-EGFR (FIGS. 6C, 6D) human $IgG_2\kappa$ Mabs, divided into CDR1, CDR2 and CDR3 and the constant regions, $C_\gamma 2$ and $C_\kappa$. The D and J genes of each antibody are indicated. The amino acid substitutions from the germline sequences are indicated in bold letters.

FIGS. 12A–12I show a series of Southern Blot analyses demonstrating integration intact of the yK2 (human kappa light chain) YAC into ES cells and into the mouse genome. Detailed discussion is provided in connection with FIGS. 3A–3I.

FIG. 14 shows production levels of human antibodies by XenoMouse II strains in comparison to murine antibody production by wild type mice.

FIG. 15 is a repertoire analysis of human heavy chain transcripts expressed in XenoMouse II strains. The $V_H$ nucleotide sequences have been assigned SEQ ID NOS 30–41, respectively, in order of appearance. The 10-mer in column N (first instance) has been assigned SEQ ID NO: 42. The $4^{th}$, $5^{th}$, $6^{th}$, $9^{th}$ and $11^{th}$ nucleotide sequences in column $D_H$ have been assigned SEQ ID NOS 43, 44, 45, 46 and 47, respectively. The first and third nucleotide sequences in column N (second instance) have been assigned SEQ ID NOS 48 and 49, respectively. The nucleotide sequences in column $J_H$ have been assigned SEQ ID NOS 50–61, respectively, in order of appearance.

FIG. 16 is a repertoire analysis of human kappa light chain transcripts expressed in XenoMouse II strains. The $V_H$ sequences have been assigned SEQ ID NOS 62–69, respectively, in order of appearance. The Jκ sequences have been assigned SEQ ID NOS 70–77, respectively, in order of appearance.

Figure 17:

FIG. 17 is another depiction of the diverse utilization of human $V_H$ and Vκ genes that have been observed as utilized in XenoMouse II strains.

FIG. 18 shows the titers of human antibody production in XenoMouse II strains.

FIG. 19 is a depiction of gene utilization of anti-IL-8 antibodies derived from XenoMouse II strains.

FIG. 20 (SEQ ID NOS 1–8, respectively, in order of appearance) shows heavy chain amino acid sequences of anti-IL-8 antibodies derived from XenoMouse II strains.

FIG. 21 (SEQ ID NOS 9–16, respectively, in order of appearance) shows kappa light chain amino acid sequences of anti-IL-8 antibodies derived from XenoMouse II strains.

Figure 22:
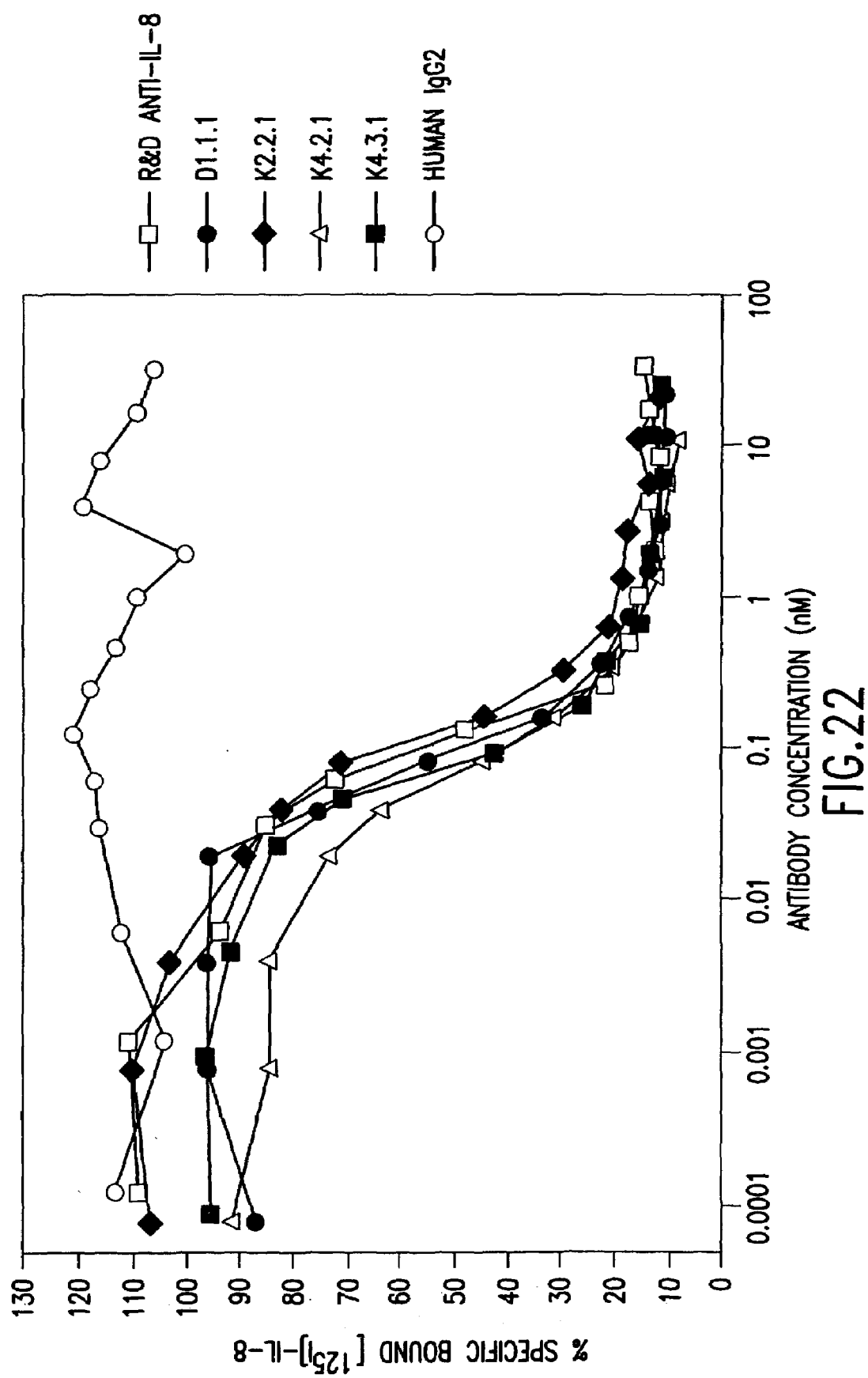

FIG. 22 shows blockage of IL-8 binding to human neutrophils by human anti-IL-8 antibodies derived from XenoMouse II strains.

Figure 23:
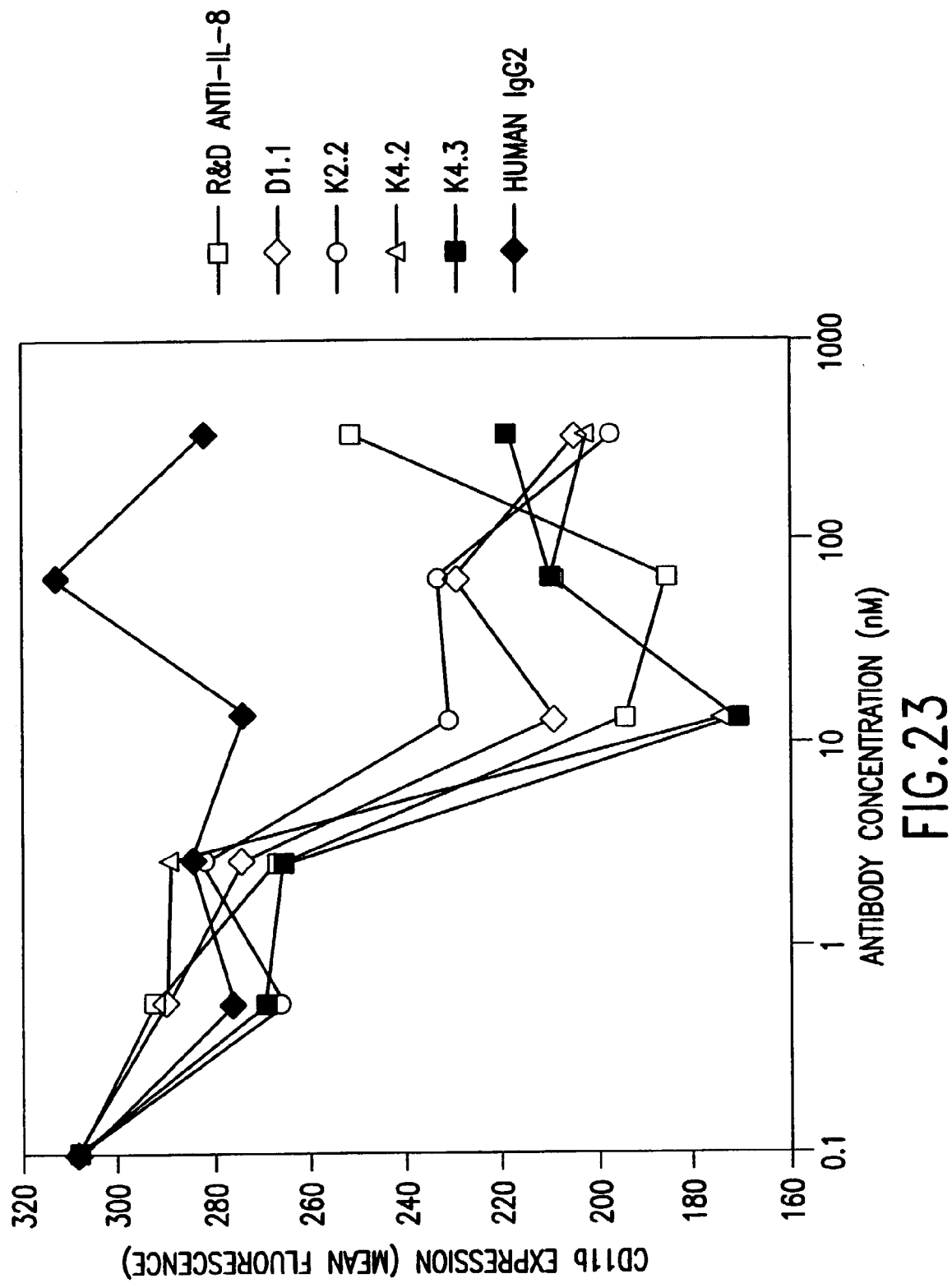

FIG. 23 shows inhibition of CD11b expression on human neutrophils by human anti-IL-8 antibodies derived from XenoMouse II strains.

Figure 24:
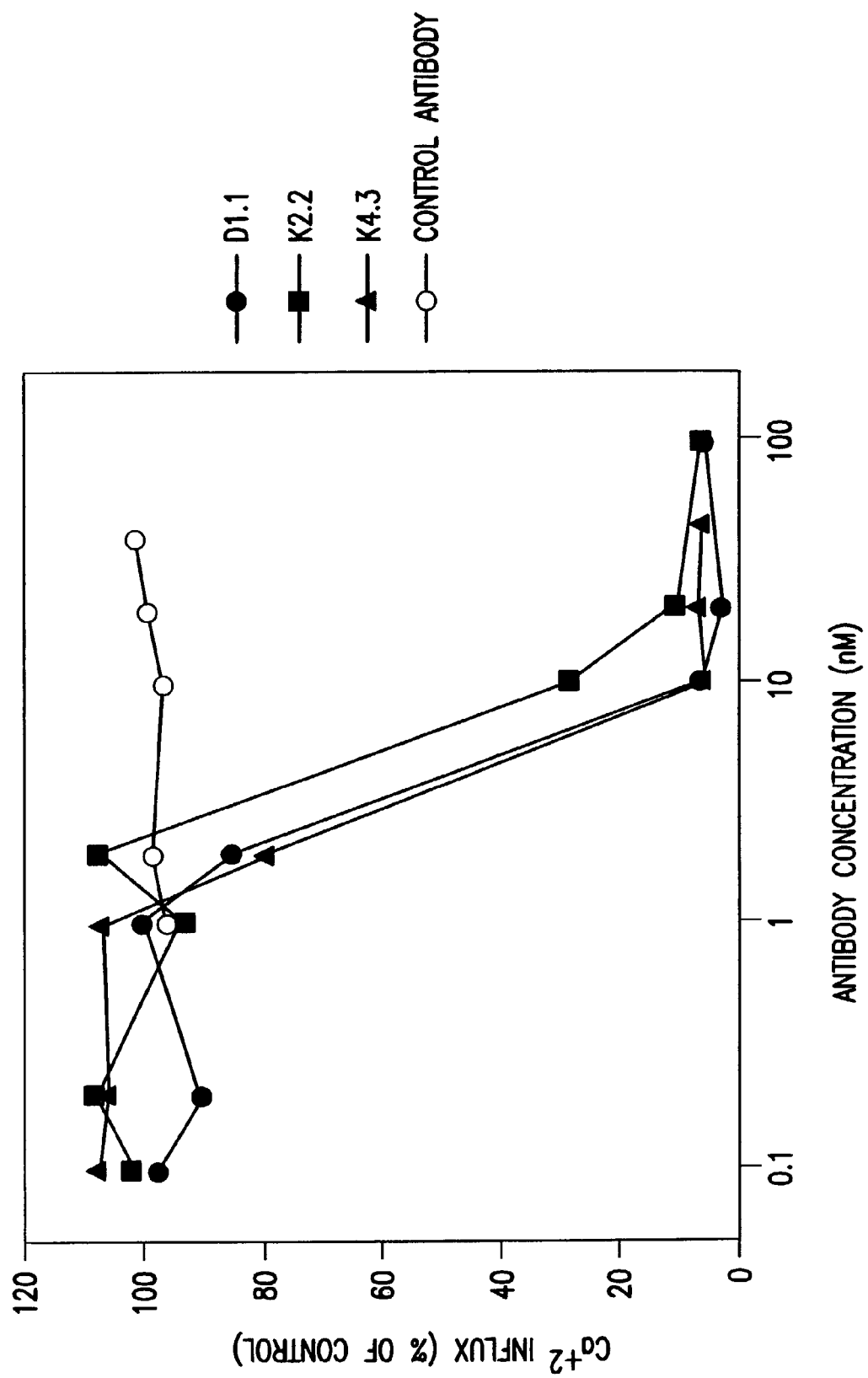

FIG. 24 shows inhibition of IL-8 induced calcium influx by human anti-IL-8 antibodies derived from XenoMouse II strains.

Figure 25:
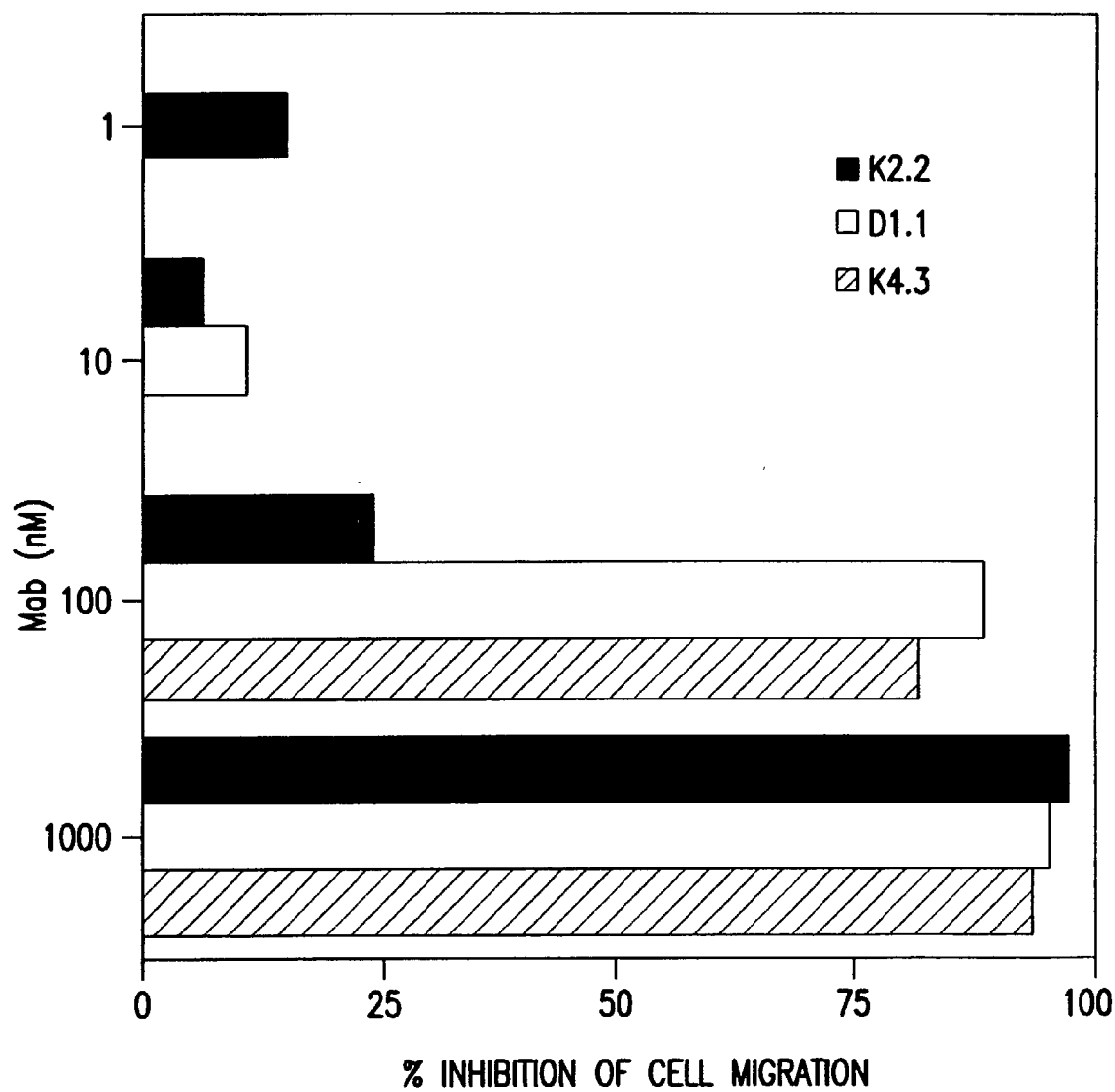

FIG. 25 shows inhibition of IL-8 RB/293 chemotaxsis by human anti-IL-8 antibodies derived from XenoMouse II strains.

Figure 26:
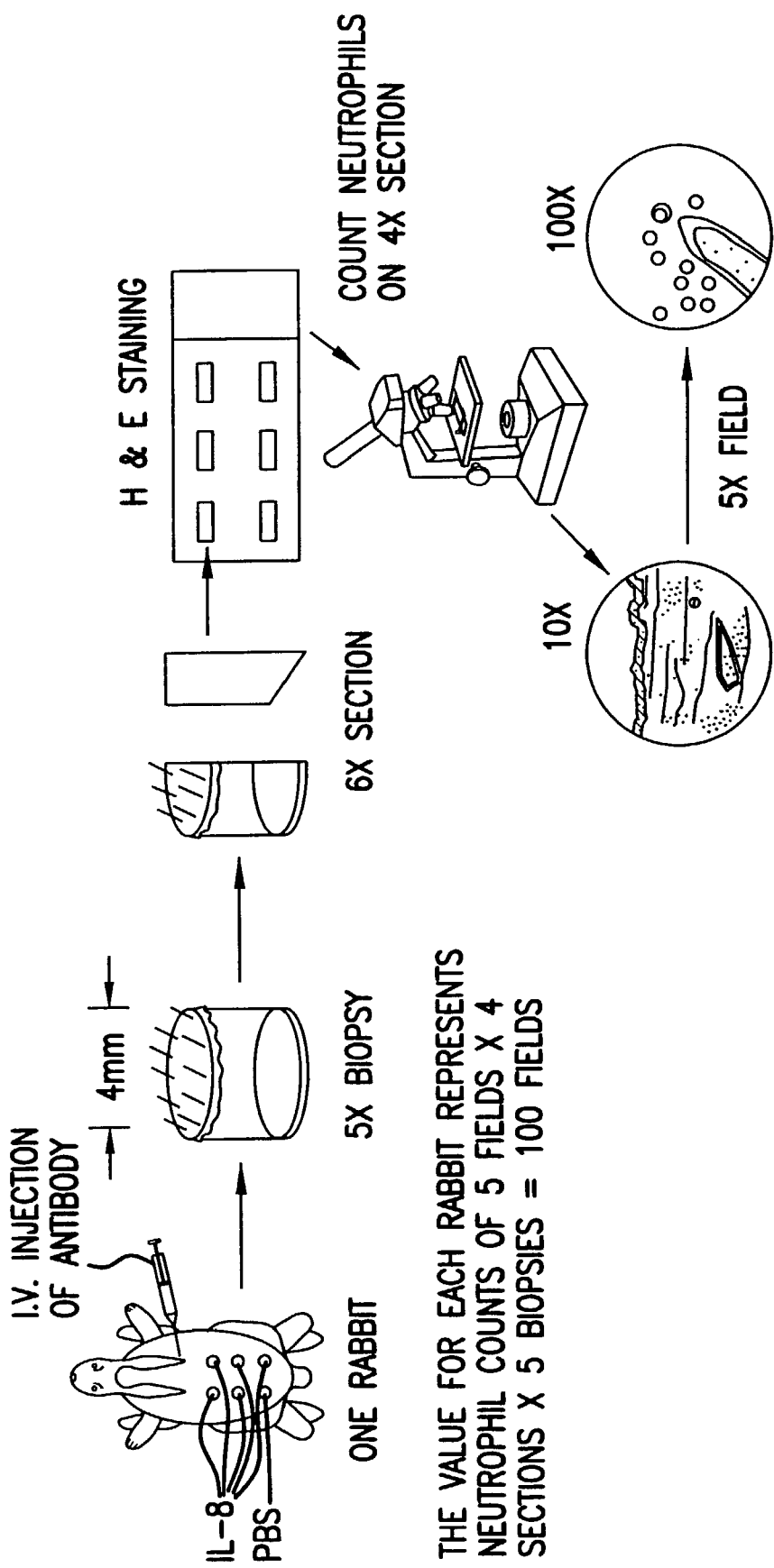

FIG. 26 is a schematic diagram of a rabbit model of human IL-8 induced skin inflammation.

Figure 27:
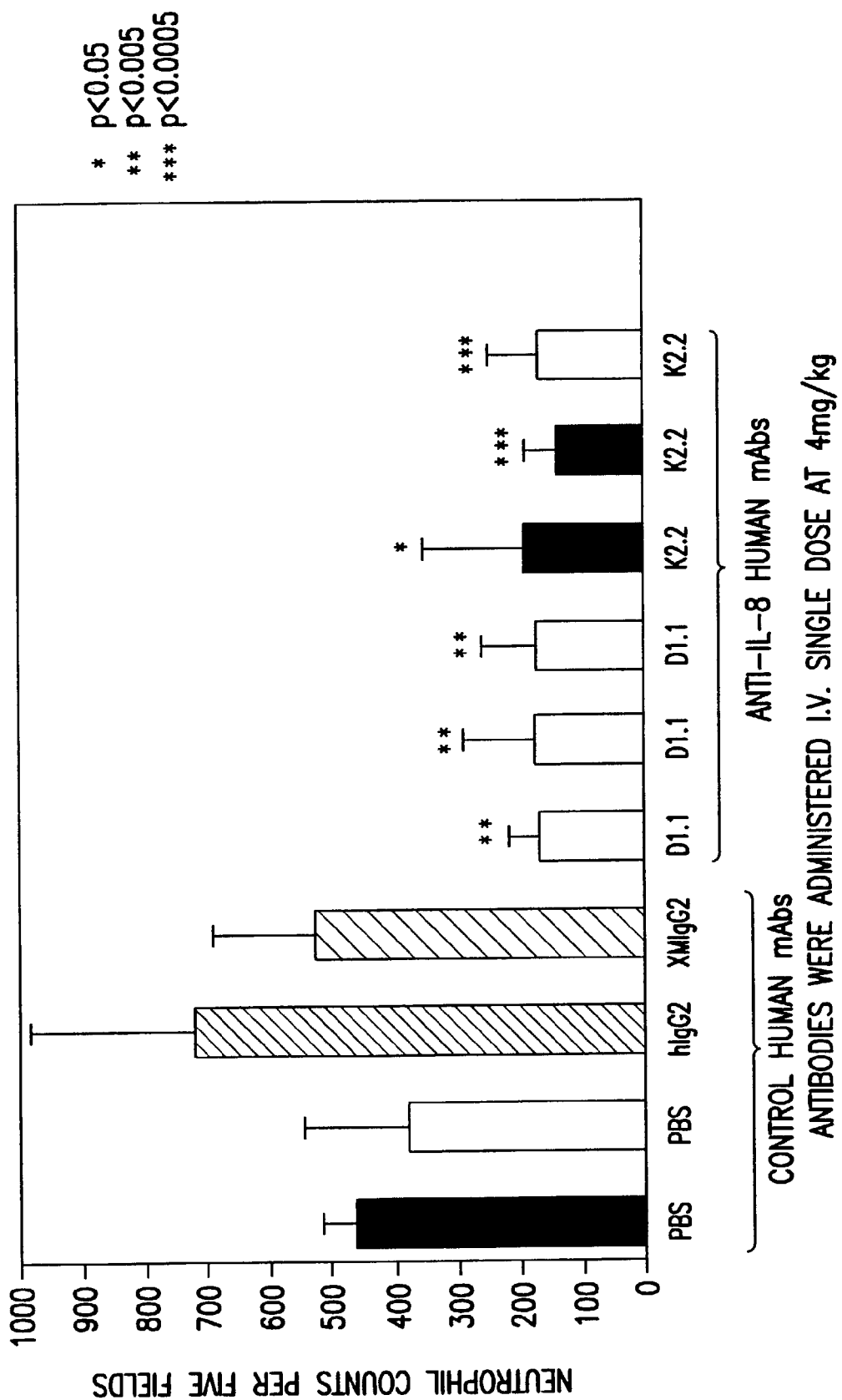

FIG. 27 shows the inhibition of human IL-8 induced skin inflammation in the rabbit model of FIG. 26 with human anti-IL-8 antibodies derived from XenoMouse II strains.

FIG. 28 shows inhibition of angiogenesis of endothelial cells on a rat corneal pocket model by human anti-IL-8 antibodies derived from XenoMouse II strains.

FIG. 29 is a depiction of gene utilization of human anti-EGFR antibodies derived from XenoMouse II strains.

Figure 30:
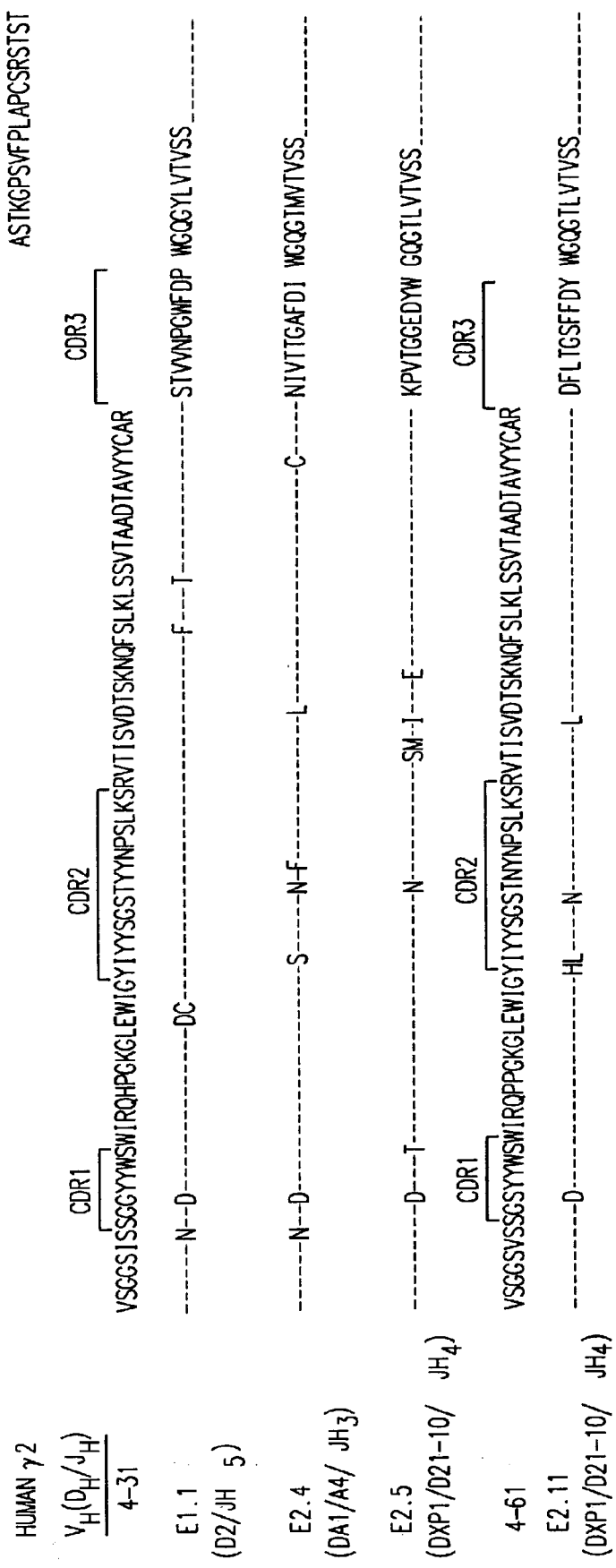

FIG. 30 (SEQ ID NOS 17–23, respectively, in order of appearance) shows heavy chain amino acid sequences of human anti-EGFR antibodies derived from XenoMouse II strains.

Figure 31:
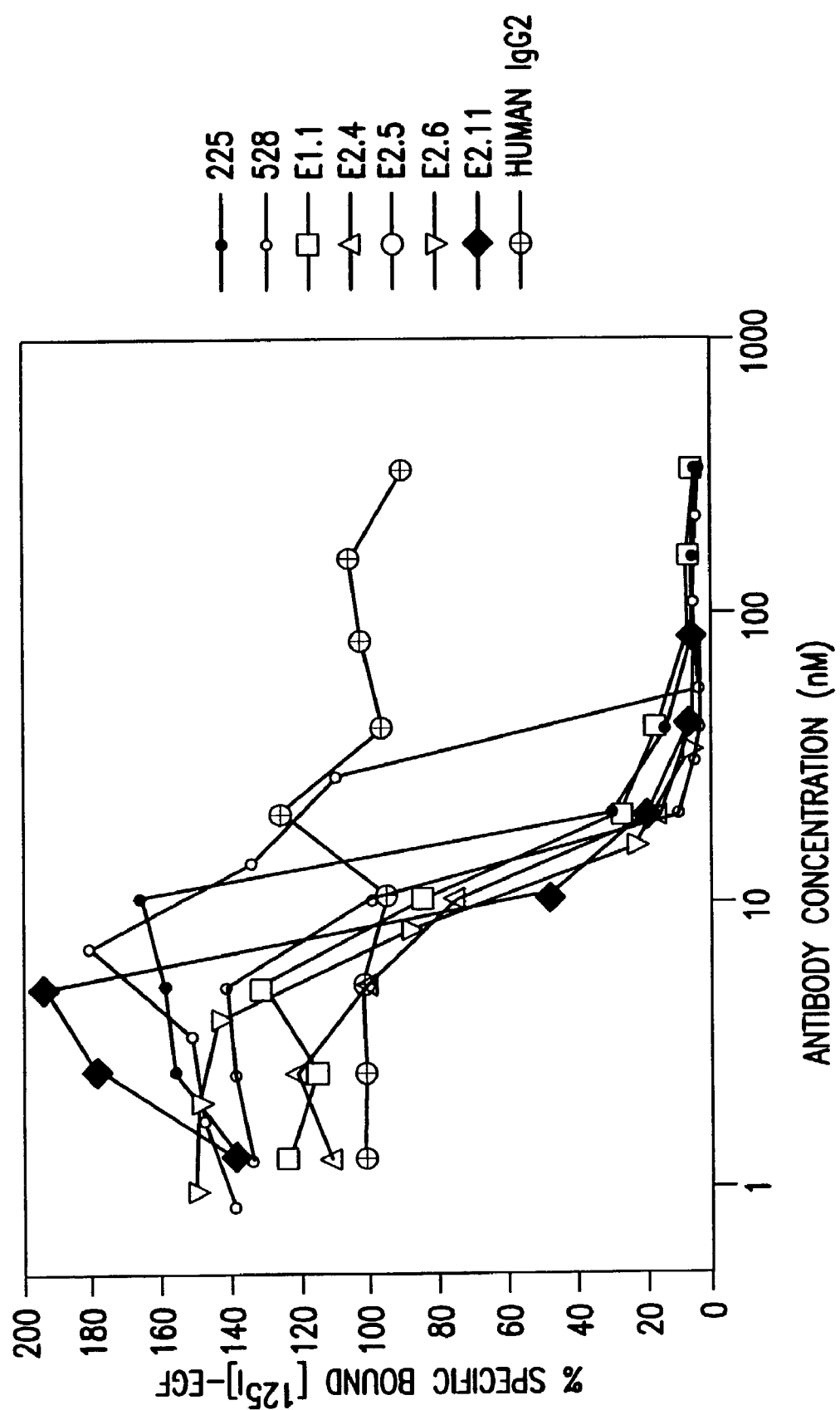

FIG. 31 shows blockage EGF binding to A431 cells by human anti-EGFR antibodies derived from XenoMouse II strains.

Figure 32:
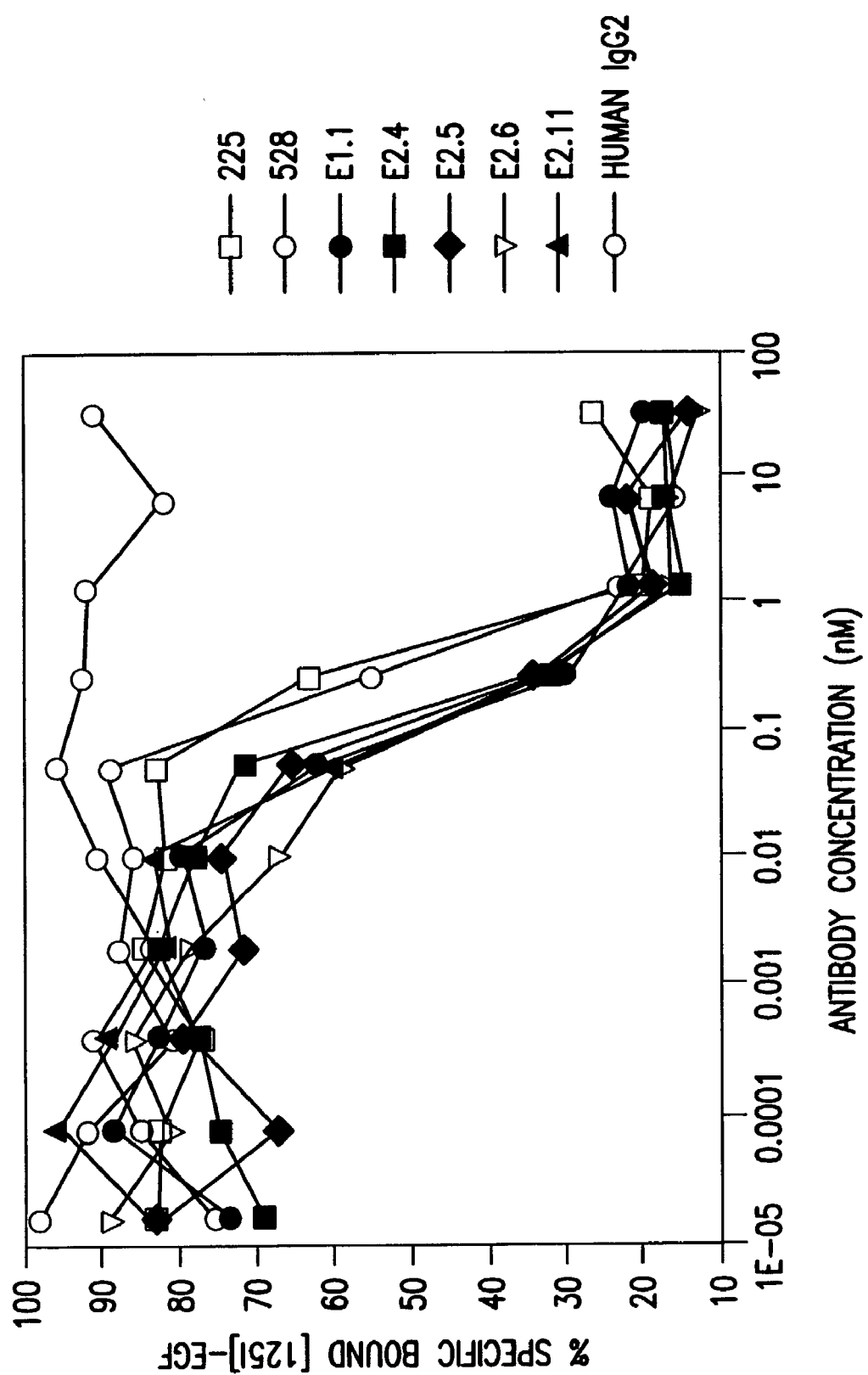

FIG. 32 shows inhibition of EGF binding to SW948 cells by human anti-EGFR antibodies derived from XenoMouse II strains.

Figure 33:
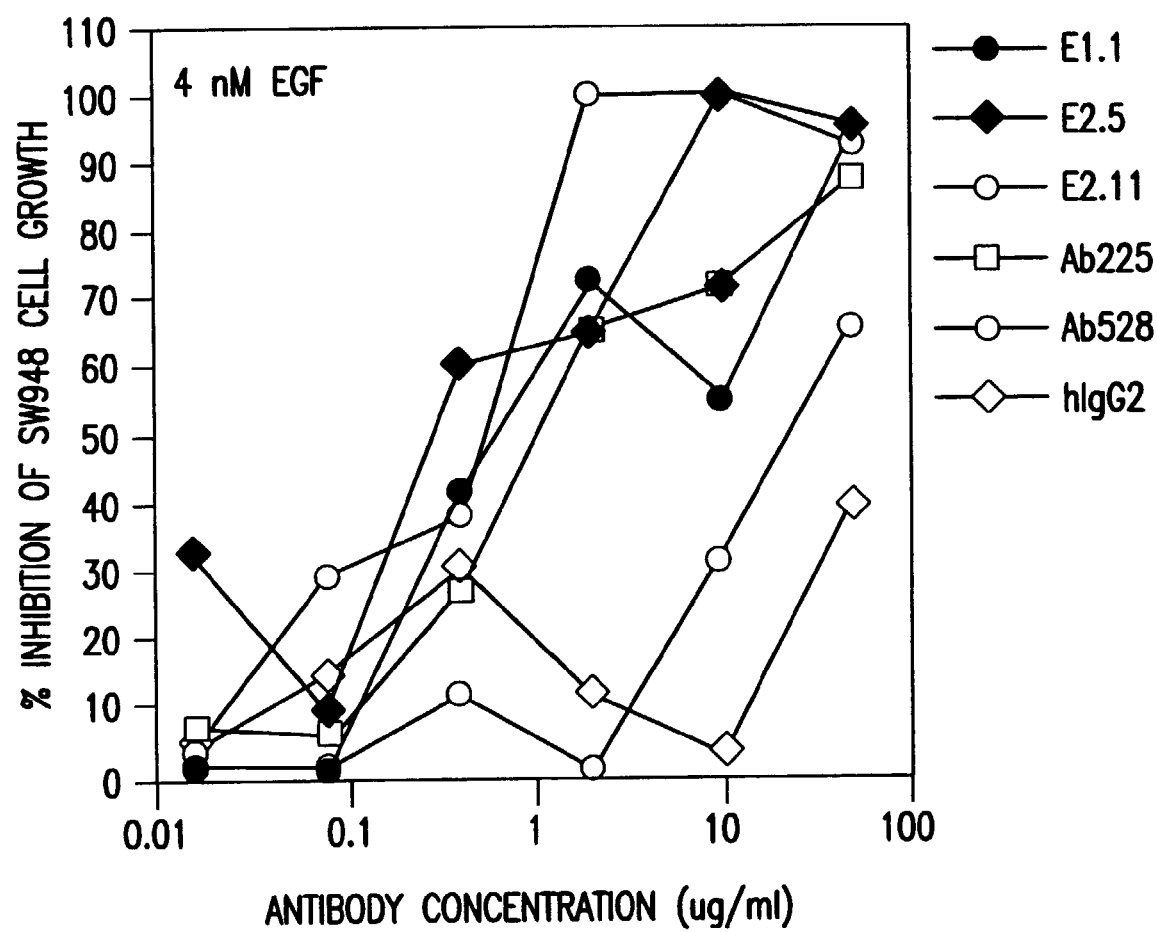

FIG. 33 shows that human anti-EGFR antibodies derived from XenoMouse II strains inhibit growth of SW948 cells in vitro.

Figure 34:
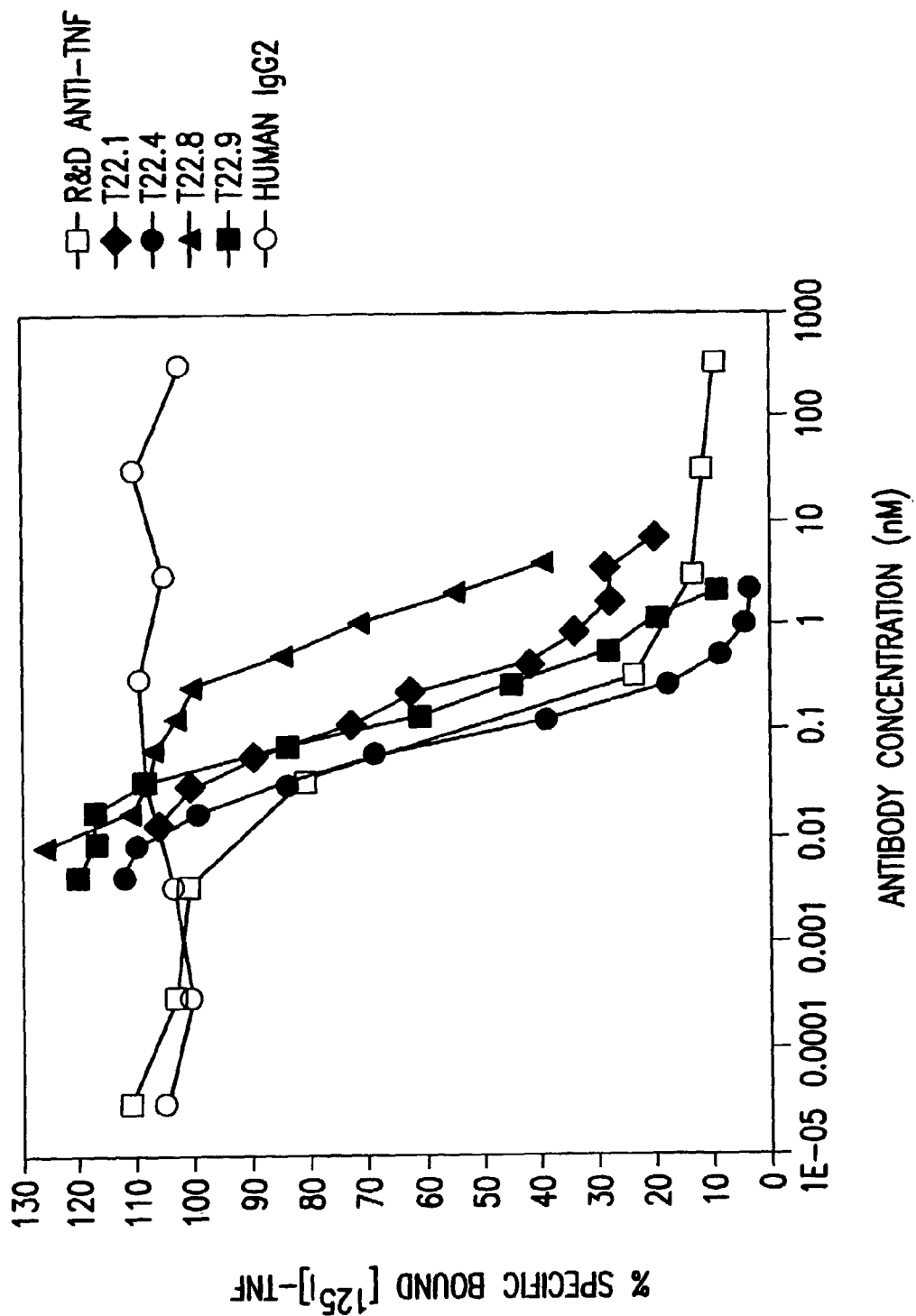

FIG. 34 shows inhibition of TNF-α binding to U937 cells through use of human anti-TNF-α antibodies derived from XenoMouse II strains.

DETAILED DESCRIPTION OF THE PREFERRED EMBODIMENTS

Herein we describe the generation and characterization of several strains of mice containing substantially germline configuration megabase-sized human Ig loci. The present invention thus provides the first demonstration of reconstruction of the large and complex human Ig loci on YACs and the successful introduction of megabase-sized YACs into mice to functionally replace the corresponding mouse loci.

Mouse Strains

The following mouse strains are described and/or utilized herein:

Double Inactivated (DI) Strain:

The DI strain of mice are mice that do not produce functional endogenous, mouse, Ig. In preferred embodiments, the DI mice possess an inactivated mouse $J_H$ region and an inactivated mouse $C_κ$ region. The construction of this strain is discussed extensively elsewhere. For example, the techniques utilized for generation of the DI strains are described in detail in U.S. patent application Ser. No. 07/466,008, filed Jan. 12, 1990, Ser. No. 07/610,515, filed Nov. 8, 1990, Ser. No. 07/919,297, filed Jul. 24, 1992, Ser. No. 08/031,801, filed Mar. 15, 1993, Ser. No. 08/112,848, filed Aug. 27, 1993, Ser. No. 08/234,145, filed Apr. 28, 1994, Ser. No. 08/724,752, filed Oct. 2, 1996. See also European Patent No., EP 0 463 151 B1, grant published Jun. 12, 1996, International Patent Application No., WO 94/02602, published Feb. 3, 1994, International Patent Application No., WO 96/34096, published Oct. 31, 1996, and PCT Application No. PCT/US96/05928, filed Apr. 29, 1996. The disclosures of each of the above-cited patent and patent applications are hereby incorporated by reference in their entirety. It has been observed and reported that DI mice possess a very immature B-cell development. The mice do not produce mature B-cells, only pro-B-cells.

XenoMouse I Strain:

The design, construction, and analysis of the XenoMouse I strain was discussed in detail in Green et al., *Nature Genetics*, 7:13–21 (1994). Such mice produced $IgM_κ$ antibodies against a DI background. The mice showed improved B-cell function when compared to the DI strain of mice which have little to no B-cell development. While XenoMouse I strains of mice were capable of mounting a sizeable immune response to antigenic challenge, there appeared to be inefficient in their production of B-cells and possessed a limited response to different antigens which apparently was related to their limited V-gene repertoire.

L6 Strain:

The L6 strain is a mouse producing $IgM_κ$ antibodies against a DI background of endogenous mouse Ig. L6 mice contain an inserted human heavy chain and an inserted human kappa light chain. The L6 strain is generated through breeding of a mouse containing a heavy chain insert against a double inactivated background (L6H) and a mouse having a kappa light chain insert against a double inactivated background (L6L). The heavy chain insert comprises an intact approximately 970 kb human DNA insert from a YAC containing approximately 66 $V_H$ segments, starting at $V_H6-1$ and ending at $V_H3-65$, and including the major D gene clusters (approximately 32), $J_H$ genes (6), the intronic enhancer (Eμ), Cμ, and through about 25 kb past Cδ, in germline configuration. The light chain insert comprises an intact approximately 800 kb human DNA insert from a YAC which contains approximately 32 $V_\kappa$ genes starting at $V_{\kappa\text{-}B3}$ and ending at $V_{\kappa\text{-}Op11}$. The 800 kb insert contains a deletion of approximately 100 kb starting at $V_{\kappa\text{-}Lp\text{-}13}$ and ending at $V_{\kappa Lp\text{-}5}$. However, the DNA is in germline configuration from $V_{\kappa Lp13}$ to 100 kb past $V_{\kappa\text{-}Op\text{-}1}$, and also contains the $J_\kappa$ genes, the intronic and 3' enhancers, the constant $C_\kappa$ gene, and Kde. The L6H and L6L mice have been shown to access the full spectrum of the variable genes incorporated into their genome. It is expected that the L6 mice will similarly access the full spectrum of variable genes in their genome. Furthermore, L6 mice will exhibit predominant expression of human kappa light chain, a large population of mature B-cells, and normal levels of $IgM_\kappa$ human antibodies. Such mice will mount a vigorous human antibody response to multiple immunogens, ultimately yielding antigen-specific fully human Mabs with subnanomolar affinities.

XenoMouse IIa Strain:

The XenoMouse IIa mice represent our second generation XenoMouse™ strains equipped with germline configuration megabase-sized human Ig loci, against a DI background, such that the mice do not produce functional endogenous Ig. Essentially, the mice are equivalent in construction to the L6 strain, but additionally include the human γ2 gene with its entire switch and regulatory sequences and the mouse 3' enhancer in cis. The mice contain an approximately 1020 kb heavy and an approximately 800 kb kappa light chain loci, reconstructed on YACs, which include the majority of the human variable region genes, including heavy chain genes (approximately 66 $V_H$) and kappa light chain genes (approximately 32 $V_\kappa$), human heavy constant region genes (μ, δ, and γ) and kappa constant region genes ($C_\kappa$), and all of the major identified regulatory elements. These mice have been shown to access the full spectrum of the variable genes incorporated into their genome. Furthermore, they exhibit efficient class switching and somatic hypermutation, predominant expression of human kappa light chain, a large population of mature B-cells, and normal levels of $IgM_\kappa$ and $IgG_\kappa$ human antibodies. Such mice mount a vigorous human antibody response to multiple immunogens, including human IL-8, human EGF receptor (EGFR), and human tumor necrosis factor-α(TNF-α), ultimately yielding antigen-specific fully human Mabs with subnanomolar affinities. This last result conclusively demonstrates XenoMouse™ as an excellent source for rapid isolation of high affinity, fully human therapeutic Mabs against a broad spectrum of antigens with any desired specificity.

As will be appreciated from the above-introduction, the XenoMouse II strain appears to undergo mature B-cell development and mount powerful adult-human-like immune responses to antigenic challenge. The L6 strain, as predicted from the data in connection with L6L and L6H mice, also appear to undergo mature B-cell development and mount powerful adult-human-like immune responses to antigenic challenge. When DI mice are compared to XenoMouse I strains and DI and XenoMouse I strains are compared to L6 and XenoMouse II strains, a markedly different B-cell development profile is observed. Owing to this difference, it appears that the quantity and/or quality of variable region sequences introduced into the animals are essential to the induction B-cell maturation and development and the generation of an adult-human-like immune response. Thus, in addition to the strains' clear use in the generation of human antibodies, the strains provide a valuable tool for studying the nature of human antibodies in the normal immune response, as well as the abnormal response characteristic of autoimmune disease and other disorders.

Variable Region—Quantitative Diversit

It is predicted that the specificity of antibodies (i.e., the ability to generate antibodies to a wide spectrum of antigens and indeed to a wide spectrum of independent epitopes thereon) is dependent upon the variable region genes on the heavy chain ($V_H$) and kappa light chain ($V_\kappa$) genome. The human heavy chain genome includes approximately 95 functional genes which encode variable regions of the human heavy chain of immunoglobulin molecules. In addition, the human light chain genome includes approximately 40 genes on its proximal end which encode variable regions of the human kappa light chain of immunoglobulin molecules. We have demonstrated that the specificity of antibodies can be enhanced through the inclusion of a plurality of genes encoding variable light and heavy chains.

Provided in accordance with the present invention are transgenic mice having a substantial portion of the human Ig locus, preferably including both a human heavy chain locus and a human kappa light chain locus. In preferred embodiments, therefore, greater than 10% of the human $V_H$ and $V_\kappa$ genes are utilized. More preferably, greater than about 20%, 30%, 40%, 50%, 60%, or even 70% or greater of $V_H$ and $V_\kappa$ genes are utilized. In a preferred embodiment, constructs including 32 genes on the proximal region of the Vκ light chain genome are utilized and 66 genes on the $V_H$ portion of the genome are utilized. As will be appreciated, genes may be included either sequentially, i.e., in the order found in the human genome, or out of sequence, i.e., in an order other than that found in the human genome, or a combination thereof. Thus, by way of example, an entirely sequential portion of either the $V_H$ or $V_\kappa$ genome can be utilized, or various V genes in either the $V_H$ or $V_\kappa$ genome can be skipped while maintaining an overall sequential arrangement, or V genes within either the $V_H$ or $V_\kappa$ genome can be reordered, and the like. In a preferred embodiment, the entire inserted locus is provided in substantially germline configuration as found in humans. In any case, it is expected and the results described herein demonstrate that the inclusion of a diverse array of genes from the $V_H$ and $V_\kappa$ genome leads to enhanced antibody specificity and ultimately to enhanced antibody affinities.

Further, preferably such mice include the entire $D_H$ region, the entire $J_H$ region, the human mu constant region, and can additionally be equipped with other human constant regions for the coding and generation of additional isotypes of antibodies. Such isotypes can include genes encoding $\gamma_1$, $\gamma_2$, $\gamma_3$, $\gamma_4$, α, ε, and δ and other constant region encoding genes with appropriate switch and regulatory sequences. As will be appreciated, and as discussed in more detail below, a variety of switch and regulatory sequences can be appropriately utilized in connection with any particular constant region selection.

The following Table indicates the diversity of antibody combinations that are possible in humans, based strictly on random V-D-J joining and combination with kappa light chains, without consideration of N-addition or somatic mutation events. Based on these considerations, there are greater than 3.8 million possible antibody combinations in humans, of any particular isotype.

TABLE I

| Region | Heavy Chain | Kappa Light Chain |
|---|---|---|
| Variable "V" | ~95 | 40 |
| Diversity "D" | ≧32 | — |
| Joining "J" | 6 | 5 |
| Combinations (V × D × J) | 18,240 | 200 |
| Total Combinations (HC Combinations × LC Combinations) | 3.65 × 10$^6$ | |

In connection with a preferred embodiment of the invention, through the inclusion of about 66 $V_H$ genes and 32 $V_\kappa$ genes in a mouse with a full complement of $D_H$, $J_H$, and Jκ genes, the possible diversity of antibody production is on the order of 2.03×10$^6$ different antibodies. As before, such calculation does not take into account N-addition or somatic mutation events. Therefore, it will be appreciated that mice in accordance with the invention, such as the L6 and the XenoMouse II strains, offer substantial antibody diversity. In preferred embodiments, mice are designed to have the capability of producing greater than 1×10$^6$ different heavy chain V-D-J combinations and kappa light chain V-J combinations, without accounting for N-additions or somatic mutation events.

Variable Region—Qualitative Diversity

In addition to quantitative diversity, quantitative selection of V-genes (i.e., large and diverse numbers of V-genes) and/or qualitative selection of V-genes (i.e., selection of particular V-genes) appears to play a role in what we refer to herein as "qualitative diversity." Qualitative diversity, as used herein, refers to diversity in V-D-J rearrangements wherein junctional diversity and/or somatic mutation events are introduced. During heavy chain rearrangement, certain enzymes (RAG-1, RAG-2, and possibly others) are responsible for the cutting of the DNA representing the coding regions of the antibody genes. Terminal deoxynucleotidyl transferase (Tdt) activity is upregulated which is responsible for N-terminal additions of nucleotides between the V-D and D-J gene segments. Similar enzymes and others (SCID and other DNA repair enzymes) are responsible for the deletion that occurs at the junctions of these coding segments. With respect to junctional diversity, both N-addition events and formation of the complementarity determining region 3 (CDR3) are included within such term. As will be appreciated, CDR3 is located across the D region and includes the V-D and D-J junctional events. Thus, N-additions and deletions during both D-J rearrangement and V-D rearrangement are responsible for CDR3 diversity.

It has been demonstrated that there are certain differences between murine and human junctional diversities. In particular, some researchers have reported that murine N-addition lengths and CDR3 lengths are generally shorter than typical human N-addition lengths and CDR3 lengths. Such groups have reported that, in humans, N-additions of about 7.7 bases in length, on average, are typically observed. Yamada et al. (1991). Mouse-like N-additions are more often on the order of about 3 bases in length, on average. Feeney et al. (1990). Similarly, human-like CDR3 lengths are longer than mouse-like CDR3's. In man CDR3 lengths of between 2 and 25 residues, with an average of 14 residues, is common. In mice, some groups have reported shorter average CDR3 lengths.

The junctional diversity created by N-additions and CDR3 additions play a clear role developing antibody specificity.

In accordance with the invention, rearranged V-D-J gene sequences show N-addition lengths that are comparable to expected adult-human N-addition lengths. Further, amino acid sequences across the open reading frame (ORF) corresponding to CDR3 sequences show CDR3 lengths that are comparable to expected adult-human CDR3 lengths. Such data is indicative that quantitative variable region diversity and/or qualitative variable region diversity results in human-like junctional diversity. Such junctional diversity is expected to lead to a more human-like antibody specificity.

Variable Region—Affinities

While we have not conclusively demonstrated a direct causal connection between the increased variable region inclusion and antibody specificity, it appears, and it is expected that through providing such diversity, the ability of the mouse to mount an immune response to a wide array of antigens is possible and enhanced. Additionally, such mice appear more equipped to mount immune responses to a wide array of epitopes upon individual antigens or immunogens. From our data it also appears that antibodies produced in accordance with the present invention possess enhanced affinities. Such data includes comparisons between mice in accordance with the invention and the XenoMouse I strains, as well as consideration of the published results of GenPharm International and the MRC. In connection with the XenoMouse I strains, as mentioned above, such mice possessed inefficient B-cell production and a limited response to different antigens. Such result appeared related in part to the limited V-gene repertoire. Similarly, results reported by GenPharm International and the MRC indicate a limited response to diverse antigens.

Without wishing to bound to any particular theory or mode of operation of the invention, it would appear that enhanced affinities appear to result from the provision of the large number of V regions. From our data, the provision of greater numbers and/or selection of qualities of V-gene sequences, enhances junctional diversity (N-additions and formation of complementarity determining region 3 ("CDR3") diversity), which is typical of an adult-human-like immune response, and which play a substantial role in affinity maturation of antibodies. It may also be that such antibodies are more effective and efficient in somatic mutation events that lead to enhanced affinities. Each of junctional diversity and somatic mutation events are discussed in additional detail below.

With respect to affinities, antibody affinity rates and constants derived through utilization of plural $V_H$ and $V_\kappa$ genes (i.e., the use of 32 genes on the proximal region of the $V_\kappa$ light chain genome and 66 genes on the $V_H$ portion of the genome) results in association rates (ka in $M^{-1}S^{-1}$) of greater than about 0.50×10$^{-6}$, preferably greater than 2.00× 10$^{-6}$, and more preferably greater than about 4.00×10$^{-6}$; dissociation rates (kd in $S^{-1}$) of greater than about 1.00× 10$^{-4}$, preferably greater than about 2.00×10$^{-4}$, and more preferably greater than about 4.00×10$^{-4}$; and dissociation constant (in M) of greater than about 1.00×10$^{-10}$, preferably greater than about 2.00×10$^{-10}$, and more preferably greater than about 4.00×10$^{-10}$.

Preferably, such mice additionally do not produce functional endogenous immunoglobulins. This is accomplished in a preferred embodiment through the inactivation (or knocking out) of endogenous heavy and light chain loci. For example, in a preferred embodiment, the mouse heavy chain J-region and mouse kappa light chain J-region and $C_\kappa$-region are inactivated through utilization of homologous recombination vectors that replace or delete the region.

Variable Region —B-Cell Development

B-cell development is reviewed in Klaus *B Lymphocytes* (IRL Press (1990)) and Chapters 1–3 of Immunoglobulin Genes (Academic Press Ltd. (1989)), the disclosures of which are hereby incorporated by reference. Generally, in mammals, blood cell development, including B- and T-cell lymphocytes, originate from a common pluripotent stem cell. The lymphocytes, then, evolve from a common lymphoid progenitor cell. Following an early gestational period, B-cell initiation shifts from the liver to the bone marrow where it remains throughout the life of the mammal.

In the life cycle of a B-cell, the first generally recognizable cell is a pro-pre-B-cell which is found in the bone marrow. Such a cell has begun heavy chain V-D-J rearrangement, but does not yet make protein. The cell then evolves into a large, rapidly dividing, pre-B-cell I which is a cytoplasmically $\mu^+$ cell. This pre-B-cell I then stops dividing, shrinks, and undergoes light chain V-J rearrangement becoming a pre-B-cell II which expresses surface IgM, which leave the marrow as immature B-cells. Most of the emerging immature B-cells continue to develop and to produce surface IgD, indicative of their completion of differentiation and development as fully mature immunocompetent peripheral B-cells, which reside primarily in the spleen. However, it is possible to eliminate the delta constant region and still obtain immunocompetent cells.

B-cell differentiation and development can be monitored and/or tracked through the use of surface markers. For example, the B220 antigen is expressed in relative abundance on mature B-cells in comparison to pre-B-cells I or II. Thus, cells that are B220$^+$ and surface IgM$^+$ ($\mu^+$) can be utilized to determine the presence of mature B-cells. Additionally, cells can be screened for surface IgD expression ($\delta^+$). Another antigen, heat stable antigen, is expressed by pre-B-cells II as they transition to the periphery (i.e., as they become $\mu^+$ and/or $\mu^+$, $\delta_+$).

TABLE II

| | Bone Marrow | | | Spleen | |
|---|---|---|---|---|---|
| Marker | pro-pre-B-cell | pre-B-cell I | pre-B-cell II emerging B-cell | immature B-cell | mature B-cell |
| B220 | − | − | ± | + | ++ |
| HSA | − | − | + | ± | − |
| µ | − | − | + | + | + |
| δ* | − | − | − | − | + |

*Assuming the presence of a functional copy of the Cδ gene on the transgene.

Through use of B-cell markers, such as those mentioned above, development and differentiation of B-cells can be monitored and assessed.

We have previously demonstrated that DI mice (mice that do not undergo heavy chain V-D-J rearrangement or light chain V-J rearrangement) do not produce mature B-cells. In fact, such mice arrest at the production of pro-pre-B-cells and B-cells never move from the bone marrow to peripheral tissues, including the spleen. Thus, both B-cell development and antibody production are completely arrested. The same result is seen in mice that are only heavy chain inactivated; B-cell development and differentiation arrests in the bone marrow.

Our XenoMouse I strain produced functional, somewhat mature B-cells. However, the numbers of B-cells, in both the bone marrow and peripheral tissues, were significantly reduced relative to wild type mice.

In contrast, our XenoMouse II strains and L6 strains, unexpectedly possess almost complete B-cell reconstitution. Therefore, in accordance with the invention, we have demonstrated that through the quantitative inclusion or qualitative inclusion of variable region genes B-cell differentiation and development can be greatly reconstituted. Reconstitution of B-cell differentiation and development is indicative of immune system reconstitution. In general, B-cell reconstitution is compared to wild type controls. Thus, in preferred embodiments of the invention, populations of mice having inserted human variable regions possess greater than about 50% B-cell function when compared to populations of wild type mice.

Further, it is interesting to note that production of human antibodies in preference to mouse antibodies is substantially elevated in mice having a knock-out background of endogenous Ig. That is to say that mice that contain a human Ig locus and a functionally inactivated endogenous heavy chain Ig locus produce human antibodies at a rate of approximately 100 to 1000 fold as efficiently as mice that only contain a human Ig locus and are not inactivated for the endogenous locus.

Isotype Switching

As is discussed in detail herein, as expected, XenoMouse II mice undergo efficient and effective isotype switching from the human transgene encoded mu isotype to the transgene encoded gamma-2 isotype. We have also developed XenoMouse II strains that contain and encode the human gamma-4 constant region. As mentioned above, mice in accordance with the invention can additionally be equipped with other human constant regions for the generation of additional isotypes. Such isotypes can include genes encoding $\gamma_1$, $\gamma_2$, $\gamma_3$, $\gamma_4$, $\alpha$, $\epsilon$, $\delta$, and other constant region encoding genes. Alternative constant regions can be included on the same transgene, i.e., downstream from the human mu constant region, or, alternatively, such other constant regions can be included on another chromosome. It will be appreciated that where such other constant regions are included on the same chromosome as the chromosome including the human mu constant region encoding transgene, cis-switching to the other isotype or isotypes can be accomplished. On the other hand, where such other constant region is included on a different chromosome from the chromosome containing the mu constant region encoding transgene, trans-switching to the other isotype or isotypes can be accomplished. Such arrangement allows tremendous flexibility in the design and construction of mice for the generation of antibodies to a wide array of antigens.

It will be appreciated that constant regions have known switch and regulatory sequences that they are associated with. All of the murine and human constant region genes had been sequenced and published by 1989. See Honjo et al. "Constant Region Genes of the Immunoglobulin Heavy Chain and the Molecular Mechanism of Class Switching" in *Immunoglobulin Genes* (Honjo et al. eds., Academic Press (1989)), the disclosure of which is hereby incorporated by reference. For example, in U.S. patent application Ser. No. 07/574,748, the disclosure of which is hereby incorporated by reference, the cloning of the human gamma-1 constant region was prophesized based on known sequence information from the prior art. It was set forth that in the unrearranged, unswitched gene, the entire switch region was included in a sequence beginning less than 5 kb from the 5' end of the first γ-1 constant exon. Therefore the switch region was also included in the 5' 5.3 kb HindIII fragment that was disclosed in Ellison et al. *Nucleic Acids Res.* 10:4071–4079 (1982). Similarly, Takahashi et al. *Cell* 29:671–679 (1982) also reported that the fragment disclosed in Ellison contained the switch sequence, and this fragment together with the 7.7 kb HindIII to BamHI fragment must include all of the sequences necessary for the heavy chain isotype switching transgene construction.

Thus, it will be appreciated that any human constant region of choice can be readily incorporated into mice in accordance with the invention without undue experimentation. Such constant regions can be associated with their native switch sequences (i.e., a human $\gamma_{1, 2, 3, or 4}$ constant region with a human $Y_{1, 2, 3, or 4}$ switch, respectively) or can be associated with other switch sequences (i.e., a human $\gamma_4$ constant region with a human $\gamma_2$ switch). Various 3' enhancer sequences can also be utilized, such as mouse, human, or rat, to name a few. Similarly other regulatory sequences can also be included.

As an alternative to, and/or in addition to, isotype switching in vivo, B-cells can be screened for secretion of "chimeric" antibodies. For example, the L6 mice, in addition to producing fully human IgM antibodies, produce antibodies having fully human heavy chain V, D, J regions coupled to mouse constant regions, such as a variety of gammas (i.e., mouse IgG1, 2, 3, 4) and the like. Such antibodies are highly useful in their own right. For example, human constant regions can be included on the antibodies through in vitro isotype switching techniques well known in the art. Alternatively, and/or in addition, fragments (i.e., F(ab) and F(ab')$_2$ fragments) of such antibodies can be prepared which contain little or no mouse constant regions.

As discussed above, the most critical factor to antibody production is specificity to a desired antigen or epitope on an antigen. Class of the antibody, thereafter, becomes important according to the therapeutic need. In other words, will the therapeutic index of an antibody be enhanced by providing a particular isotype or class? Consideration of that question raises issues of complement fixation and the like, which then drives the selection of the particular class or isotype of antibody. Gamma constant regions assist in affinity maturation of antibodies. However, the inclusion of a human gamma constant region on a transgene is not required to achieve such maturation. Rather, the process appears to proceed as well in connection with mouse gamma constant regions which are trans-switched onto the mu encoded transgene.

Materials and Methods

The following Materials and Methods were utilized in connection with the generation and characterization of mice in accordance with the present invention. Such Materials and Methods are meant to be illustrative and are not limiting to the present invention.

Cloning Human Ig-derived YACs:

The Washington University (Brownstein et al., 1989) and the CEPH (Albertsen et al., 1990) human-YAC libraries were screened for YACs containing sequences from the human heavy and kappa light chain loci as previously described (Mendez et al. 1995). Cloning and characterization of 1H and 1K YACs was described by Mendez et al., (1995). 3H and 4H YACs were identified from the Washington University library using a $V_H3$ probe (0.55 kb PstI/NcoI, Berman et al, 1988). The 17H YAC was cloned from the GM1416 YAC library and determined to contain 130 kb of heavy chain variable sequences and a 150 kb chimeric region at its 3' end Matsuda et. al., 1993. 2K and 3K YACs were recovered from the CHEF library using $V_\kappa$II-specific primer (Albertsen et al., 1990).

YAC Targeting and Recombination:

Standard methods for yeast growth, mating, sporulation, and phenotype testing were employed (Sherman et al, 1986). Targeting of YAC's and YAC vector arms with yeast and mammalian selectable markers, to facilitate the screening of YAC recombinants in yeast of YAC integration into cells, was achieved by lithium acetate transformation (Scheistl and Geitz (1989). After every targeting or recombination step the modified YAC(s) was analyzed by pulsed field gel electrophoresis and standard Southern Blots to determine the integrity of all sequences.

Figure 1A:
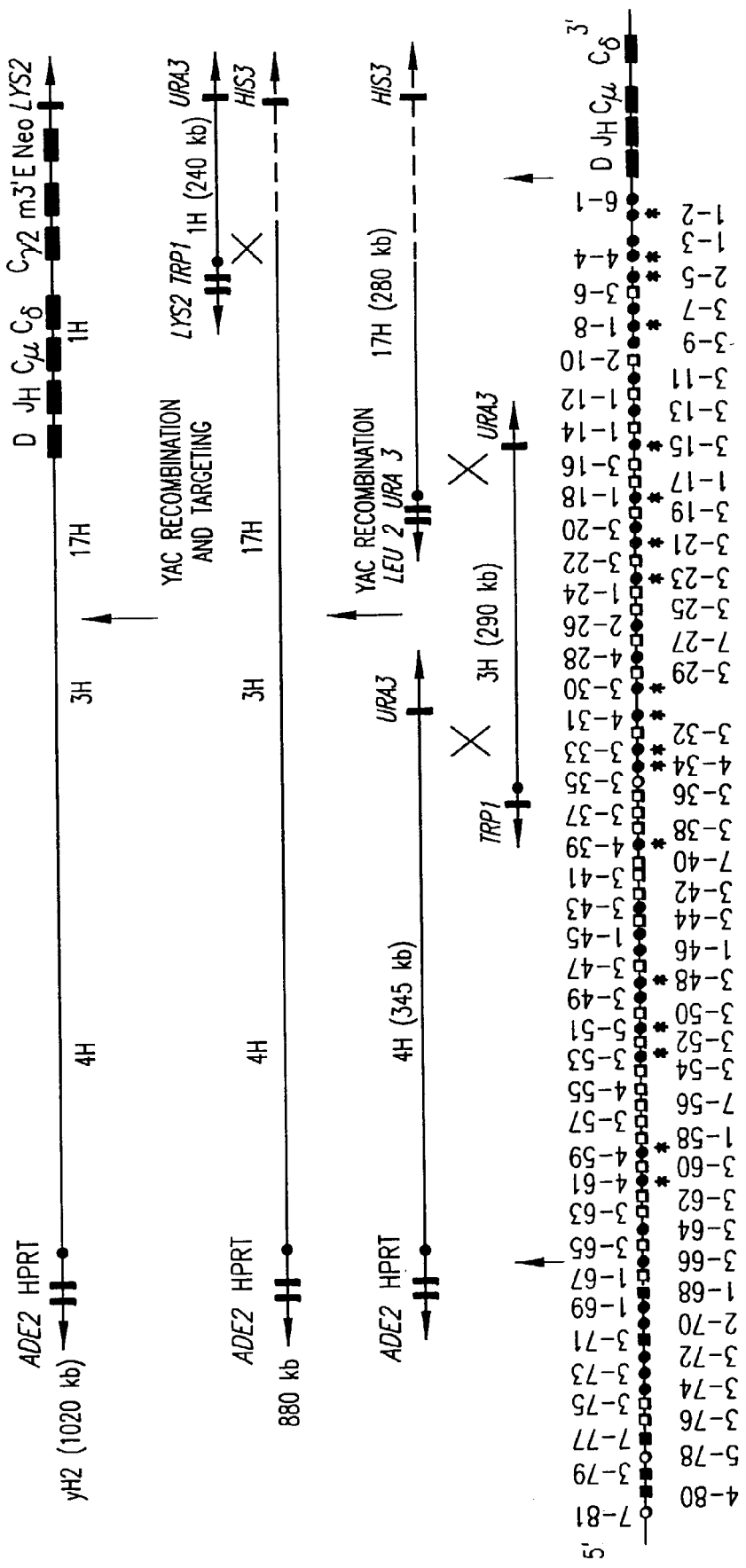

YAC targeting vectors were used for the interconversion of centric and acentric arms to reorient 17H and to retrofit its 5' arm with LEU2 and URA3 genes and its 3' arm with the HIS3 gene. See FIG. 1*a* and Mendez et al., 1993. The 4H centric arm was retrofitted with the yeast ADE2 gene and the human HPRT selectable markers. For the first recombination step, a diploid yeast strain was created and selected in which all three YACs 17H, 3H, and 4H were present, intact, and stably maintained. A three-way homologous recombination between the YAC overlapping regions was induced by sporulation and the desired recombinant was found by the selection of the outer yeast selectable markers (ADE2 and HIS3) and negative selection (loss) of the internal marker URA3. The successful recombination created a 880 kb YAC containing 80% of the IgH variable region, starting at $V_H2$–5 and extending 20 kb 5' of the $V_H3$-65 gene. For the recombination of the 880 kb YAC to 1H, 1H was retrofitted with pICL, which adds the LYS2 gene to the centric arm (Hermanson et al., 1991). Using standard yeast mating, a diploid strain was selected containing both 1H and the 880 kb YAC. Upon sporulation and by use of overlapping homology, YAC-yeast recombination was carried out. With positive selection for the outer yeast markers (ADE2 and URA3) and screening for the loss of the internal markers (TRP1, LYS2, HIS3), an intact 970 kb YAC consisting of approximately 66 $V_H$ segments, starting at $V_H6$-1 and ending at $V_H3$-65 was found. The YAC also contained the major D gene clusters, $J_H$ genes, the intronic enhancer (Eμ), Cμ, up to 25 kb past Cδ, in germline configuration. This 970 kb YAC was then retrofitted with a targeting vector including a 23 kb EcoRI genomic fragment of the human γ-2 gene, including its switch and regulatory elements, a 7 kb XbaI fragment of the murine heavy chain 3' enhancer, neomycin gene driven by the metallothionine promoter (MMTNeo), and the yeast LYS2 gene. This vector, while bringing in these sequences on the 3' YAC arm, disrupts the URA3 gene.

As a first step toward creating yK2 YAC, by standard yeast mating a diploid yeast strain was selected in which retrofitted 1K and 3K YACs were both present, intact, and stably maintained. Using the same process as described in connection with the IgH construction, YAC-yeast recombination was carried out. Through use of positive selection for the outer yeast markers (LYS2, TRP1) and the screening for the loss of internal markers (URA3, TRP1), an intact 800 kb recombinant product was found which contained 32 $V_\kappa$ starting at $V_{\kappa-B3}$ and ending at $V_{\kappa-Op11}$. The 800 kb YAC contains a deletion of approximately 100 kb starting at $V_{\kappa Lp-13}$ and ending at $V_{\kappa-Lp5}$. However, the YAC is in germline configuration from $V_{\kappa Lp-13}$ to 100 kb past $V_{\kappa-Op-1}$. The YAC also contains $J_\kappa$, the intronic and 3' enhancers, the constant $C_\kappa$, and Kde.

YAC Introduction into ES Cells and Mice:

YAC-containing yeast spheroplasts were fused with E14.TG3B1 ES cells as described (Jakobivits et al., 1993a; Green et al., 1994). HAT-resistant colonies were expanded for analysis. YAC integrity was evaluated by Southern Blot analysis using protocols and probes described in Berman et al., (1988) and Mendez et al., (1994) and hybridization conditions as described in Gemmil et al., (1991). Chimeric mice were generated by microinjection of ES cells into C57BL/6 blastocysts. YAC-containing offspring were identified by PCR analysis of tail DNA as described (Green et al., 1994). YAC integrity was evaluated by Southern Blot analysis using probes and conditions previously described, except that the blot probed with human $V_H3$ was washed at 50° C.

Flow Cytometry Analysis:

Peripheral blood and spleen lymphocytes obtained from 8–10 week old XenoMice and control mice were purified on Lympholyte M (Accurate) and treated with purified anti-mouse CD32/CD16 Fc receptor (Pharmingen, 01241 D) to block non-specific binding to Fc receptors, stained with antibodies and analyzed on a FACStar$^{PLUS}$ (Becton Dickinson, CELLQuest software). Antibodies used: allophycocyanin (APC) anti-B220 (Pharmingen, 01129A); biotin anti-human IgM (Pharmingen, 08072D); biotin anti-mouse IgM (Pharmingen, 02202D); fluoroscein isothiocyanate (FITC) goatF(ab')$_2$ anti-human IgD (Southern Biotechnology, 2032-02); FITC$_b$ anti-mouse IgD$^a$ (Pharmingen, 05064D); FITC anti-mIgD$^b$ (Pharmingen, 05074D); FITC anti-mouse λ (Pharmingen, 02174D); PE anti-human κ (Pharmingen, 08175A); PE anti-mouse κ (Pharmingen, 02155A.) RED613™-streptavidin (GibcoBRL, 19541-010) was used to detect biotinylated antibodies.

Imminization and Hybridoma Generation:

XenoMice (8 to 10 weeks old) were immunized intraperitoneally with 25 μg of recombinant human IL-8 or with 5 μg TNF-α (Biosource International) emulsified in complete Freund's adjuvant for the primary immunization and in incomplete Freund's adjuvant for the additional immunizations carried out at two week intervals. For EGFR immunization, XenoMice were immunized intraperitoneally with $2 \times 10^7$ A431 (ATCC CRL-7907) cells resuspended in phosphate buffered saline (PBS). This dose was repeated three times. Four days before fusion, the mice received a final injection of antigen or cells in PBS. Spleen and lymph node lymphocytes from immunized mice were fused with the non-secretory myeloma NSO-bcl2 line (Ray and Diamond, 1994), and were subjected to HAT selection as previously described (Galfre and Milstein, 1981).

ELISA Assay:

ELISA for determination of antigen-specific antibodies in mouse serum and in hybridoma supernatants were carried out as described (Coligan et al., 1994) using recombinant human IL-8 and TNF-α and affinity-purified EGFR from A431 cells (Sigma, E-3641) to capture the antibodies. The concentration of human and mouse immunoglobulins were determined using the following capture antibodies: rabbit anti-human IgG (Southern Biotechnology, 6145-01), goat anti-human Igκ (Vector Laboratories, AI-3060), mouse anti-human IgM (CGI/ATCC, HB-57), for human γ, κ, and μ Ig, respectively, and goat anti-mouse IgG (Caltag, M 30100), goat anti-mouse Igκ (Southern Biotechnology, 1050-01), goat anti-mouse IgM (Southern Biotechnology, 1020-01), and goat anti-mouse λ (Southern Biotechnology, 1060-01) to capture mouse γ, κ, μ, and λ Ig, respectively. The detection antibodies used in ELISA experiments were goat anti-mouse IgG-HRP (Caltag, M-30107), goat anti-mouse Igκ-HRP (Caltag, M 33007), mouse anti-human IgG2-HRP (Southern Biotechnology, 9070-05), mouse anti-human IgM-HRP (Southern Biotechnology, 9020-05), and goat anti-human kappa-biotin (Vector, BA-3060). Standards used for quantitation of human and mouse Ig were: human IgG$_2$ (Calbiochem, 400122), human IgM$_\kappa$ (Cappel, 13000), human IgG$_2$κ (Calbiochem, 400122), mouse IgGκ (Cappel 55939), mouse IgM$_\kappa$ (Sigma, M-3795), and mouse IgG$_3$λ (Sigma, M-9019).

Determination of Affinity Constants of Fully Human Mabs by BIAcore:

Affinity measurement of purified human monoclonal antibodies, Fab fragments, or hybridoma supernatants by plasmon resonance was carried out using the BIAcore 2000 instrument, using general procedures outlined by the manufacturers.

Kinetic analysis of the antibodies was carried out using antigens immobilized onto the sensor surface at a low density: human IL-8-81 RU, soluble EGFR purified from A431 cell membranes (Sigma, E-3641)-303 RU, and TNF-α-107 RU (1,000 RU correspond to about 1 ng/mm$^2$ of immobilized protein). The dissociation (kd) and association (ka) rates were determined using the software provided by the manufacturers, BIAevaluation 2.1.

Affinity Measurement by Radioimmunoassay:

$^{125}$I-labeled human IL-8 ($1.5 \times 10^{-11}$ M or $3 \times 10^{-11}$ M) was incubated with purified anti-IL-8 human antibodies at varying concentrations ($5 \times 10^{-13}$ M to $4 \times 10^{-9}$ M) in 200 μl of PBS with 0.5% BSA. After 15 hrs. incubation at room temperature, 20 μl of Protein A Sepharose CL-4B in PBS (1/1, v/v) was added to precipitate the antibody-antigen complex. After 2 hrs. incubation at 4° C., the antibody-$^{125}$I-IL-8 complex bound to Protein A Sepharose was separated from free $^{125}$I-IL-8 by filtration using 96-well filtration plates (Millipore, Cat. No. MADVN65), collected into scintillation vials and counted. The concentration of bound and free antibodies was calculated and the binding affinity of the antibodies to the specific antigen was obtained using Scatchart analysis (2).

Receptor Binding Assays:

The IL-8 receptor binding assay was carried out with human neutrophils prepared either from freshly drawn blood or from buffy coats as described (Lusti-Marasimhan et al., 1995). Varying concentrations of antibodies were incubated with 0.23 nM [$^{125}$I]IL-8 (Amersham, IM-249) for 30 min at 4° C. in 96-well Multiscreen filter plates (Millipore, MADV N6550) pretreated with PBS binding buffer containing 0.1% bovine serum albumin and 0.02% NaN$_3$ at 25° C. for 2 hours. $4 \times 10^5$ neutrophils were added to each well, and the plates were incubated for 90 min at 4° C. Cells were washed 5 times with 200 μl of ice-cold PBS, which was removed by aspiration. The filters were air-dried, added to scintillation fluid, and counted in a scintillation counter. The percentage of specifically bound [$^{125}$I]IL-8 was calculated as the mean cpm detected in the presence of antibody divided by cpm detected in the presence of buffer only.

Binding assays for TNF receptor were performed in a similar manner as the IL-8 assays described above. However, the human monocyte line U937 was utilized instead of the neutrophil line used in connection with the IL-8 assays. Antibodies were preincubated with 0.25 nM [$^{125}$I]TNF (Amersham, IM-206). $6 \times 10^5$ U937 cells were placed in each well.

The EGF receptor binding assay was carried out with A431 cells ($0.4 \times 10^6$ cells per well) which were incubated with varying concentrations of antibodies in PBS binding buffer for 30 minutes at 4° C. 0.1 nM [$^{125}$I]EGF (Amersham, IM-196) was added to each well, and the plates were incubated for 90 min at 4° C. The plates were washed five times, air-dried and counted in a scintillation counter. Anti-EGFR mouse antibodies 225 and 528 (Calbiochem) were used as controls.

Repertoire Analysis of Human Ig Transcripts Expressed in XenoMice and Their Derived Human Mabs:

Poly(A)$^+$ mRNA was isolated from spleen and lymph nodes of unimmunized and immunized XenoMice using a Fast-Track kit (Invitrogen). The generation of random primed cDNA was followed by PCR. Human $V_H$ or human $V_\kappa$ family specific variable region primers (Marks et. al., 1991) or a universal human $V_H$ primer, MG-30 (CAGGT-GCAGCTGGAGCAGTCIGG) (SEQ ID NO: 78) was used in conjunction with primers specific for the human Cμ (hμP2) or Cκ (hκP2) constant regions as previously described (Green et al., 1 994), or the human γ2 constant region MG-40d; 5'-GCTGAGGGAGTAGAGTCCT-GAGGA-3' (SEQ ID NO: 79). PCR products were cloned into pCRII using a TA cloning kit (Invitrogen) and both strands were sequenced using Prism dye-terminator sequencing kits and an ABI 377 sequencing machine. Sequences of human Mabs-derived heavy and kappa chain transcripts were obtained by direct sequencing of PCR products generated from poly(A$_+$) RNA using the primers described above. All sequences were analyzed by alignments to the "V BASE sequence directory" (Tomlinson et al., MRC Centre for Protein Engineering, Cambridge, UK) using MacVector and Geneworks software programs.

Preparation and Purification of Antibody Fab Fragments:

Antibody Fab fragments were produced by using immobilized papain (Pierce). The Fab fragments were purified with a two step chromatographic scheme: HiTrap (Bio-Rad) Protein A column to capture Fc fragments and any undigested antibody, followed by elution of the Fab fragments retained in the flow-through on strong cation exchange column (PerSeptive Biosystems), with a linear salt gradient to 0.5 M NaCl. Fab fragments were characterized by SDS-PAGE and MALDI-TOF MS under reducing and non-reducing conditions, demonstrating the expected ~50 kD unreduced fragment and ~25 kDa reduced doublet. This result demonstrates the intact light chain and the cleaved heavy chain. MS under reducing conditions permitted the unambiguous identification of both the light and cleaved heavy chains since the light chain mass can be precisely determined by reducing the whole undigested antibody.

EXAMPLES

The following examples, including the experiments conducted and results achieved are provided for illustrative purposes only and are not to be construed as limiting upon the present invention.

Example 1

Reconstruction of Human Heavy Chain Loci on YACs

In accordance with the present invention, the strategy that we utilized to reconstruct the human heavy chain and human kappa light chain variable regions was to, first, screen human-YAC libraries for YACs that spanned the large (megabase-sized) human Ig loci and, second, to recombine YACs spanning such regions into single YACs containing the desired loci predominantly in germline configuration.

The above, stepwise, YAC recombination scheme exploited the high frequency of meiotic-induced homologous recombination in yeast and the ability to select the desired recombinants by the yeast markers present on the vector arms of the recombined YACs (See FIG. 1, and Green et al., supra.; see also Silverman et al., 1990 and denDunnen et al., 1992).

In connection with our strategy, we identified four YACs, 1H (240 kb), 2H (270 kb), 3H (300 kb), and 4H (340 kb), which spanned about 830 kb, out of the about 1000 kb, of the human heavy chain variable region on chromosome 14q. YACs 1H, 2H, 3H, and 4H were used for reconstruction of the locus (See FIG. 1A). Pulsed Field Gel Electrophoresis (PFGE) and Southern blot analysis confirmed the YACs to be in intact, germline configuration, with the exception of 150 kb at the 3' end of YAC 2H which contained certain non-IgH sequences (See FIG. 1; Matsuda et al., 1990). YAC 1H, the YAC that was previously introduced into our first generation XenoMouse™ (Green et al., supra.; Mendez et al., 1995), is comprised of the human $C_\delta$, $C_\mu$, $J_H$, and $D_H$ regions and the first 5 $V_H$ genes in germline configuration. The other three YACs cover the majority of the $V_H$ region, from $V_H2$-5 to $V_H3$-65, thus contributing approximately an additional 61 different $V_H$ genes. Prior to recombination, YAC 4H was retrofitted with an HPRT selectable marker. Through utilization of the overlapping sequences contained on the YACs, the four YACs (1H, 2H, 3H, and 4H) were recombined in yeast by a stepwise recombination strategy (See FIG. 1A). Such recombination strategy generated a 980 kb recombinant YAC (See FIG. 1). Analysis of the YAC by PFGE and Southern blot analysis confirmed the presence of the human heavy chain locus from the $C_\delta$ region to 20 kb 5' of the $V_H3$-65 gene in germline configuration. No apparent deletions or rearrangements were observed.

The YAC acentric arm was targeted with a vector bearing the complete human γ2 constant region, mouse 3' enhancer, and the neomycin resistance gene, to yield the final 1020 kb heavy chain YAC, yH2. YAC yH2 contained the majority of the human variable region i.e., 66 out of the 82 $V_H$ genes, complete $D_H$ (32 genes), and $J_H$ (6 genes) regions and three different constant regions (Cμ, Cδ, and Cγ) with their corresponding regulatory sequences (See FIG. 1A). This was the heavy chain construct utilized for the production of our XenoMouse II strains.

Example 2

Reconstruction of Human Kappa Light Chain Loci on YACs

Figure 1B:
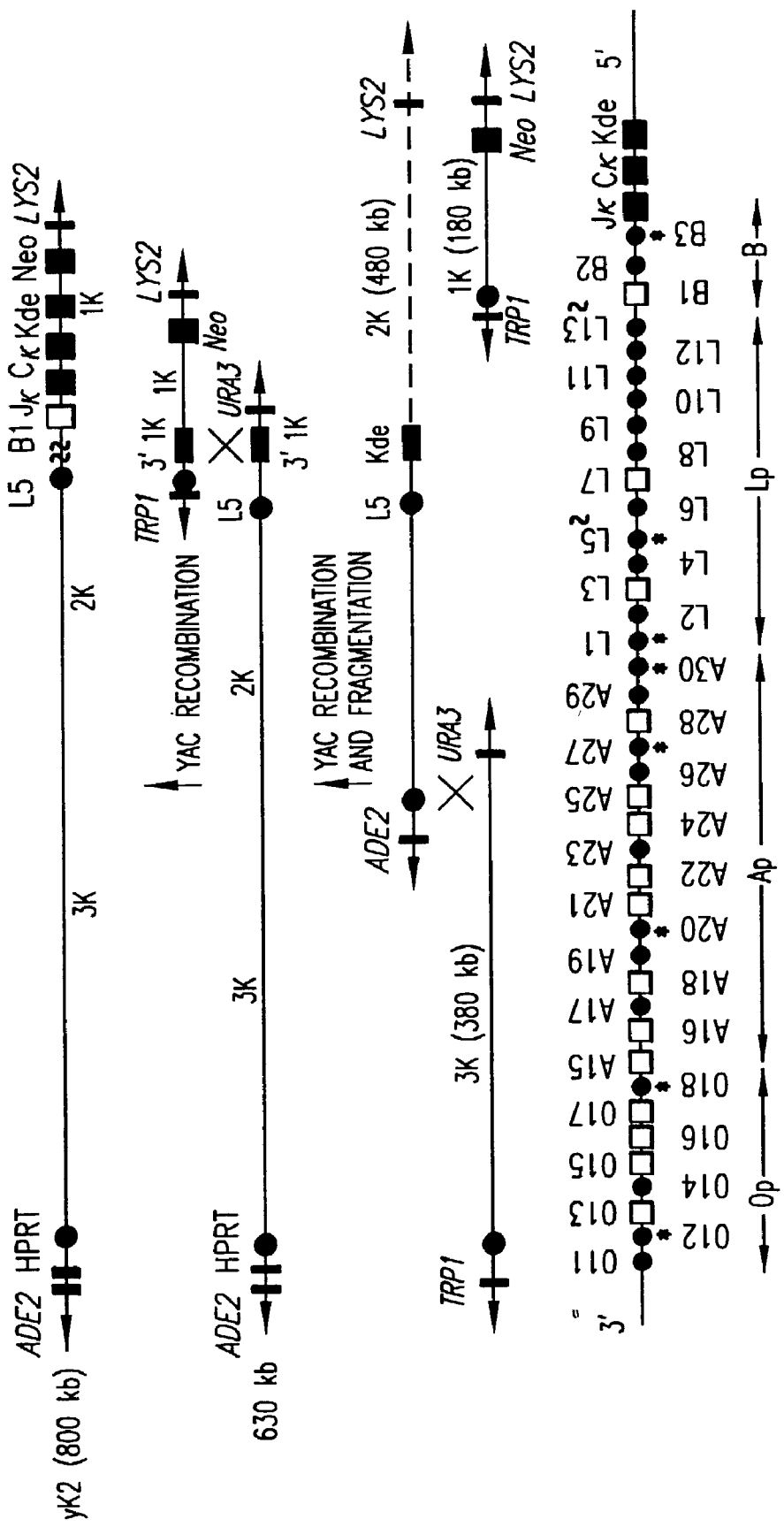
Figure 2A:
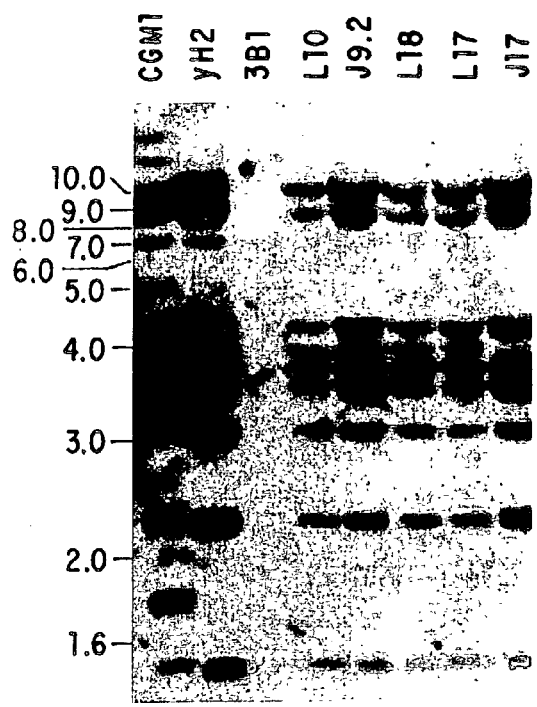
Figure 2C:
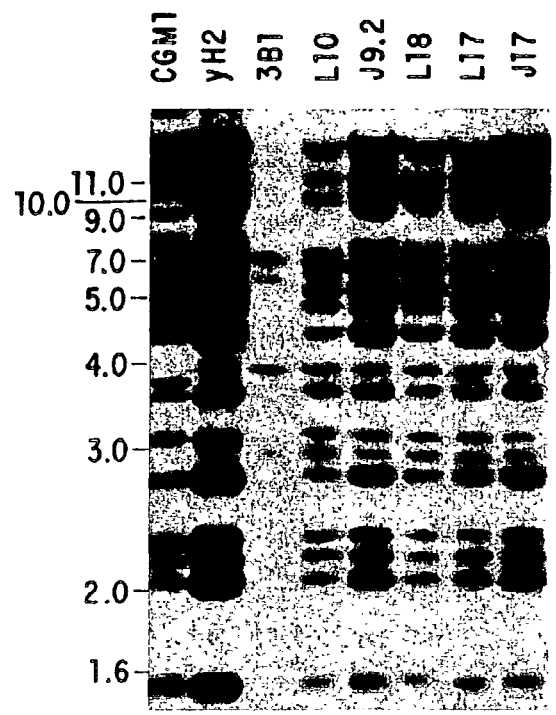
Figure 2B:
Figure 2D:
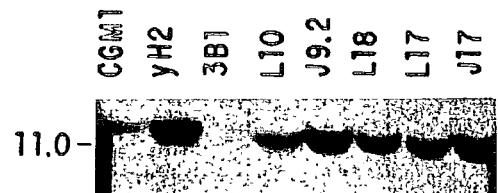
Figure 2E:
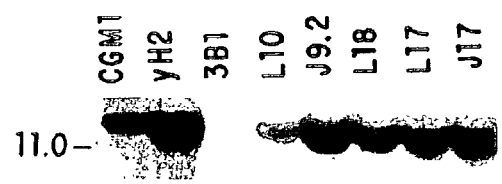
Figure 2F:
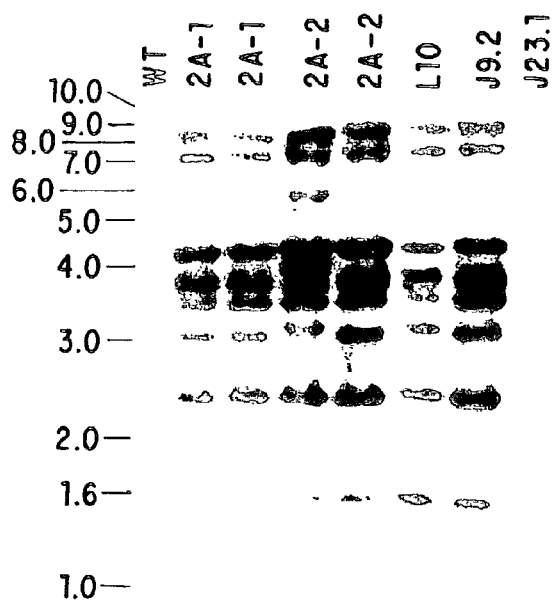
Figure 2H:
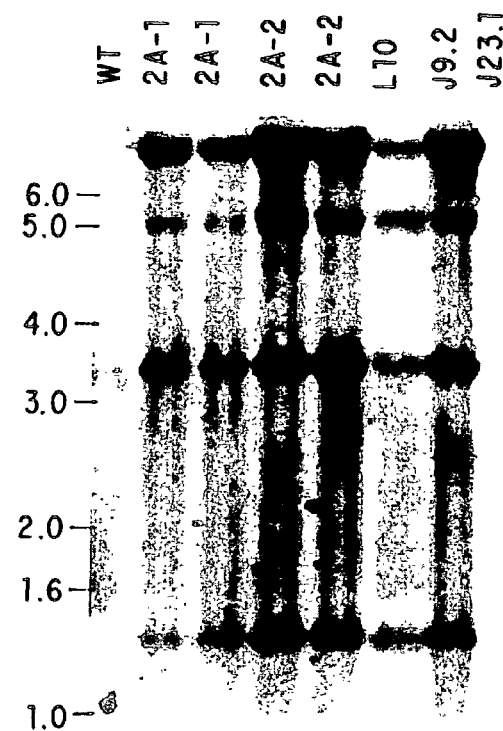
Figure 2G:
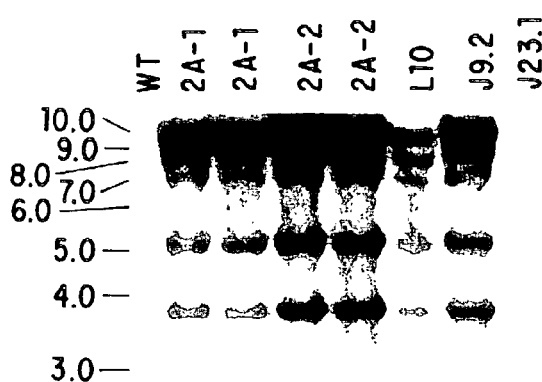
Figure 2I:
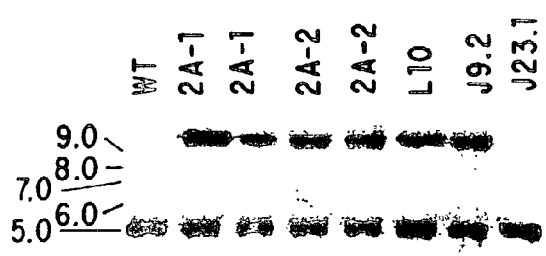
Figure 3A:
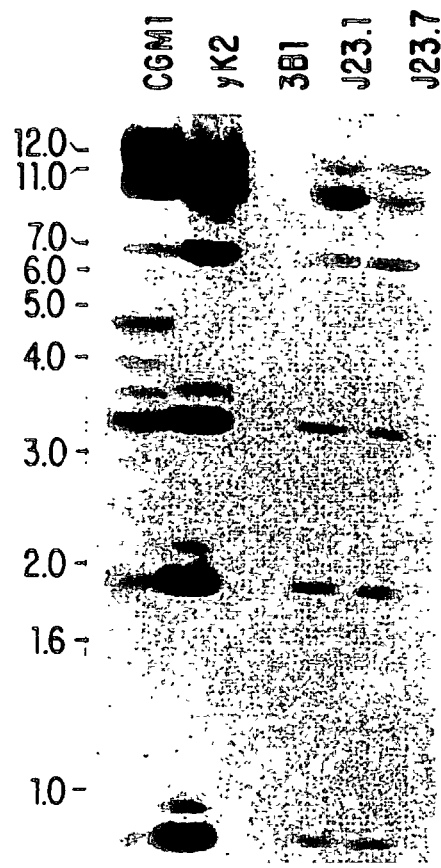
Figure 3B:
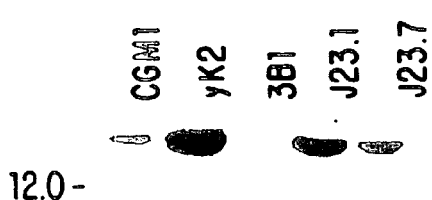
Figure 3C:
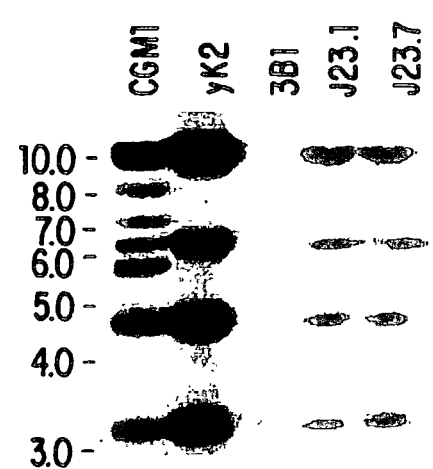
Figure 3D:
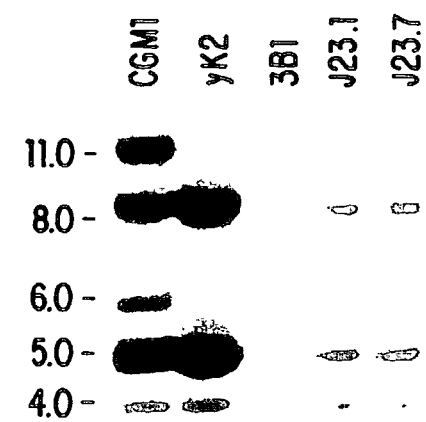
Figure 3E:
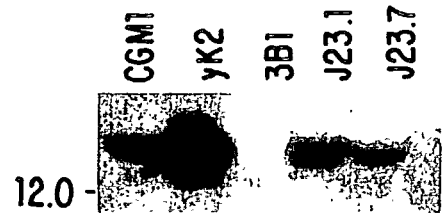
Figure 4A:
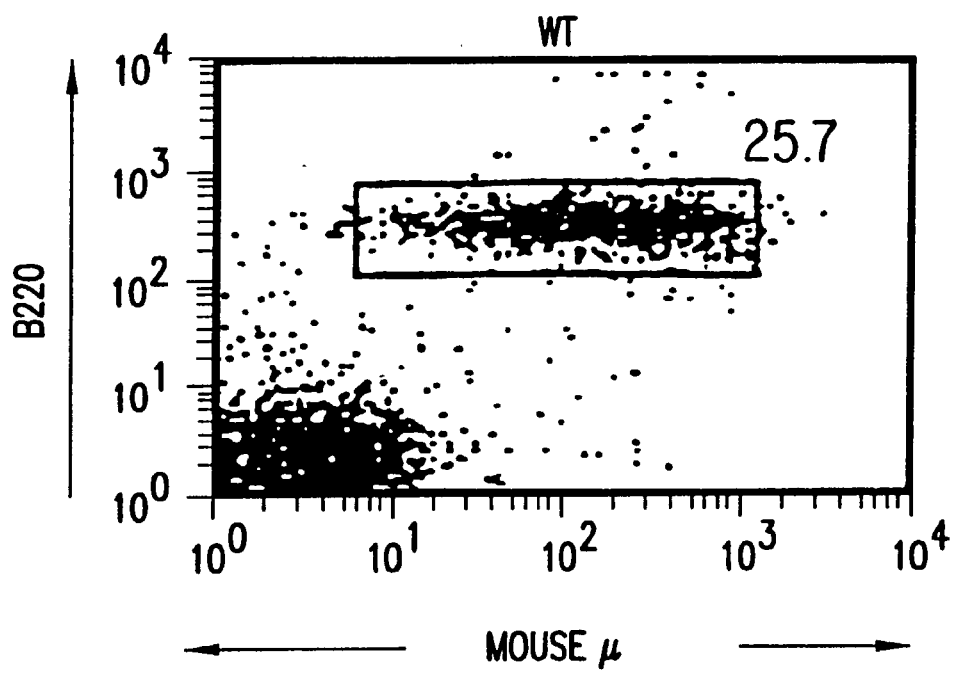
Figure 4B:
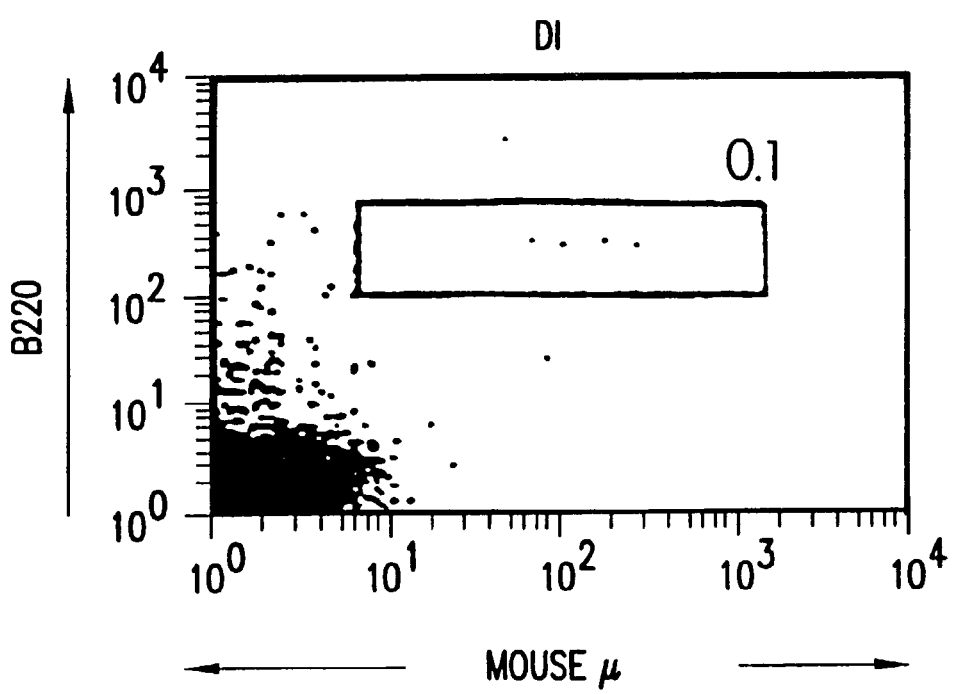
Figure 4C:
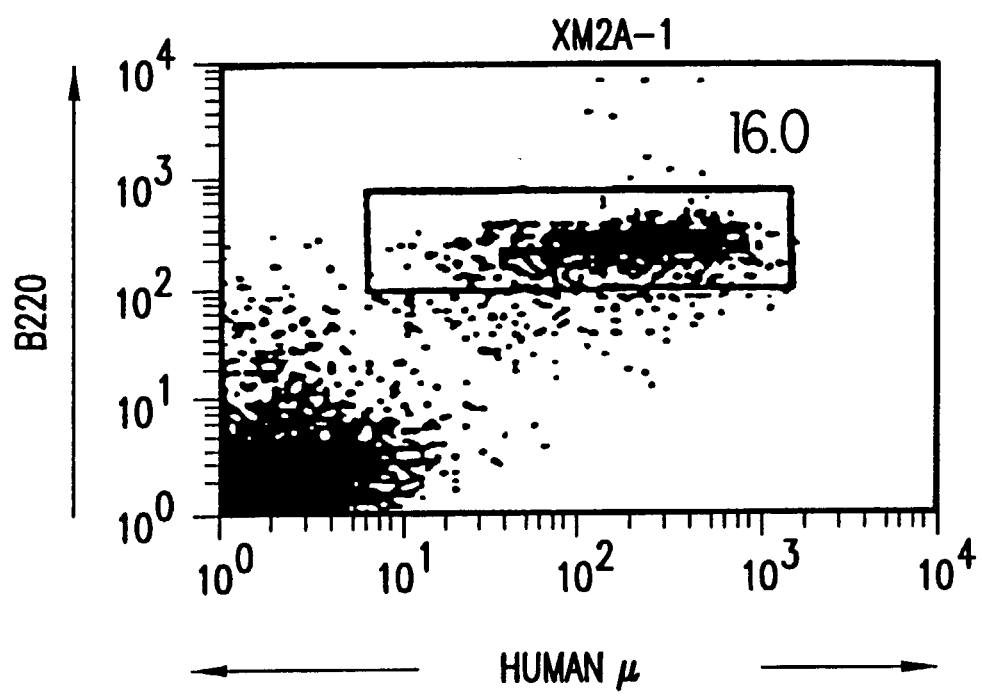
Figure 4D:
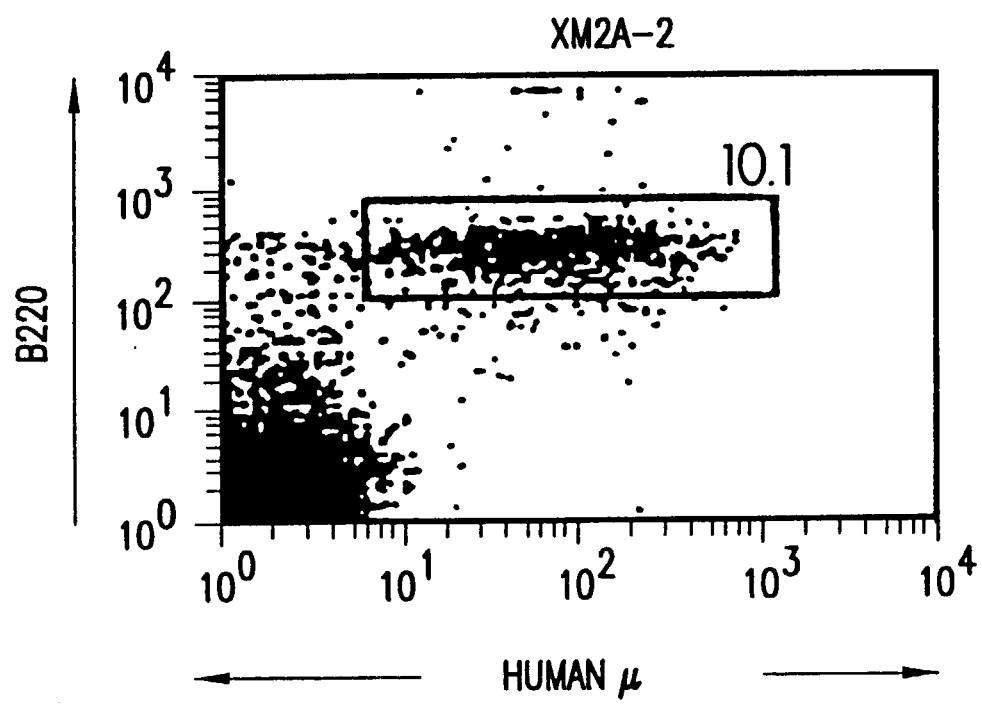
Figure 4E:
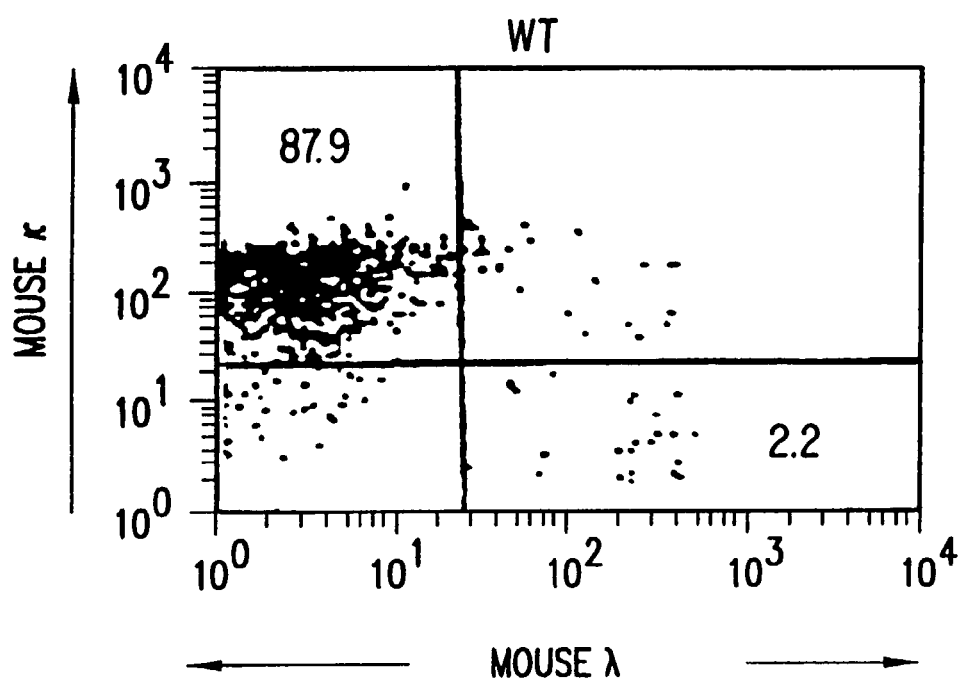
Figure 4F:
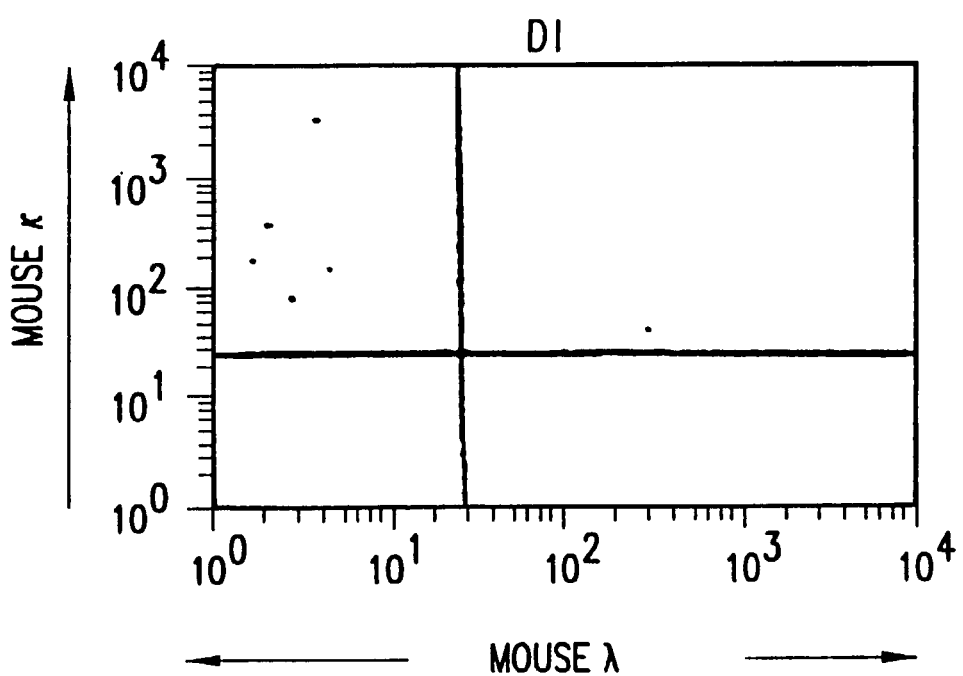
Figure 4G:
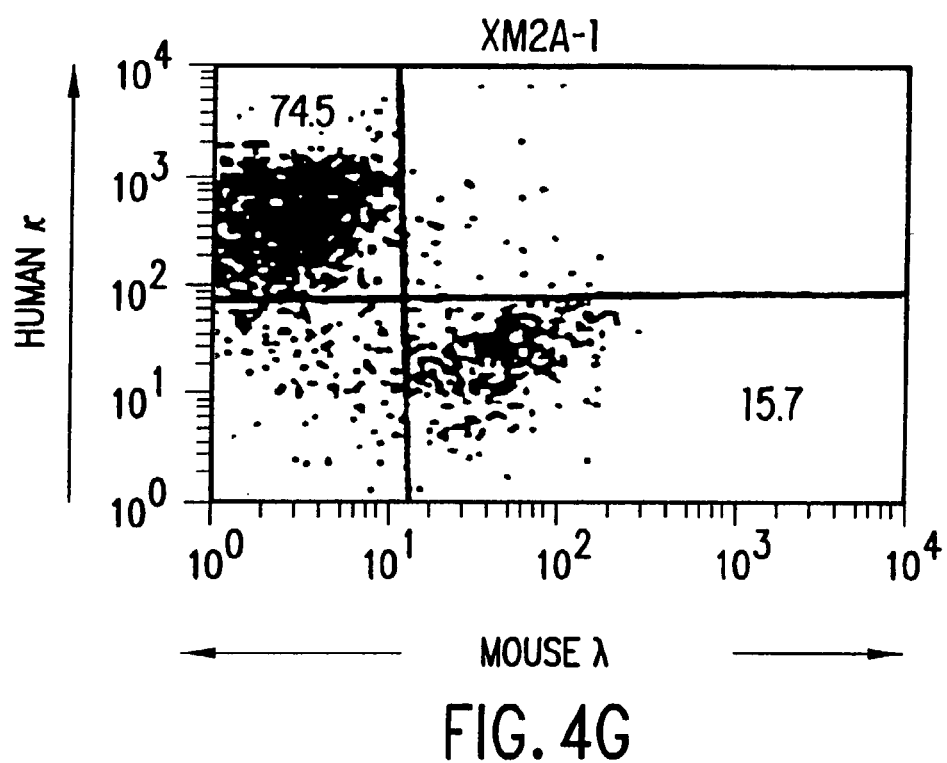
Figure 4H:
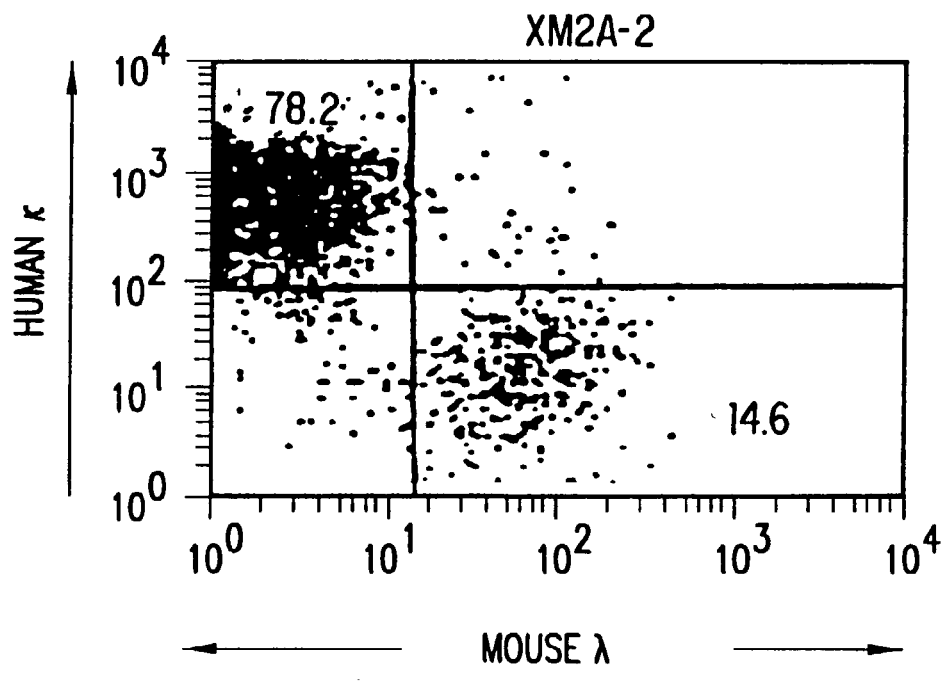
Figure 4I:
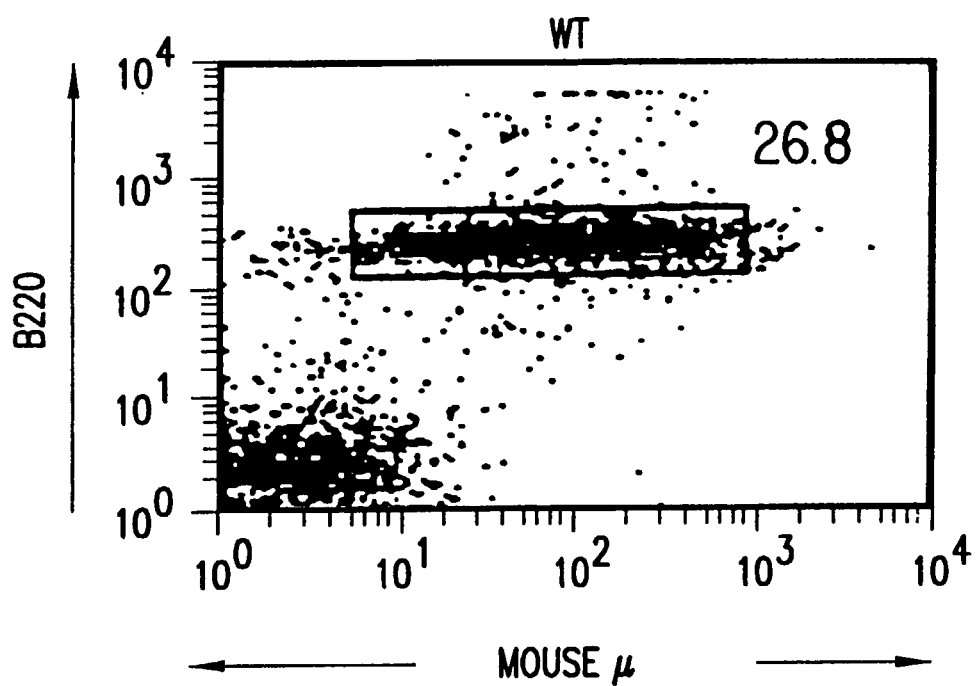
Figure 4J:
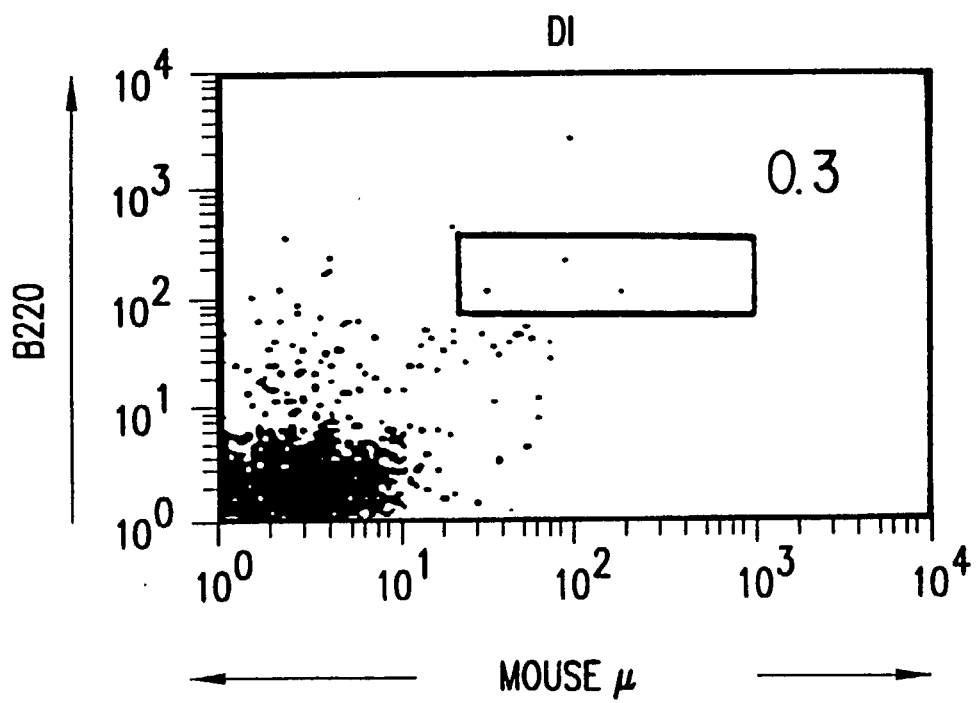
Figure 4K:
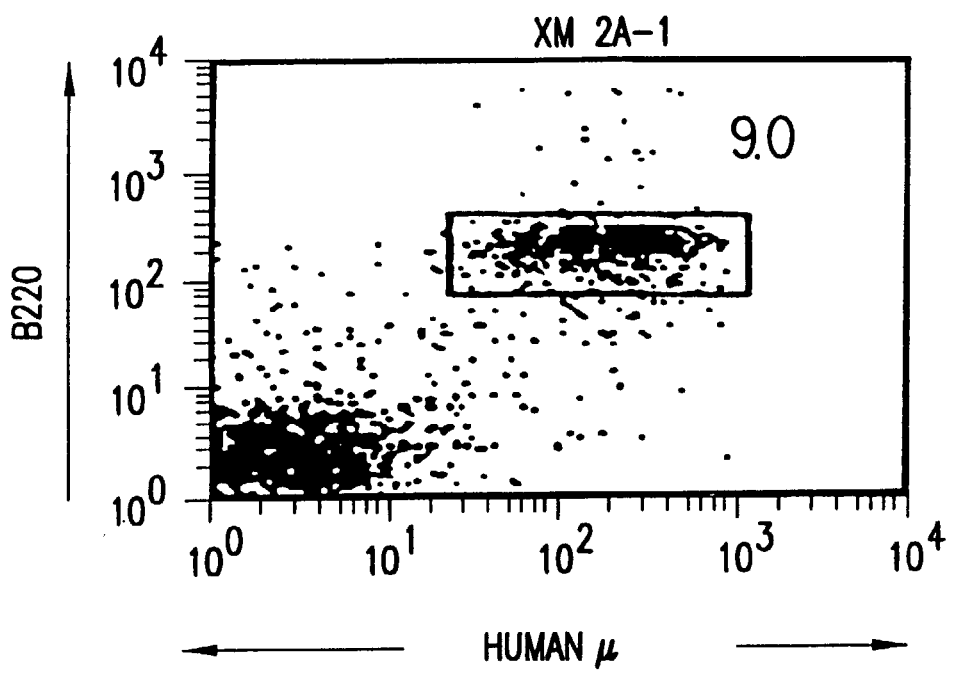
Figure 4L:
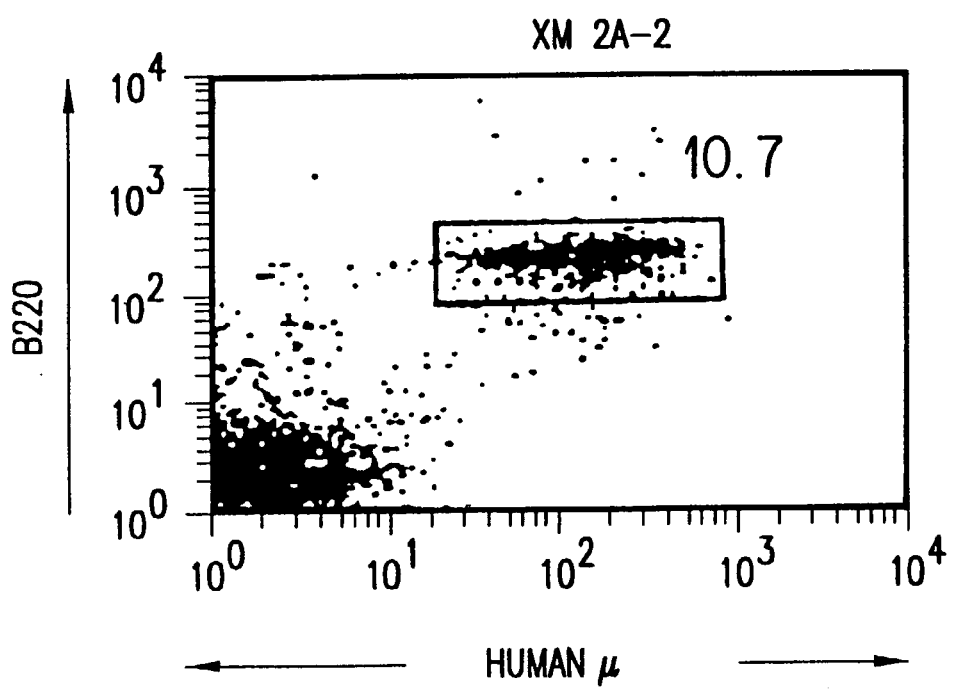
Figure 4M:
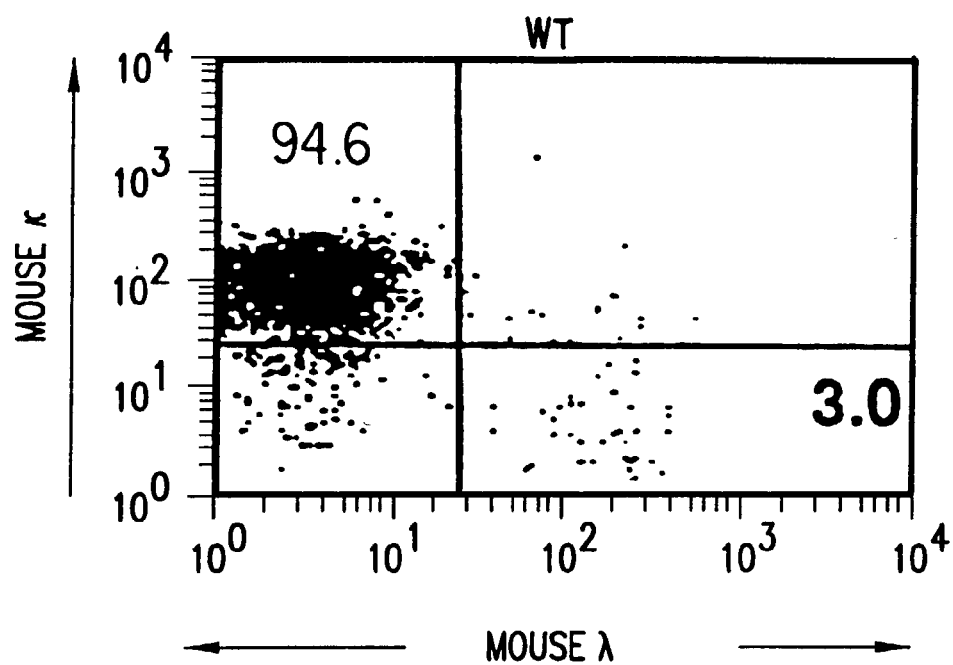
Figure 4N:
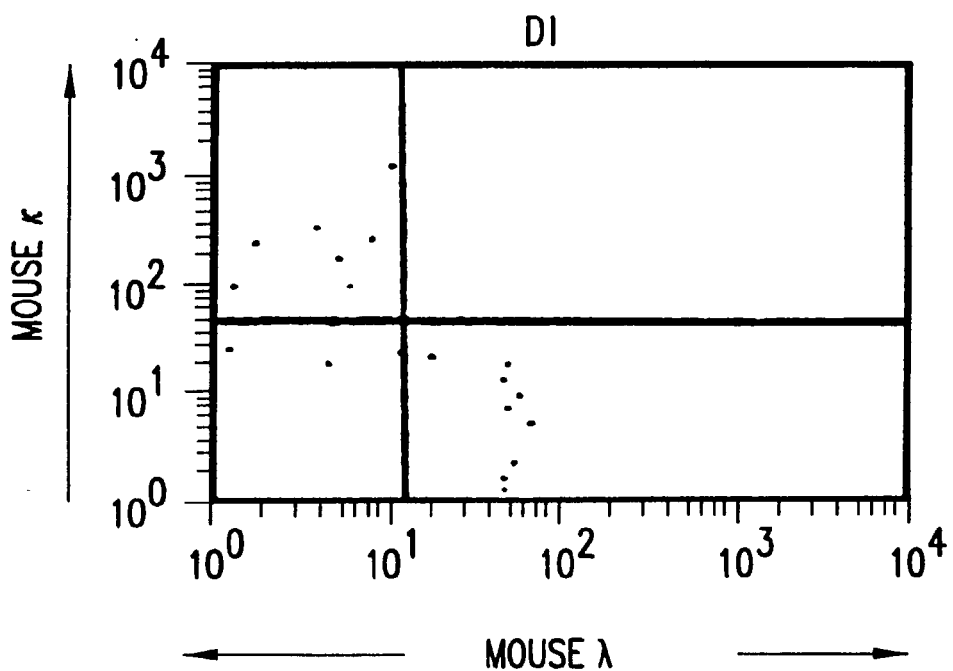
Figure 4O:
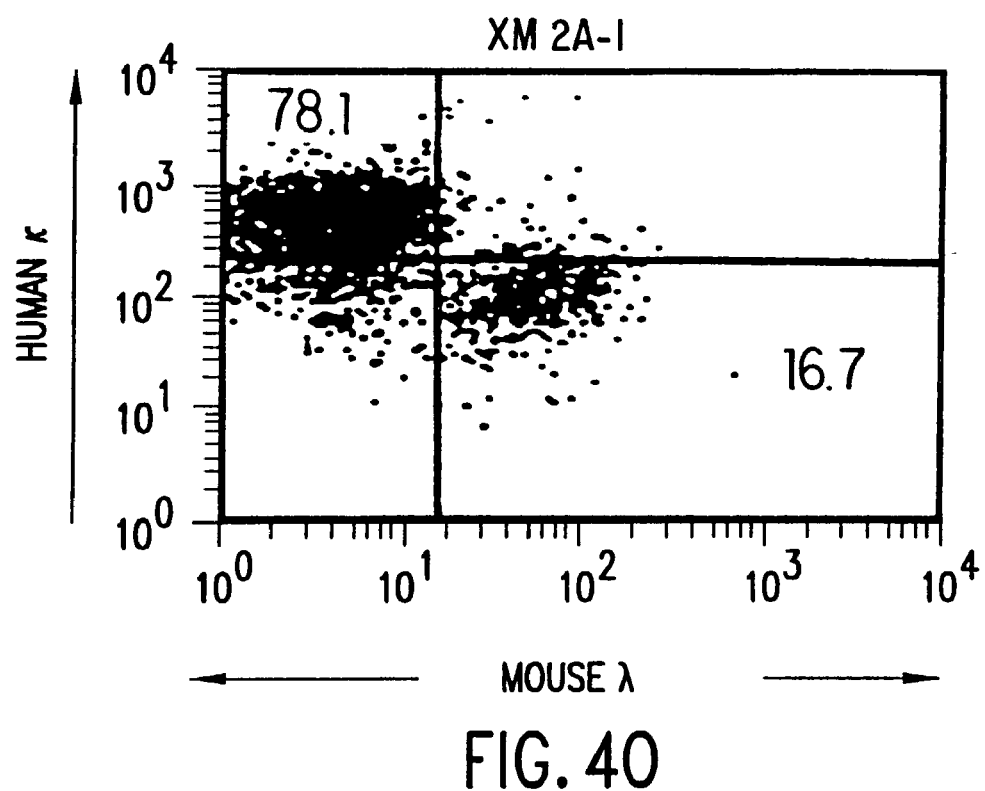
Figure 4P:
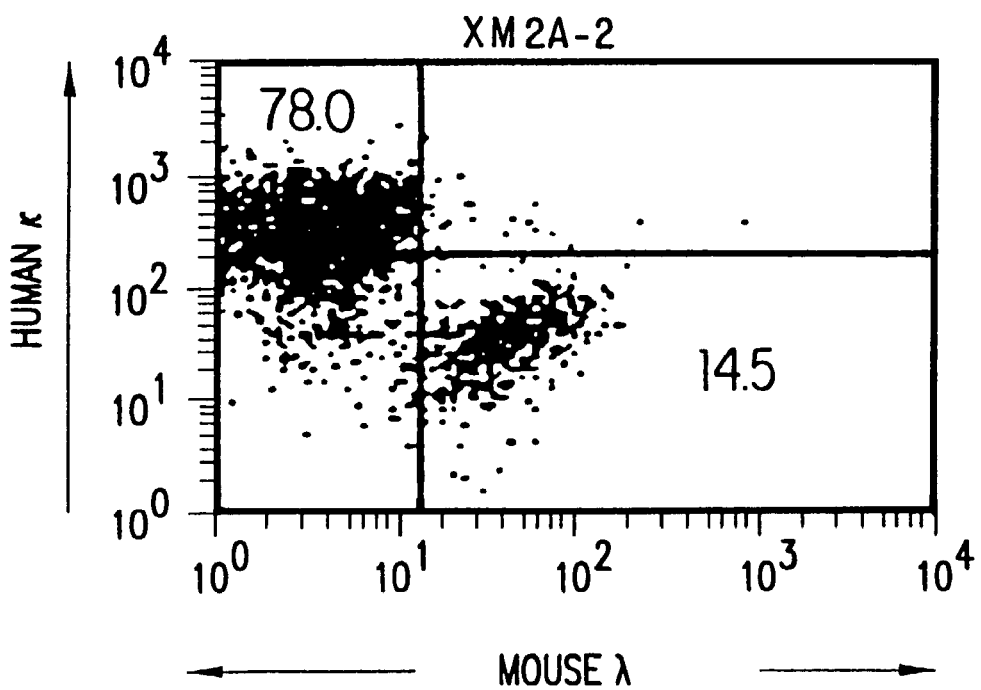
Figure 4Q:
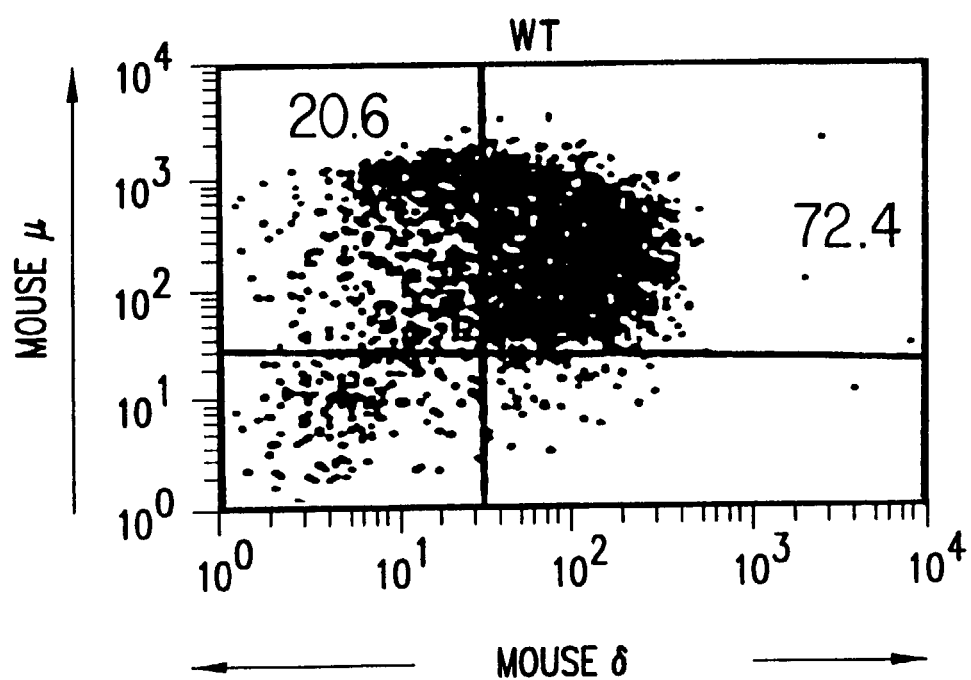
Figure 4R:
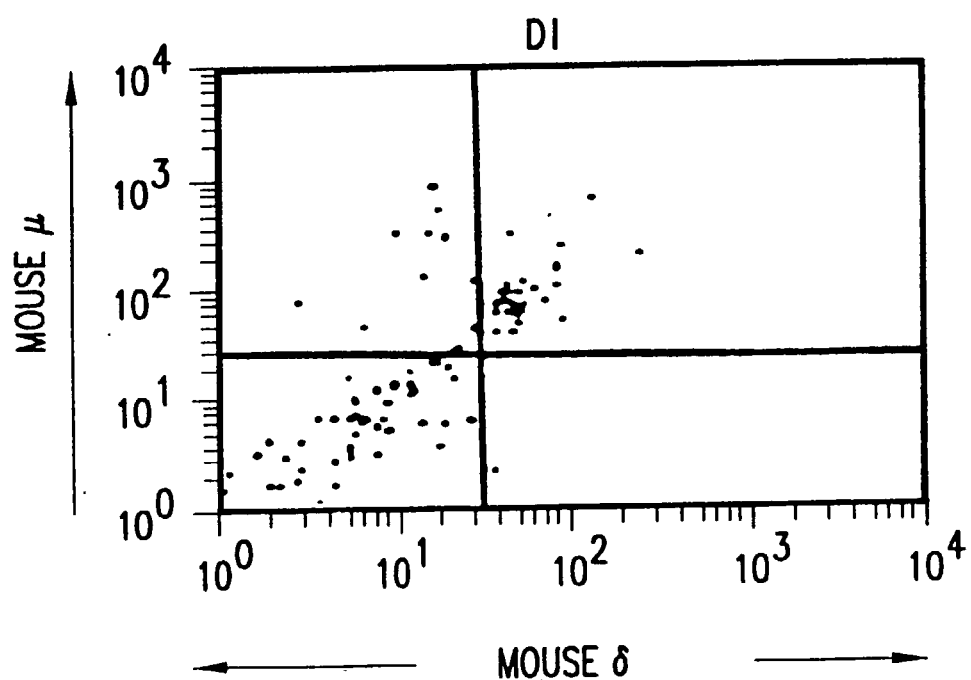
Figure 4S:
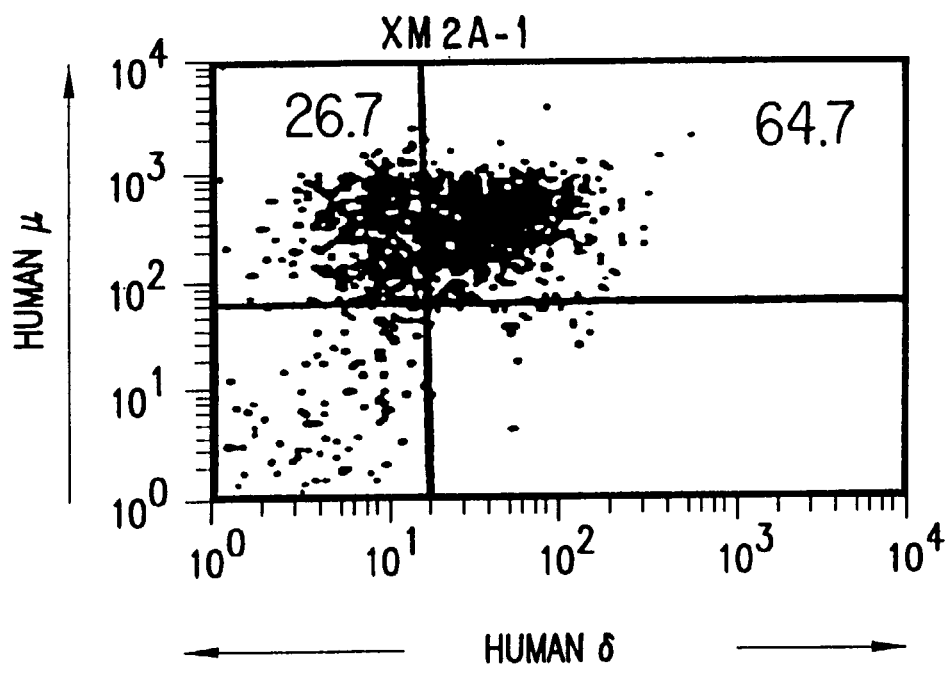
Figure 4T:
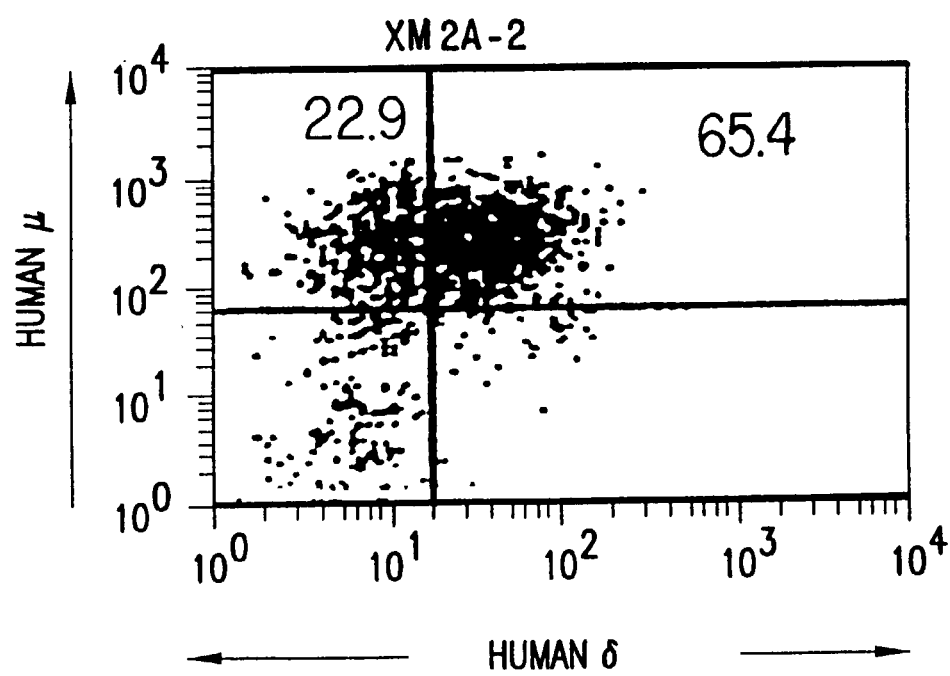

A similar stepwise recombination strategy was utilized for reconstruction of the human kappa light chain locus. Three YACs were identified that spanned the human kappa loci. The YACs were designated 1 K, 2K and 3K. YAC 1K, which had a length of approximately 180 kb, had previously been introduced into our first generation XenoMouse™. Such YAC contained the kappa deleting element, (Kde), the kappa 3' and intronic enhancers, $C_\kappa$, $J_\kappa$, and the three $V_\kappa$ genes on the B cluster (Green et al., 1994; Mendez et al., 1995). YAC 2K (approximately 480 kb), and 3K (approximately 380 kb) together encompass most of the kappa chain proximal variable region on chromosome 2p. A deletion of approximately 100 kb spans the L13–L5 region (FIG. 1B; Huber et al., 1993). Inasmuch as the kappa distal region duplicates the proximal region, and as the proximal $V_\kappa$ genes are the ones most commonly utilized humans (Weichold et al., 1993; Cox et al., 1994), the proximal region was the focus of our reconstruction strategy (FIG. 1B). Through homologous recombination of the three YACS, an 800 kb recombinant YAC, yK2, was recovered. The size and integrity of the recombinant YAC was confirmed by PFGE and Southern blot analysis. Such analysis demonstrated that it covered the proximal part of the human kappa chain locus, with 32 $V_\kappa$ genes in germline configuration except for the described deletion in the Lp region (FIG. 1B). yK2 centric and acentric arms were modified to contain the HPRT and neomycin selectable markers, respectively, as described (Materials and Methods). This was the kappa light chain construct utilized for the production of our XenoMouse II strains.

The YACs described herein, yH2 and yK2, represent the first megabase-sized reconstructed human Ig loci to contain the majority of the human antibody repertoire, predominantly in germline configuration. This accomplishment further confirmed homologous recombination in yeast as a powerful approach for successful reconstruction of large, complex, and unstable loci. The selection of stable YAC recombinants containing large portions of the Ig loci in yeast provided us with the human Ig fragments required to equip the mice with the human antibody repertoire, constant regions, and regulatory elements needed to reproduce human antibody response in mice.

Example 3

Introduction of yH2 and yK2 YACs into ES Cells

In accordance with our strategy, we introduced the YACs, yH2 and yK2, into mouse embryonic stem (ES) cells. Once ES cells containing the YAC DNA were isolated, such ES cells were utilized for the generation of mice through appropriate breeding.

In this experiment, therefore, YACs yH2 and yK2, were introduced into ES cells via fusion of YAC-containing yeast spheroplasts with HPRT-deficient E14.TG3B1 mouse ES cells as previously described (Jakobovits et al., 1993a; Green et al., 1994). HPRT-positive ES cell clones were selected at a frequency of 1 clone/15–20×10$^6$ fused cells and were analyzed for YAC integrity by Southern and CHEF blot analyses (FIGS. 2A–2E).

Seven of thirty-five ES cell clones (referred to as L10, J9.2, L17, L18, J17, L22, L23) derived from ES cell fusion with yH2-containing yeast were found to contain all expected EcoRI and BamHI yH2 fragments detected by probes spanning the entire insert: mouse 3' enhancer, human intronic enhancer, human $C_\gamma 2$, $C_\delta$, and $C_\mu$ constant regions, $D_H$, $J_H$ and all the different $V_H$ families: $V_H 1$, $V_H 2$, $V_H 3$, $V_H 4$, $V_H 5$, and $V_H 6$ (data shown for 5 clones in FIGS. 2A–2E). CHEF analysis further confirmed that these clones, which represent 20% of all clones analyzed, contain the entire intact yH2 YAC with no apparent deletions or rearrangements (data not shown).

ES cell clones derived from the fusion of yK2-containing yeast were similarly analyzed for YAC integrity, using probes specific for the human Kde, kappa 3' and intronic enhancers, $C_K$, $J_H$, and all of the different $V_K$ families: $V_K I$, $V_K II$, $V_K III$, $V_K IV$, $V_{VI}$. Twenty clones of the sixty clones had intact and unaltered YAC, which represent 30% of total clones analyzed (data shown for two ES clones in FIGS. 3A–3E). Varying amounts of yeast genomic sequences were detected in yH2 and yK2-ES cell clones (data not shown).

These results are the first demonstration of introduction of megabase-sized constructs encompassing reconstructed human loci, predominantly in germline configuration, into mammalian cells. The relatively high frequency of intact YACs integrated into the mouse genome further validated the ES cell-yeast spheroplast fusion methodology as an effective approach for faithful introduction of large human genomic fragments into ES cells.

Example 4

Generation of XenoMouse II Strains

In order to generate mice from the YAC DNA containing ES cells, microinjection of blastocysts was conducted, followed by breeding. Thus, yH2- and yK2-bearing ES cell clones were expanded and microinjected into mouse C57BL/6J blastocysts (Green et al., 1994) and the chimeric males produced were evaluated for germline transmission. Offspring with transmitted YAC were identified by PCR analysis and the YAC integrity was confirmed by Southern blot analysis. In all transgenic mice analyzed the YAC was shown to be in intact form (FIGS. 2F–2I, 3F–3I). All seven microinjected yH2-ES clones and two out of eight yK2-ES clones were transmitted through the mouse germline.

In order to generate mice that produced human antibodies to the exclusion of endogenous antibodies, yH2- or yK2-transgenic mice were bred with double-inactivated (DI) mouse strains. The DI mouse strains are homozygous for gene targeted-inactivated mouse heavy and kappa chain loci and thus are deficient in antibody production (Jakobovits et al., 1993b; Green et al., 1994). Two of the yH2- transgenic mouse strains L10 and J9.2, and one of the yK2-transgenic mouse strains, J23.1, were bred with DI mice to generate mice bearing YACs on an homozygous inactivated mouse heavy and kappa chain background (yH2;DI, and yK2;DI). Each of the yH2;DI transgenic strains were bred with the yK2;DI transgenic strain to generate two XenoMouse II strains, 2A-1 (L10;J23.1;DI) and 2A-2 (J9.2;J23.1;DI), respectively, containing both heavy and light chain YACs on homozygous DI background. L10 is fully homozygous and J9.2 and J23.1 are in the process of being successfully bred to homozygosity.

The integrity of the human heavy and kappa chain YACs in XenoMouse II strains was confirmed by Southern blot analysis. As shown in FIG. 2 and FIG. 3, in both XenoMouse strains analyzed, yH2 and yK2 were transmitted unaltered through multiple generations with no apparent deletions or rearrangements.

Example 5

B-Cell Development and Human Antibody Production by XenoMouse II Mice

In order to further characterize the XenoMouse II strains, we studied their B-cell development and their production of human antibodies. Reconstitution of B-cell development and antibody production in XenoMouse II strains by yH2 and yK2 YACs was evaluated by flow cytometry and ELISA. In contrast to DI mice, which completely lack mature B-cells, XenoMouse II manifested essentially normal B-cell development with the mature B-cell population in the blood totaling over 50% of the level seen in wild type race (FIGS. 4A–4H). All B-cells were shown to express human IgM and high levels of B220 (human IgM+/B220$^{hi}$), with 60% of this population also expressing human IgD. Similar results were obtained from analysis of XenoMouse spleen and lymph nodes (not shown). These results correlate well with the characteristics of mature B-cells in wild type mice, indicating proper B-cell maturation in XenoMouse.

The majority of XenoMouse B-cells (75–80%) expressed exclusively human kappa (κ)light chain, whereas only about 15% expressed mouse lambda (λ) light chain (FIGS. 4A–4I). This light chain distribution ratio (hκ/mλ 75:15) is comparable to that observed in wild type mice, indicating a mouse-like regulation of light chain utilization. In contrast, XenoMouse I, as described in Green et al., 1994, showed a ratio of hκ/mλ 55:45 (data not shown). Similar observations were made for B-cells from spleen (FIGS. 4I–4T) and lymph nodes (not shown), indicating that most of XenoMouse II's B cells produced exclusively fully human antibodies. Levels of mλ-expressing B-cells were reduced from 15% to 7% in XenoMouse II strains homozygous for yK2 (data not shown).

Example 6

Generation of L6 Strain

The L6 strain of mice were generated identically to the process described above in connection with the generation of the XenoMouse II strains. However, owing to a deletion event during the generation of the L6 ES cell line, the ES cell line, and, subsequently, the L6 mouse evolved without a portion of the sequence distal to Cδ, thus, eliminating the Cγ constant region and its regulatory sequences. Following completion of breeding, the L6 mice will contain the entire yK2 construct and the entire yH2 construct, except for the missing Cγ constant region.

Example 7

Human Antibody Production

Expression of human Cμ, Cγ2, and κ light chains were detected in unimmunized XenoMouse II sera at maximal levels of 700, 600, and 800 μg/ml, respectively. To determine how these values compared to wild-type, we measured maximal levels of mouse Cμ, Cγ2, and κ light chains in C57BL/6J x 129 mice kept under similar pathogen-free conditions. The values for Cv, Cγ2, and κ light chain in wild-type mice were 400, 2000, and 2000 μg/ml, respectively. Upon immunization, the human γ chain levels increased to approximately 2.5 mg/ml. The concentration of mouse λ was only 70 μg/ml, further confirming the preferential use of human kappa chain.

These findings confirmed the ability of the introduced human Ig YACs to induce proper Ig gene rearrangement and class switching and to generate significant levels of fully human IgM and IgG antibodies before and after immunization.

Example 8

A Diverse Human Antibody Repertoire in XenoMouse II

In order to further understand the reconstitution of the antibody repertoire in XenoMouse II strains, we challenged mice with several antigens, and prepared hybridoma cell lines secreting such antibodies. As will be understood, recapitulation of the human antibody response in mice requires diverse utilization of the different human variable genes contained on yH2 and yK2 YACs. The diversity of the human antibodies generated by XenoMouse II strains was determined by cloning and sequencing human heavy chain (μ and γ) and kappa light chain transcripts from XenoMouse lymph nodes. Based upon our data to date, sequence analysis demonstrates that XenoMouse II utilizes at least 11 out of the 37 functional $V_H$ genes present on yH2, eight different $D_H$ segments and three $J_H$ genes ($J_{H3}$, $J_{H4}$, $J_{H6}$) (Table III; $J_{H5}$ was also detected in connection with our sequencing antibodies from hybridomas). V-D-J sequences were linked to human μ or γ2 constant regions (not shown).

The $V_H$ genes utilized are widely distributed over the entire variable region and represent four out of the seven $V_H$ families (Table III). The predominant utilization of V genes from $V_{H3}$ and $V_{H4}$ families is similar to the $V_H$ usage pattern in adult humans, which is proportional to family size (Yamada et al. 1991; Brezinshek et al., 1995). The predominant usage of $J_{H4}$ is also reminiscent of that detected in human B-cells (Brezinshek et al., 1995). Addition of non-germline nucleotides (N-additions) at both V-D and D-J joinings, ranging from 1–12 bp, were also observed. Such N-additions produced complementary determining regions 3 (CDR3s) with lengths of from 8 to about 19 amino acid residues, which is very comparable to that observed in adults human B-cells (Yamada et al. 1991; Brezinshek et al., 1995). Such CDR3 lengths observed in the XenoMouse II are much longer than CDR3 lengths ordinarily observed in mice (Feeny, 1990).

A highly diverse repertoire was also found in the ten kappa chain transcripts sequenced. In addition to displaying 8 out of the 25 Vκ functional open reading frames (ORFs) present on yK2, all of the Jκ genes were detectable (Table IV). The different Vκ genes utilized were widely dispersed throughout yK2, representing all four major Vκ gene families. All VκJκ recombination products were linked properly to $C_κ$ sequences. The paucity of N-additions in our transcripts is in agreement with the greatly reduced terminal deoxynucleotide transferase activity at the stage of kappa chain rearrangement. The average CDR3 length of 9–10 amino acids that we observed in the kappa chain transcripts is identical to that observed in human B-cells (Marks et al., 1991).

In Tables III and IV below, repertoire analyses of human heavy and kappa light chain transcripts expressed in XenoMouse II strains are presented. Human μ, γ, and κ specific mRNAs were amplified by PCR, cloned and analyzed by sequencing as described in Materials and Methods. Table III shows a series of nucleotide sequences of 12 unique human heavy chain clones, divided into $V_H$, D, $J_H$ and N segments, as identified by homology with published germline sequences (Materials and Methods). Each D segment assignment is based on at least 8 bases of homology. Table IV shows a series of nucleotide sequences of V-J junctions of 8 independent human κ clones. The sequences are divided into $V_κ$, $J_κ$ and N segments and identified based on homology to published $V_κ$ and $J_κ$ sequences. In each of the Tables N-additions and deletions (indicated as _) were determined by their lack of sequence homology to V, D, or J sequences.

TABLE III

Repertoire Analysis of Human Heavy Chain Transcripts

| Clone | V_H | N | D_H | N | H_H |
|---|---|---|---|---|---|
| A2.2.1 | 5–51 (DP73) TTACTGTGCGAGACA (SEQ ID NO 30) | 4 (TAGG) | XP5rc AATCAT | 12 (GGGAGCTACGGG) (SEQ ID NO. 48) | JH4____GACTACTGGGGC (SEQ ID NO 50) |
| B2.1.5 | 3–33 (DP-50) TTACTGTGCGAGAGA (SEQ ID NO 31) | 7 (TCGGGGA) | 3rc AATAGCA | 7 (CTGGCCT) | JH4_CTTTGACTACTGGGGC (SEQ ID NO 51) |
| B4 2.4 | 3–15 (DP-38) TTACTGTACCACAGA (SEQ ID NO 32) | 1 (G) | K1 GGCTAC | 11 (ACTAACTACCC) (SEQ ID NO. 49) | JH6_CTACTACTACTACGGT (SEQ ID NO. 52) |
| B4 2.5 | 4–59(DP-71) TTACTGTGCGAGAGA (SEQ ID NO. 33) | 10 (TAGGAGTGTT) (SEQ ID NO 42) | 4 GTAGTACCAGCTGCTAT (SEQ ID NO 43) | 6 (ACCCAA) | JH6 __ACTACTACTACTACGGT (SEQ ID NO. 53) |
| D2 2.5 | 4–34 (DP-63) TTACTGTGCGAGAG_ (SEQ ID NO. 34) | 2 (GG) | N1 GCAGCAGCTG (SEQ ID NO 44) | 4 (CCCT) | JH4 _CTTTGACTACTGGGGC (SEQ ID NO 54) |
| D2.1.3 | 3–48(DP-51) TTACTGTGCGAGAGA (SEQ ID NO. 35) | 4 (TCTT) | XP1 GATATTTTGACTGGT (SEQ ID NO 45) | 2 (CT) | JH6 __CTACTACTACTACGGT (SEQ ID NO 55) |
| D2.2.8 | 4–31 (DP-65) TTACTGTGCGAGAGA (SEQ ID NO 36) | 2 (GA) | A4 GACTGCAG | 5 (CGGTT) | JH4 __ TTTGACTACTGGGGC (SEQ ID NO: 56) |
| A2 2.4 | 3–21 (DP-77) TTACTGTGCGAGAGA (SEQ ID NO: 37) | 2 (TT) | 1R3 GGGGCTGG | 3 (ACC) | JH6 _TACTACTACTACTACGGT (SEQ ID NO 57) |
| D4 2.11 | 4-4/4 35 ATTACTGTGCGA (SEQ ID NO. 38) | 1 (A) | N1 TATAGCAGTGGCTGGT (SEQ ID NO 46) | 2 (GT) | JH4 __ CTTTGACTACTGGGGC (SEQ ID NO 58) |
| C1 2.1 | 1–18(DP-14) TATTACTGTGCGAG_ (SEQ ID NO 39) | 0 | XP' 1/21-7 GTTA | 0 | JH4 ___ GACTACTGGGGC (SEQ UD NO. 59) |
| C3 1.2 | 4–39 (DP-79) TATTACTGTGCG__ (SEQ ID NO. 40) | 3 (GCC) | 2 GGATATAGTAGTGG (SEQ ID NO 47) | 6 (TCGGGC) | JH4 __ CTTTGACTACTGGGGC (SEQ ID NO 60) |
| D2 2.7 | 5–51 (DP73) TTACTGTGCGAGACA (SEQ ID NO. 41) | 4 (TGGC) | K1 AGTGGCT | 9 (GGTACTCTG) | JH3 ATGCTTTGATATCTGGGG (SEQ ID NO 61) |

TABLE IV

Repertoire Analysis of Human Kappa Light Chain Transcripts

| Clone | V_κ | N | J_κ |
|---|---|---|---|
| F2.2.3 | 02 (DPK9) TTAAACGAACAGTACCC C_ (SEQ ID NO: 62) | 0 | Jκ5 GATCACCTTCGGCCAA (SEQ ID NO: 70) |
| F4.1.8 | L5 (DPK5) ACAGGCTAACAOTTTCCCT C_ (SEQ ID NO: 63) | 0 | Jκ1 GGACGTTCGGCCAA (SEQ ID NO: 71) |
| F4.1.6 | A20 (DPK4) AAGTATAACAGTGCCCC (SEQ ID NO: 63) | 0 | Jκ3 ATTCACTTTCGGCCCT (SEQ ID NO: 72) |
| F2 2.5 | 08 ACAGTATGATAATCTCC C _ (SEQ ID NO: 65) | 0 | Jκ4 GCTCACTTTCGGCGGA (SEQ ID NO: 73) |
| F2.1.5 | L1 AAAGTATAATAGTTACC C _ (SEQ ID NO: 66) | 0 | Jκ5 GATCACCTTCGGCCAA (SEQ ID NO: 74) |
| F2.1.4 | A30 CAGCATAATAGTTACCC __ (SEQ ID NO: 67) | 0 | Jκ3 ATTCACTTTCGGCCCT (SEQ ID NO: 75) |

TABLE IV-continued

Repertoire Analysis of Human Kappa Light Chain Transcripts

| Clone | $V_\kappa$ | N | $J_\kappa$ | |
|---|---|---|---|---|
| F2.1.3 | B3 (DPK24) AATATTATAGTACTCC _ (SEQ ID NO. 68) | 0 | Jκ4 | GCTCACTTTCGGCGGA (SEQ ID NO: 76) |
| F4.1.3 | A27 (DPK22) CAGTATGGTAGCTCACCT C_ (SEQ ID NO: 69) | 1 | Jκ2 | ___ CACTTTTGGCCAG (G)(SEQ ID NO: 77) |

These results, together with sequences of XenoMouse-derived hybridomas described later, demonstrate a highly diverse, adult human-like utilization of V, D, and J genes, which appears to demonstrate that the entire human heavy and kappa chain variable regions present on the yH2 and the yK2 YACs are accessible to the mouse system for antibody rearrangement and are being utilized in a non-position-biased manner. In addition, the average length of N-additions and CDR3s for both the heavy and kappa chain transcripts, is very similar to that seen in adult human B-cells, indicating that the YAC DNA contained in the mice direct the mouse machinery to produce an adult human-like immune repertoire in mice.

In connection with the following Examples, we prepared high affinity antibodies to several antigens. In particular, antigens were prepared to human IL-8 and human EGFR. The rationale for the selection of IL-8 and EGFR is as follows.

IL-8 is a member of the C—X—C chemokine family. IL-8 acts as the primary chemoattractant for neutrophils implicated in many diseases, including ARDS, rheumatoid arthritis, inflammatory bowel disease, glomerulonephritis, psoriasis, alcoholic hepatitis, reperfusion injury, to name a few. Moreover, IL-8 is a potent angiogenic factor for endothelial cells. In FIGS. 22–28, we demonstrate that human anti-IL-8 antibodies derived from XenoMouse II strains are effective in a inhibiting IL-8's actions in a number of pathways. For example, FIG. 22 shows blockage of IL-8 binding to human neutrophils by human anti-IL-8. FIG. 23 shows inhibition of CD11b expression on human neutrophils by human anti-IL-8. FIG. 24 shows inhibition of IL-8 induced calcium influx by human anti-IL-8 antibodies. FIG. 25 shows inhibition of IL-8 RB/293 chemotaxis by human anti-IL-8 antibodies. FIG. 26 is a schematic diagram of a rabbit model of human IL-8 induced skin inflammation. FIG. 27 shows the inhibition of human IL-8 induced skin inflammation in the rabbit model of FIG. 26 with human anti-IL-8 antibodies. FIG. 28 shows inhibition of angiogenesis of endothelial cells on a rat corneal pocket model by human anti-IL-8 antibodies.

EGFR is viewed as an anti-cancer target. For example, EGFR is overexpressed, up to 100 fold, on a variety of cancer cells. Ligand (EGF and TNF) mediated growth stimulation plays a critical role in the initiation and progression of certain tumors. In this regard, EGFR antibodies inhibit ligand binding and lead to the arrest of tumor cell growth, and, in conjunction with chemotherapeutic agents, induces apoptosis. Indeed, it has been demonstrated that a combination of EGFR Mabs resulted in tumor eradication in murine xenogeneic tumor models. Imclone has conducted Phase I clinical utilizing a chimeric Mab (C225) that proved to be safe. In FIGS. 31–33, we demonstrate data related to our human anti-EGFR antibodies. FIG. 30 shows heavy chain amino acid sequences of human anti-EGFR antibodies derived from XenoMouse II strains. FIG. 31 shows blockage EGF binding to A431 cells by human anti-EGFR antibodies. FIG. 32 shows inhibition of EGF binding to SW948 cells by human anti-EGFR antibodies. FIG. 33 shows that human anti-EGFR antibodies derived from XenoMouse II strains inhibit growth of SW948 cells in vitro.

Example 9

High Affinity, Antigen-Specific Human Mabs Produced by XenoMouse II

We next asked whether the demonstrated utilization of the large human repertoire in XenoMouse II could be harnessed to generate human antibodies to multiple antigens, in particular, human antigens of significant clinical interest.

Accordingly, individual XenoMouse II pups were challenged each with one of three different antigen targets, human IL-8, human EGFR and human TNF-α. Antigens were administered in two different forms, either as soluble protein, in the case of IL-8 and TNF-α or expressed on the surface of cells (A431 cells), in the case of EGFR. For all three antigens, ELISAs performed on sera from immunized mice indicated a strong antigen-specific human antibody (IgG, Igκ) response with titers as high as $1:3\times10^6$. Negligible mouse λ response was detected.

Hybridomas were derived from spleen or lymph node tissues by standard hybridoma technology and were screened for secretion of antigen-specific human Mabs by ELISA.

An IL-8 immunized XenoMouse II yielded a panel of 12 hybridomas, all secreting fully human (hIgG$_2$κ) Mabs specific to human IL-8. Antibodies from four of these hybridomas, D1.1, K2.2, K4.2, and K4.3, were purified from ascitic fluid and evaluated for their affinity for human IL-8 and their potency in blocking binding of IL-8 to its receptors on human neutrophils.

Affinity measurements were performed by solid phase measurements of both whole antibody and Fab fragments using surface plasmon resonance in BIAcore and in solution by radioimmunoassay (Materials and Methods). As shown in Table V, affinity values measured for the four Mabs ranged from $1.1\times10^9$ to $4.8\times10^9$ M$^{-1}$. While there was some variation in the techniques employed, affinity values for all four antibodies were consistently higher than $10^9$ M$^{-1}$.

Figure 5A:
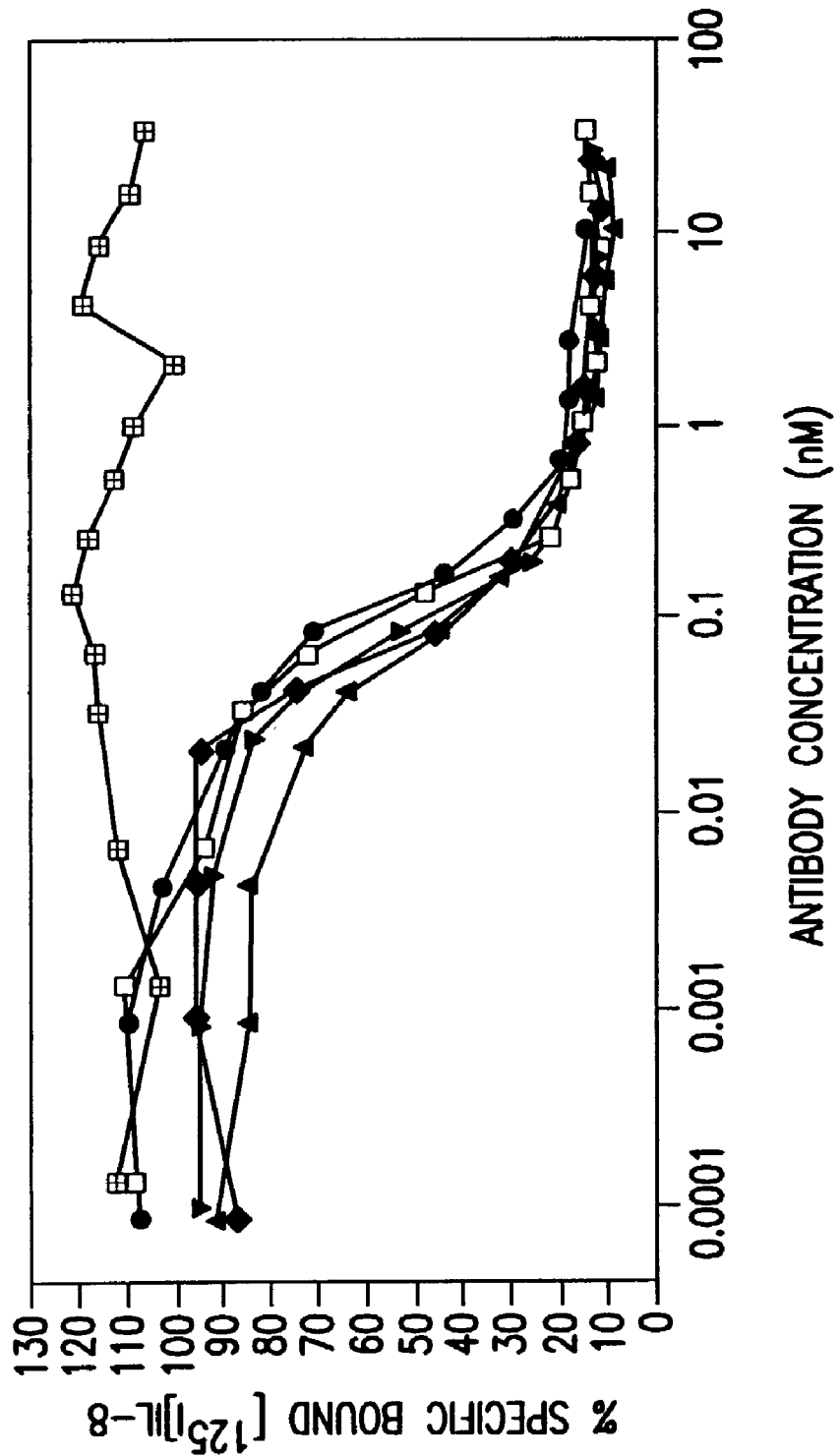

ELISA analysis confirmed that these four antibodies were specific to human IL-8 and did not cross-react with the closely related chemokines MIP-lα, GROα, β, and γ, ENA-78, MCP-1, or RANTES (data not shown). Further, competition analysis on the BIAcore indicated that the antibodies recognize at least two different epitopes (data not shown). All antibodies inhibit IL-8 binding to human neutrophils as effectively as the murine anti-human IL-8 neutralizing antibody, whereas a control human IgG$_2$κ antibody did not (FIG. 5A).

Fusion experiments with EGFR-immunized Xenomouse II yielded a panel of 25 hybridomas, all secreting EGFR-specific human IgG$_2$κ Mabs. Of the thirteen human Mabs analyzed, four (E2.1, E2.4, E2.5, E2.1 1) were selected for their ability to compete with EGFR-specific mouse antibody 225, which has previously been shown to inhibit EGF-mediated cell proliferation and tumor formation in mice (Sato et al., 1983). These human antibodies, purified from ascitic fluid, were evaluated for their affinity for EGFR and neutralization of EGF binding to cells. The affinities of these antibodies for EGFR, as determined by BIAcore measurements, ranged from $2.9\times10^9$ to $2.9\times10^{10}$ M$^{-1}$ (Table V).

Figure 5B:
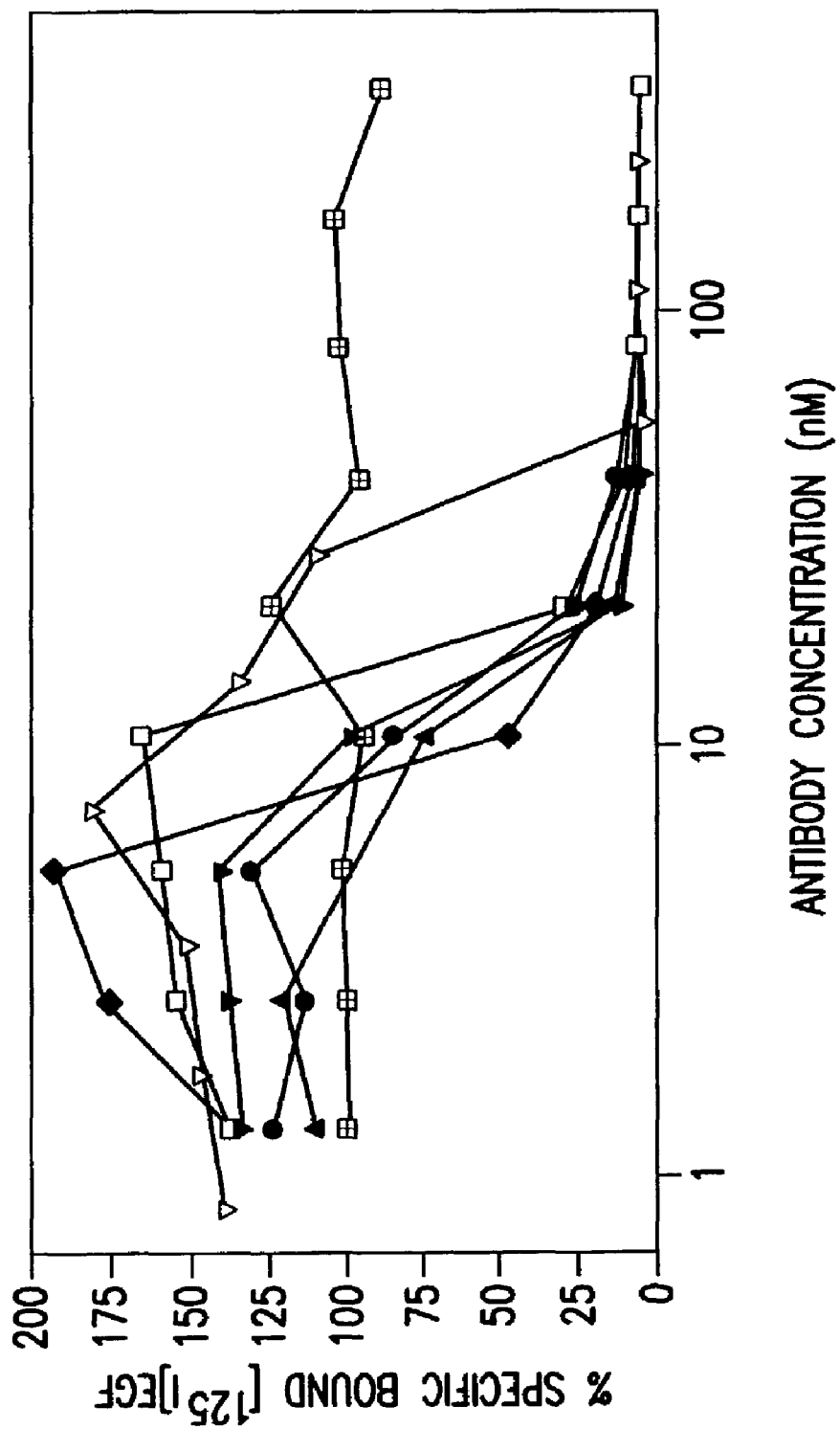

All four anti-EGFR antibodies completely blocked EGF binding to A43 1 cells (FIG. 5B), demonstrating their ability to neutralize its binding to both high and low affinity receptors on these cells (Kawamoto et al., 1983). Complete inhibition of EGF binding to EGFR expressed on human SW948 human lung carcinoma cells by all four anti-EGFR human antibodies was also observed (data not shown). In both cases, the fully human antibodies were as effective in inhibition of EGF binding as the anti-EGFR mouse antibody 225 and more potent than the 528 antibody (Gill et al., 1983). In both cell assays, a control human IgG$_2$κ antibody did not affect EGF binding (FIG. 5B and data not shown).

Figure 5C:
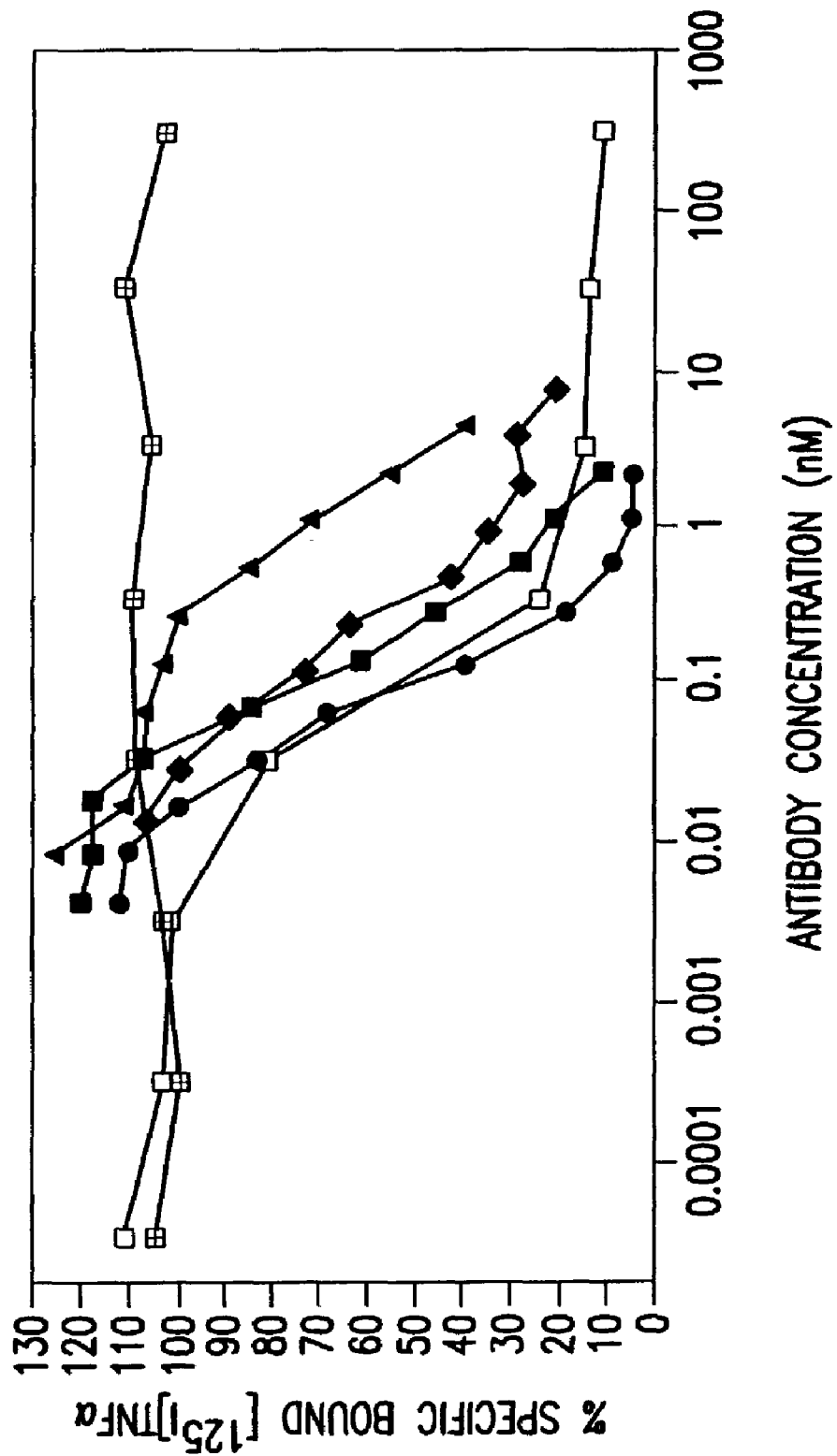

Fusion experiments with TNF-α immunized Xenomouse II yielded a panel of 12 human IgG$_2$κ antibodies. Four out of the 12 were selected for their ability to block the binding of TNF-α to its receptors on U937 cells (FIG. 5C). The affinities of these antibodies were determined to be in the range of $1.2$–$3.9\times10^9$ M$^{-1}$ (Table V).

The described Xenomouse-derived hybridomas produced antibodies at concentrations in the range of 2–19 μg/ml in static culture conditions. Characterization of the purified antibodies on protein gels under non-reducing conditions revealed the expected apparent molecular weight of 150 kD for the IgG$_2$κ antibody. Under reducing conditions the expected apparent molecular weights of 50 kD for the heavy and 25 kD for the light chain were detected (data not shown).

Table V, below, shows affinity constants of XenoMouse-derived antigen-specific fully human Mabs. The affinity constants of XenoMouse-derived human IgG$_2$κ Mabs specific to IL-8, EGFR, and TNF-α were determined by BIAcore or by radioimmunoassay as described in Materials and Methods. The values shown for IL-8 and EGFR are representative of independent experiments carried out with purified antibodies, while the values shown for TNF-α are from experiments carried out with hybridoma supernatants.

Example 10

Gene Usage and Somatic Hypermutation in Monoclonal Antibodies

Figure 6C:
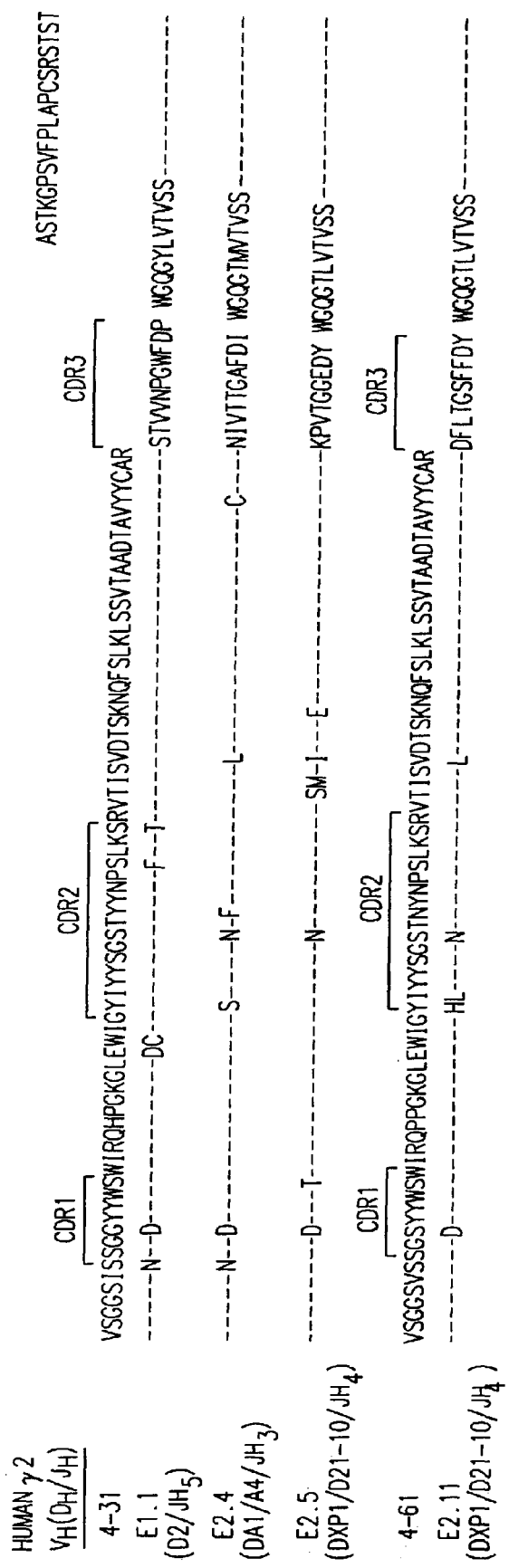
Figure 6D:
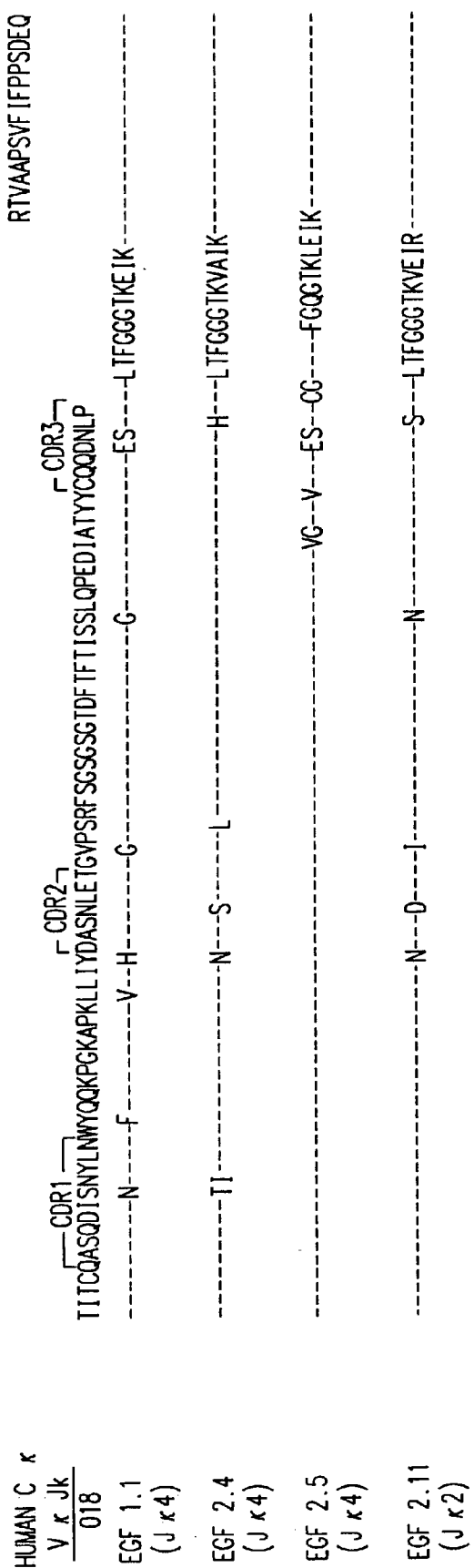
Figure 7:
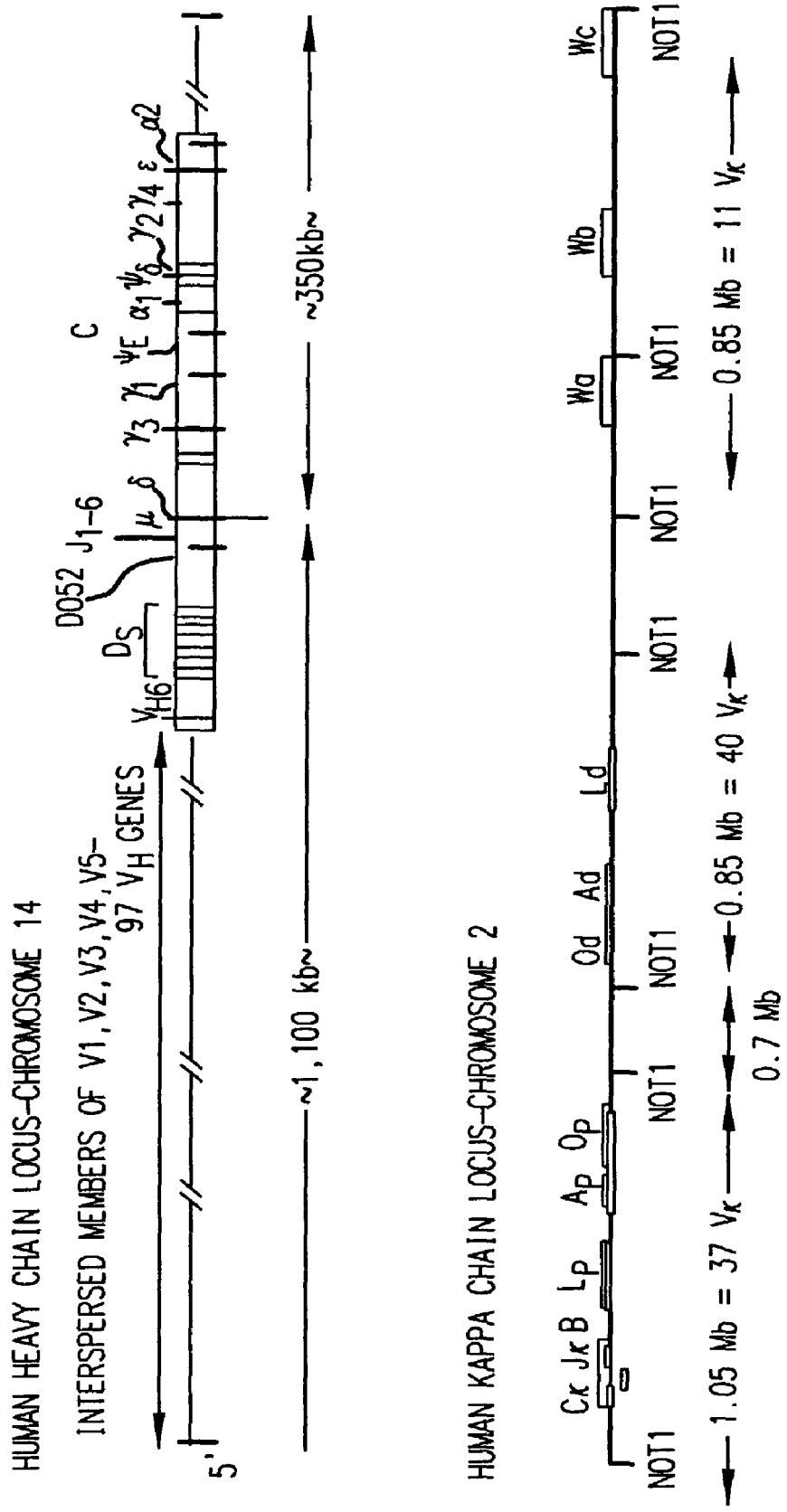
FIG. 7 is a schematic diagram of the human heavy chain genome and the human kappa light chain genome.
Figure 8:
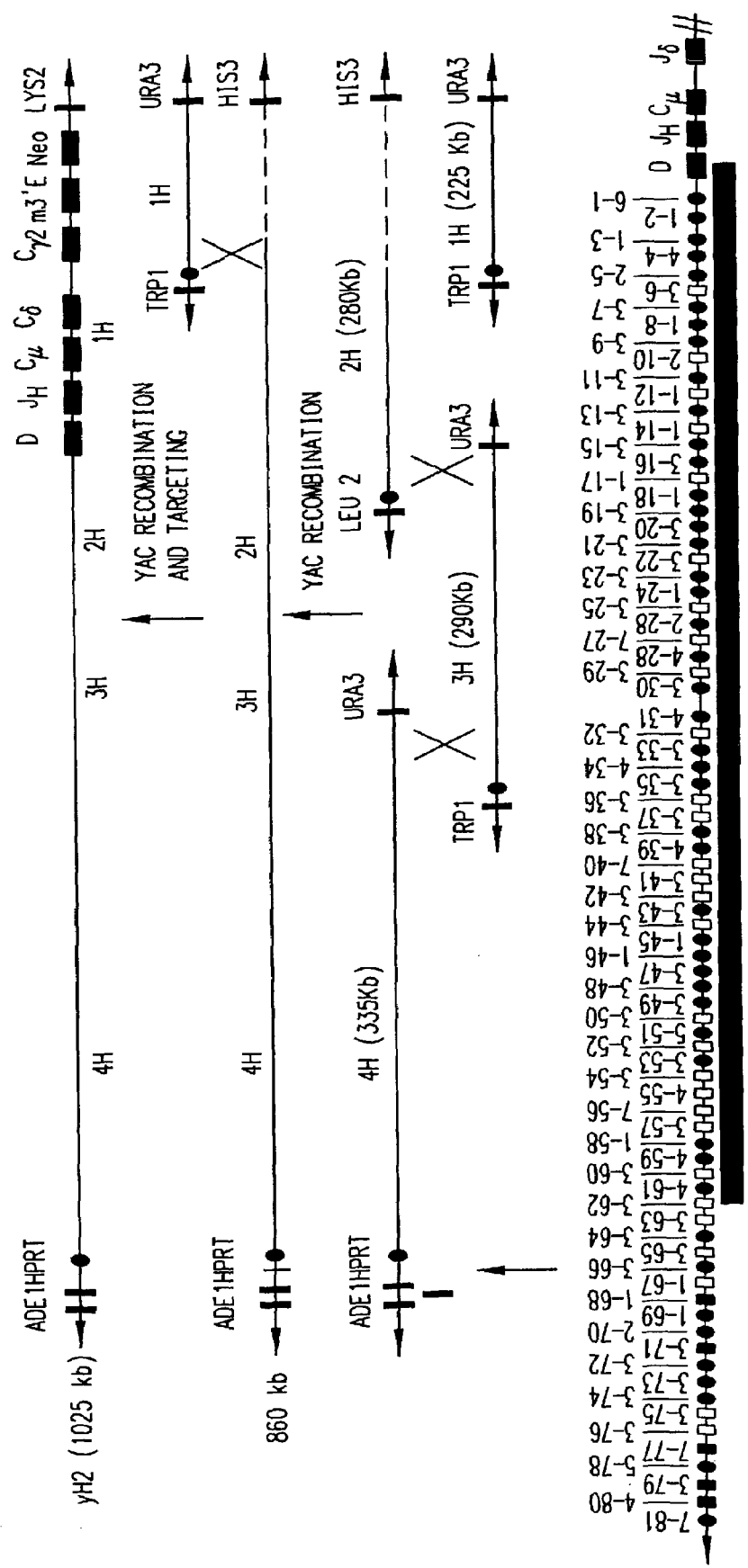
FIG. 8 is another schematic diagram showing the construction of the yH2 (human heavy chain) YAC.
Figure 9:
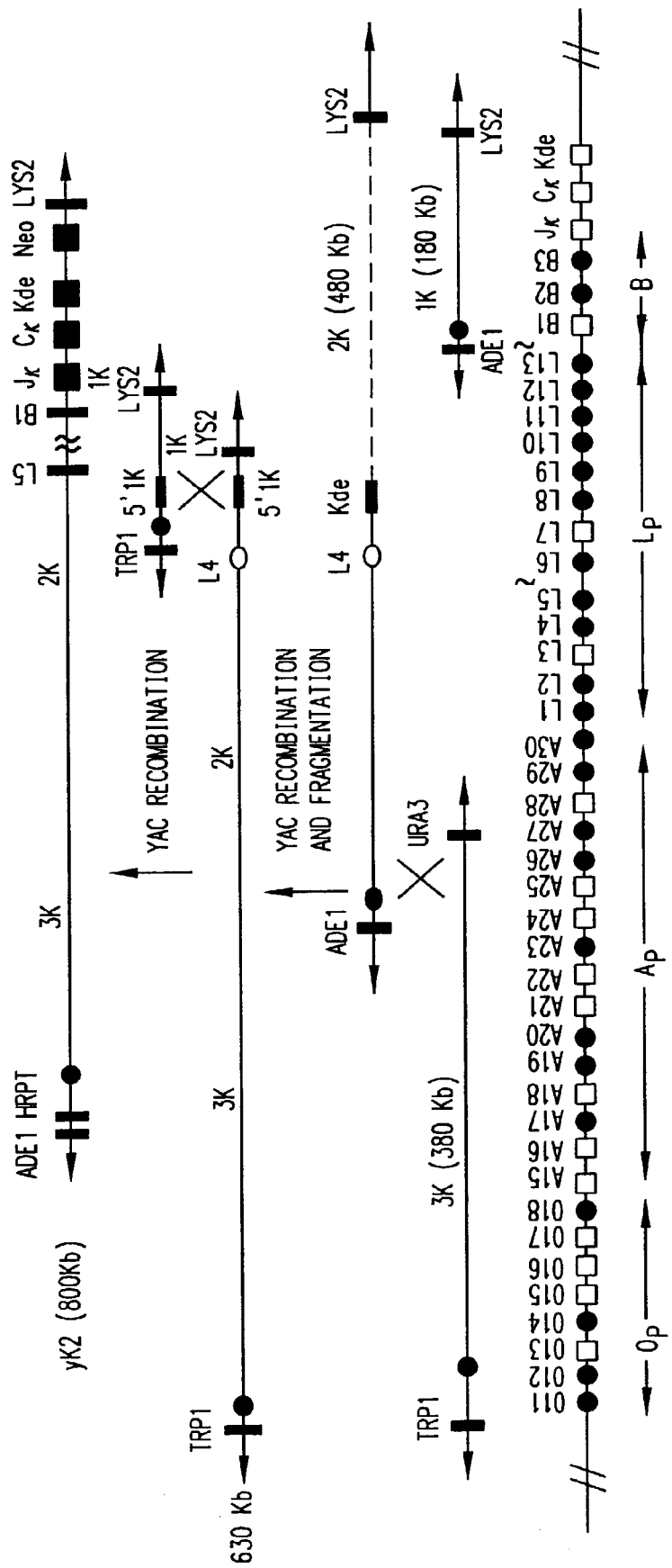
FIG. 9 is another schematic diagram showing the construction of the yK2 (human kappa light chain) YAC.
Figure 10:
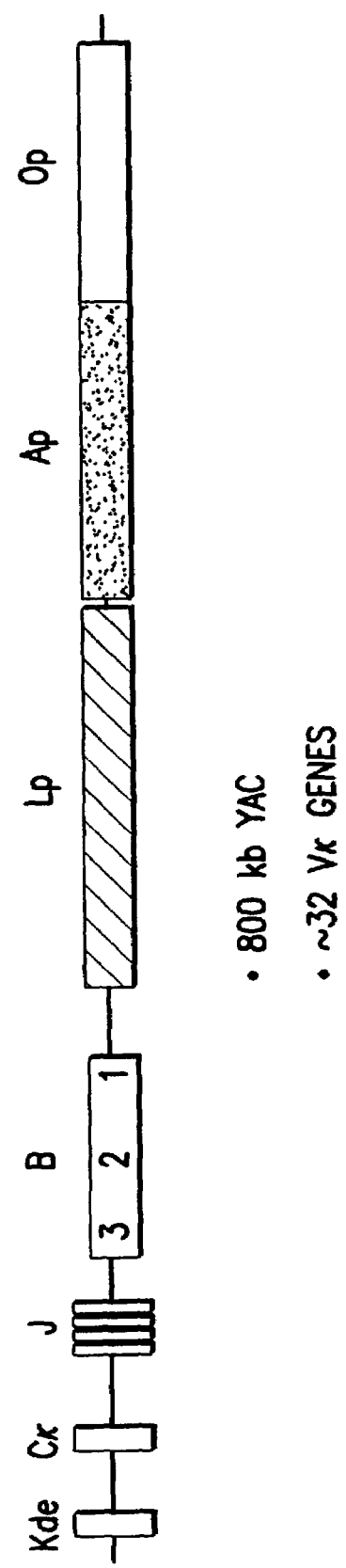
FIG. 10 is another schematic diagram showing the construction of the yK2 (human kappa light chain) YAC.
Figure 11A:
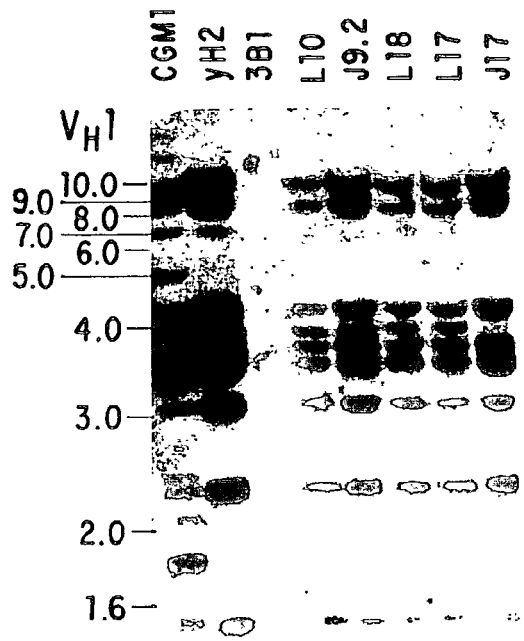
FIGS. 11A–11I show a series of Southern Blot analyses demonstrating integration intact of the yH2 (human heavy chain) YAC into ES cells and into the mouse genome. Detailed discussion is provided in connection with FIGS. 2A–2I.
Figure 11C:
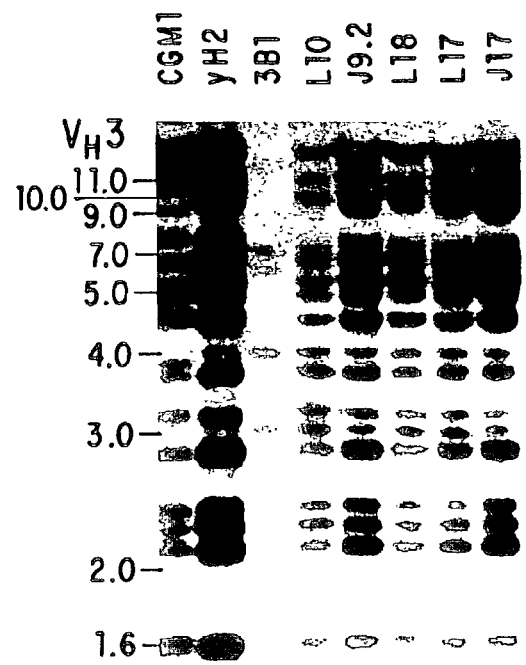
Figure 11B:
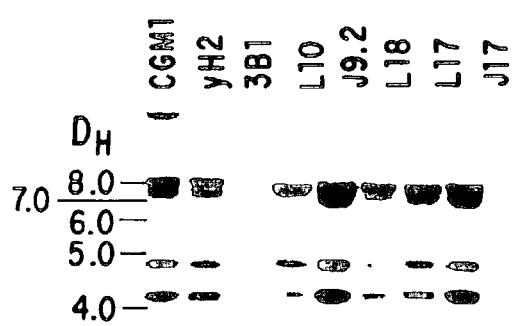
Figure 11D:
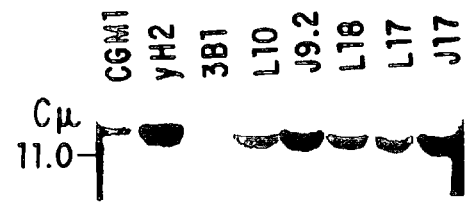
Figure 11E:
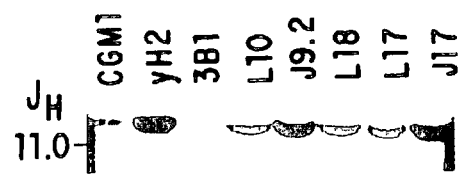
Figure 11F:
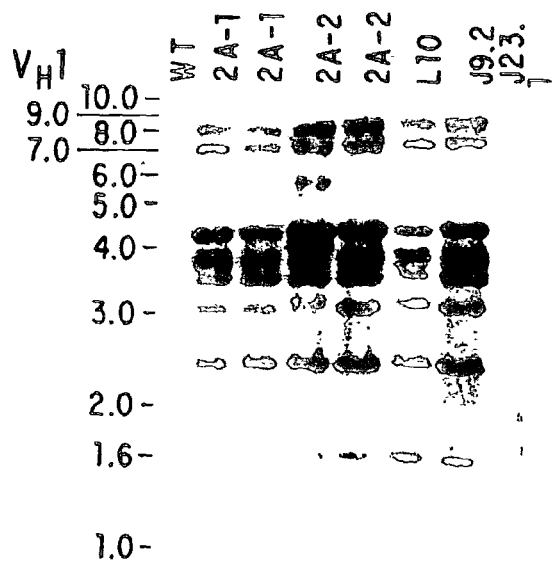
Figure 11H:
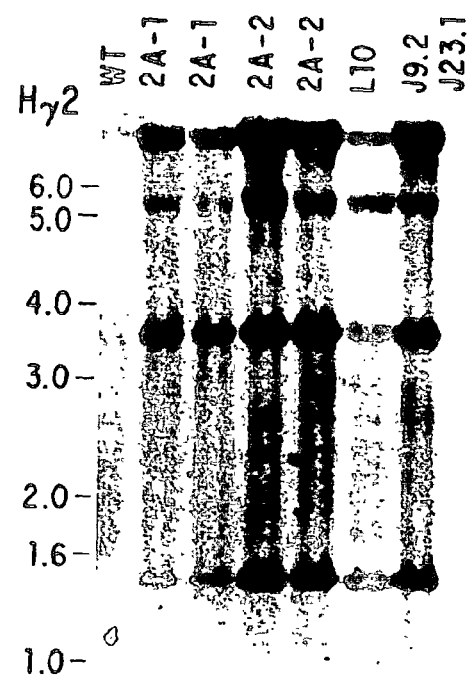
Figure 11G:
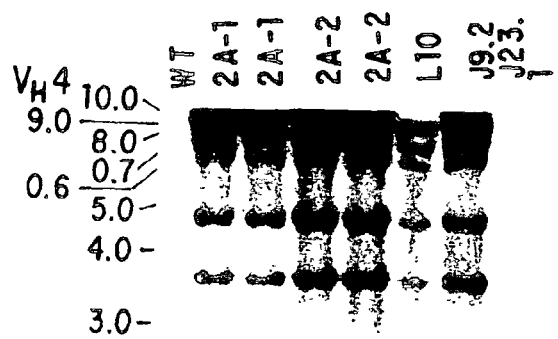
Figure 11I:
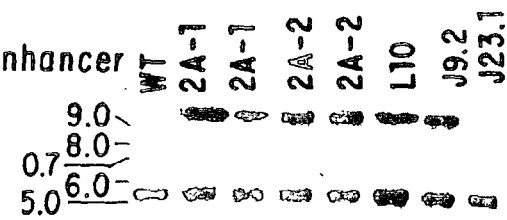
Figure 12A:
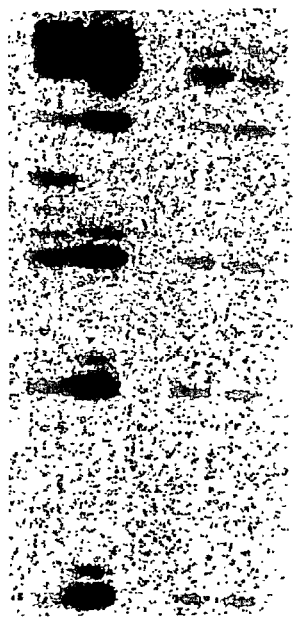
Figure 12B:
Figure 12C:
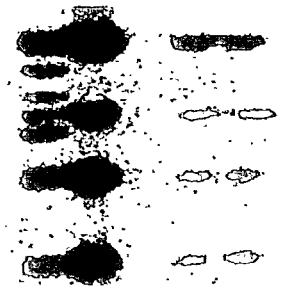
Figure 12D:
Figure 12E:
Figure 13A:
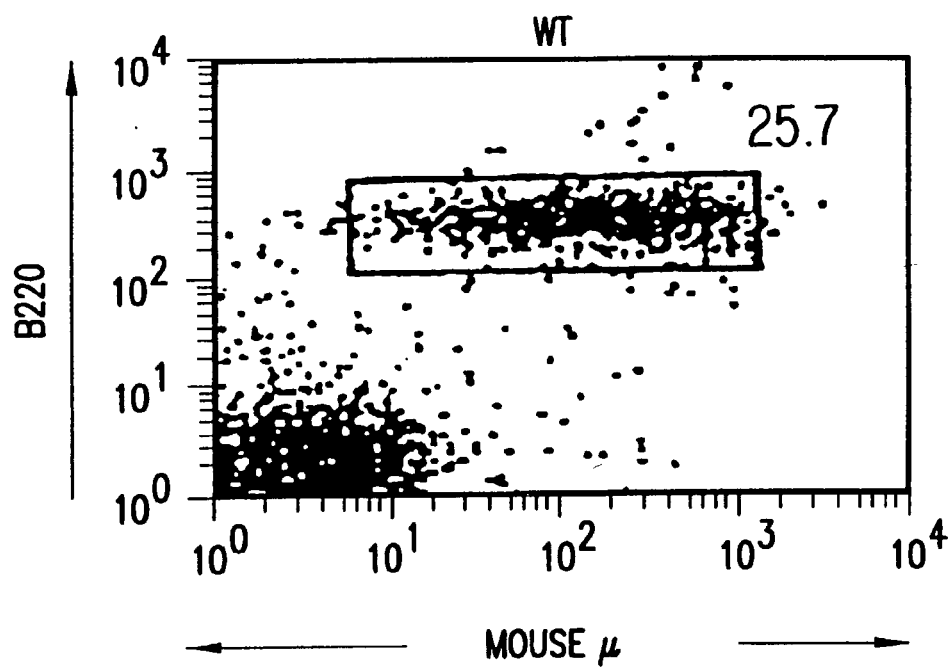
FIGS. 13A–13F show B-cell reconstitution and surface expression of human μ, δ, and κ chains and mouse λ chains on XenoMouse-derived B-cells and shows flow cytometry analysis of peripheral blood. Further details are provided in connection with FIGS. 4A–4T.
Figure 13B:
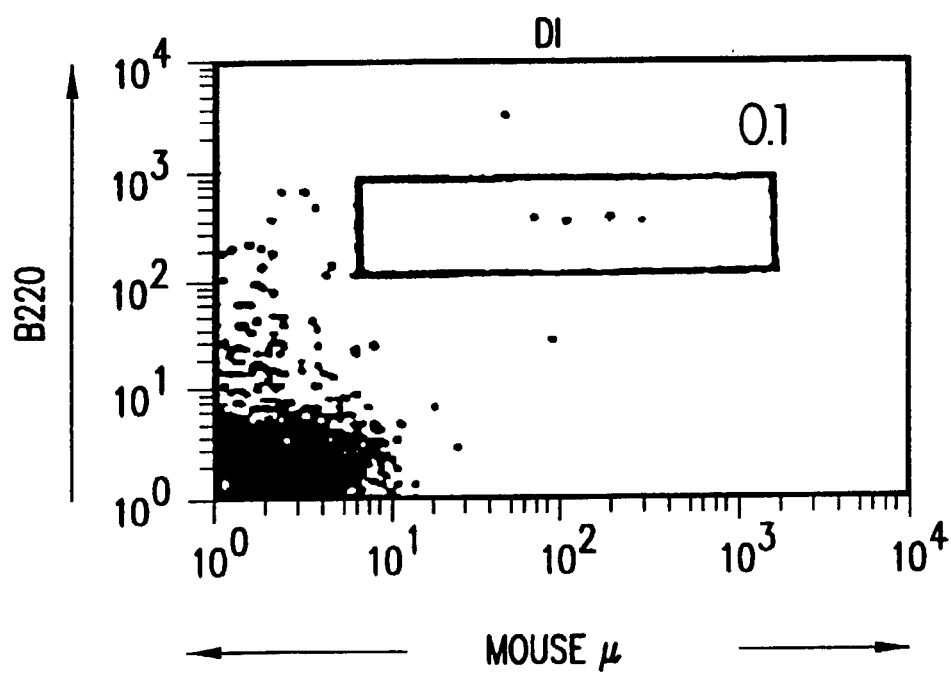
Figure 13C:
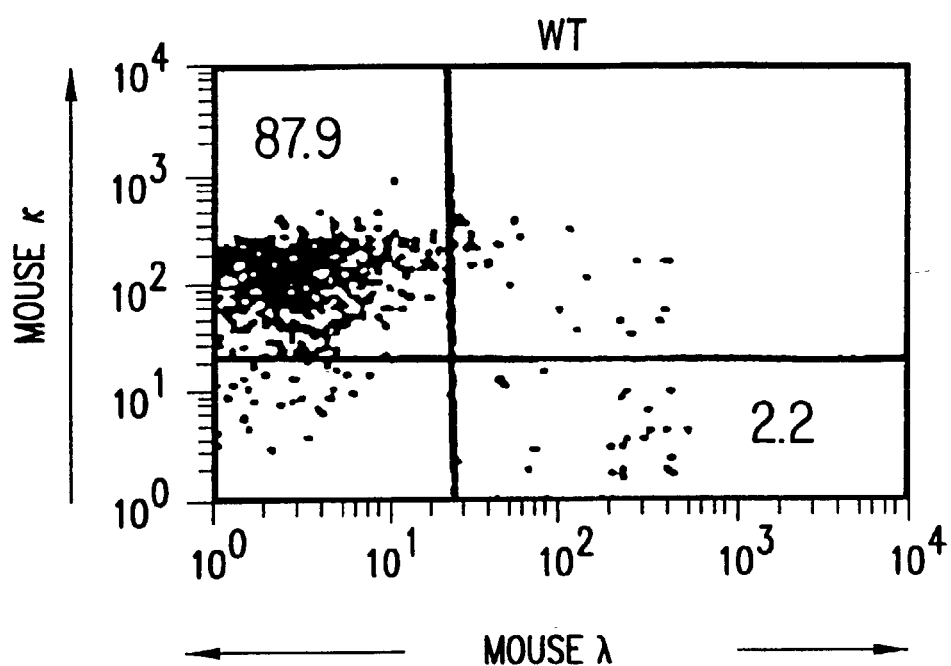
Figure 13D:
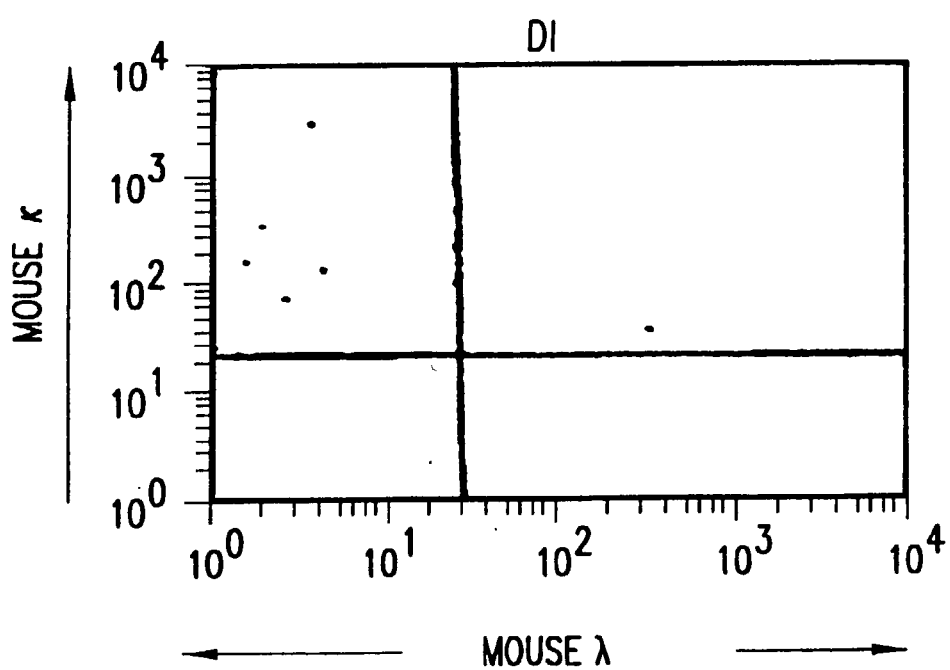
Figure 13E:
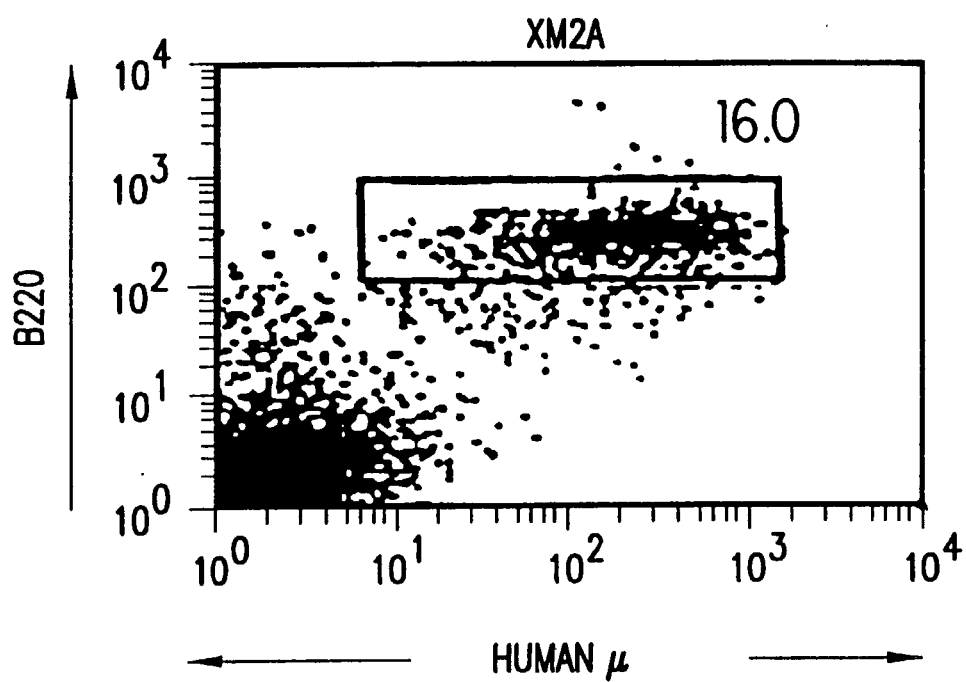
Figure 13F:
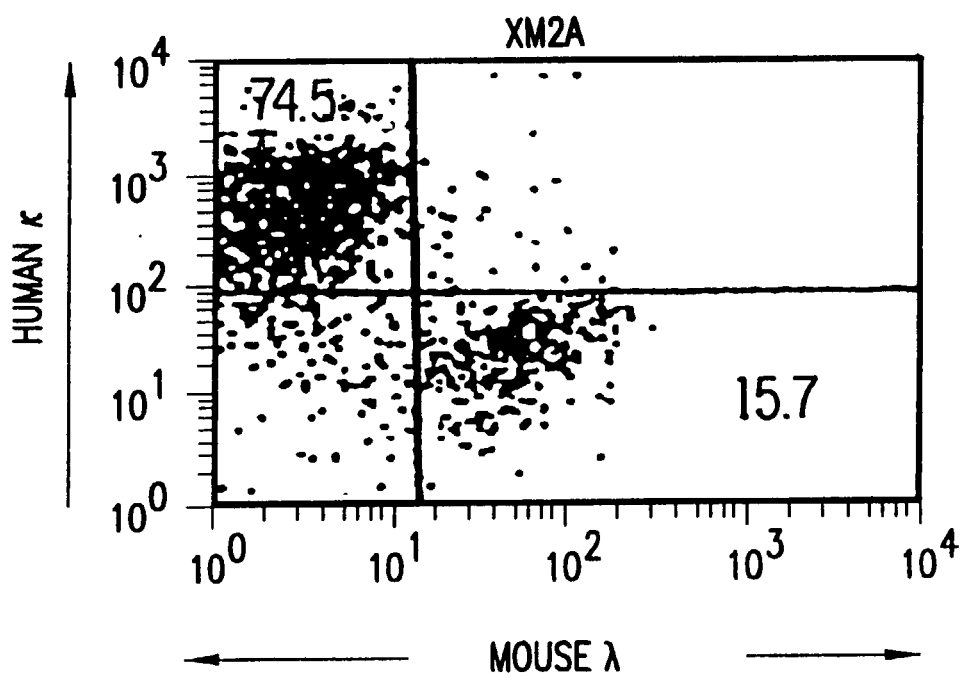

The sequences of the heavy and kappa light chain transcripts from the described IL-8 and EGFR-human Mabs were determined FIG. 6 and Figures [[ ]]. The four IL-8-specific antibodies consisted of at least three different $V_H$ genes ($V_{H4-34}$/$V_{H4-21}$, $V_{H3-30}$, and $V_{H5-51}$), four different $D_H$ segments (A1/A4, K1, ir3rc, and 21–10rc) and two $J_H$ ($J_{H3}$ and $J_{H4}$) gene segments. Three different Vκ genes (012, 018, and B3) combined with Jκ3 and Jκ4 genes. Such diverse utilization shows that Xenomouse II is capable of producing a panel of anti-IL-8 neutralizing antibodies with diverse variable regions.

In contrast to the IL-8 antibody transcripts, the sequences of antibodies selected for their ability to compete with Mab 225 showed relatively restricted $V_H$ and Vκ gene usage, with three antibodies, E1.1, E2.4 and E2.5 sharing the same $V_H$ gene (4–31) and E2.11 containing $V_{H4-61}$, which is highly homologous to $V_{H4-31}$. Different D (2, A1/A4, XP1) and $J_H$ ($J_H3$, $J_H4$, $J_H5$) segments were detected. All four antibodies were shown to share the same Vκ (018) gene. Three of them contained Jκ4, and one, E2.5, contained Jκ2.

Most $V_H$ and Vκ hybridoma transcripts showed extensive nucleotide changes (7–17) from the corresponding germline segments, whereas no mutations were detected in the constant regions. Most of the mutations in V segments resulted in amino acid substitutions in the predicted antibody amino acid sequences (0–12 per V gene), many in CDR1 and CDR2 regions (Figure _). Of note are the mutations which are shared by the heavy chain sequences of EGFR antibodies, such as the Gly→Asp substitution in CDR1, shared by all antibodies, or Ser→Asn substitution in CDR2 and Val→Leu in the framework region 3 shared by three antibodies. These results indicated that an extensive process of somatic hypermutation, leading to antibody maturation and selection, is occurring in Xenomouse II.

TABLE V

| Human Mab IgG$_2$κ | Antigen | ka (M$^{-1}$S$^{-1}$) | kd (S$^{-1}$) | KA (M$^{-1}$) | KD (M) | Surface Density [RU] | Radio Immunoassay (M$^{-1}$) |
|---|---|---|---|---|---|---|---|
| | | Solid Phase Measurements | | | | | Solution |
| D1.1 | IL-8 | $2.7 \times 10^6$ | $9.9 \times 10^{-4}$ | $2.7 \times 10^9$ | $3.7 \times 10^{-10}$ | 81 | $2.0 \times 10^{10}$ |
| D1.1 Fab | IL-8 | $2.1 \times 10^6$ | $2.1 \times 10^{-3}$ | $1.1 \times 10^9$ | $8.8 \times 10^{-10}$ | 81 | $4.9 \times 10^{11}$ |
| K2.2 | IL-8 | $0.9 \times 10^6$ | $2.3 \times 10^{-4}$ | $4.0 \times 10^9$ | $2.5 \times 10^{-10}$ | 81 | $1.0 \times 10^{10}$ |
| K4.2 | IL-8 | $2.5 \times 10^6$ | $4.1 \times 10^{-4}$ | $6.3 \times 10^9$ | $1.6 \times 10^{-10}$ | 81 | ND |
| K4.3 | IL-8 | $4.3 \times 10^6$ | $9.4 \times 10^{-4}$ | $4.5 \times 10^9$ | $2.2 \times 10^{-10}$ | 81 | $2.1 \times 10^{11}$ |
| K4.3 Fab | IL-8 | $6.0 \times 10^6$ | $2.1 \times 10^{-3}$ | $2.9 \times 10^9$ | $3.4 \times 10^{-10}$ | 81 | |
| | | | | | | | ELISA (M) |
| E1.1 | EGFR | $1.9 \times 10^6$ | $6.5 \times 10^{-4}$ | $2.9 \times 10^9$ | $3.46 \times 10^{-10}$ | 303 | $1.1 \times 10^{-10}$ |
| E2.5 | EGFR | $2.1 \times 10^6$ | $1.8 \times 10^{-4}$ | $1.2 \times 10^{10}$ | $8.44 \times 10^{-11}$ | 303 | $3.6 \times 10^{-10}$ |
| E2.11 | EGFR | $1.7 \times 10^6$ | $4.7 \times 10^{-4}$ | $3.7 \times 10^9$ | $2.68 \times 10^{-10}$ | 303 | $1.1 \times 10^{-10}$ |
| E2.4 | EGFR | $2.8 \times 10^6$ | $9.78 \times 10^{-5}$ | $2.9 \times 10^{10}$ | $3.5 \times 10^{-11}$ | 818 | $1.1 \times 10^{-10}$ |
| T22.1 | TNF-α | $1.6 \times 10^6$ | $1.3 \times 10^{-3}$ | $1.2 \times 10^9$ | $8.06 \times 10^{-10}$ | 107 | |
| T22.4 | TNF-α | $2.4 \times 10^6$ | $4.6 \times 10^{-4}$ | $5.3 \times 10^9$ | $1.89 \times 10^{-10}$ | 107 | |
| T22.8 | TNF-α | $1.7 \times 10^6$ | $7.5 \times 10^{-4}$ | $2.3 \times 10^9$ | $4.3 \times 10^{-10}$ | 107 | |
| T22.9 | TNF-α | $2.3 \times 10^6$ | $4.9 \times 10^{-4}$ | $4.8 \times 10^9$ | $2.11 \times 10^{-10}$ | 107 | |
| T22.11 | TNF-α | $2.9 \times 10^6$ | $7.9 \times 10^{-4}$ | N/A | $2.76 \times 10^{-10}$ | 107 | |

Discussion

This present application describes the first functional substitution of complex, megabase-sized mouse loci, with human DNA fragments equivalent in size and content reconstructed on YACs. With this approach, the mouse humoral immune system was "humanized" with megabase-sized human Ig loci to substantially reproduce the human antibody response in mice deficient in endogenous antibody production.

Our success in faithful reconstruction of a large portion of the human heavy and kappa light chain loci, nearly in germline configuration, establishes YAC recombination in yeast as a powerful technology to reconstitute large, complex and unstable fragments, such as the Ig loci (Mendez et al., 1995), and manipulate them for introduction into mammalian cells. Furthermore, the successful introduction of the two large heavy and kappa light chain segments into the mouse germline in intact form confirms the methodology of ES cell-yeast spheroplast fusion as a reliable and efficient approach to delivering xenogeneic loci into the mouse germline.

Characterization of Xenomouse II strains has shown that the large Ig loci were capable of restoring the antibody system, comparable in its diversity and functionality to that of wildtype mice, and much superior to the humoral response produced in mice bearing human Ig minigene constructs (Lonberg et al., 1994) or small human Ig YACs (Green et al., 1994). This difference was manifested in the levels of mature B-cells, human Ig production, class switching efficiency, diversity, preponderance of human Igκ over murine Igλ production, and magnitude of the human antibody response, and success in the generation of high affinity, antigen-specific monoclonal antibodies to multiple antigens.

The levels of mature B-cells and human antibodies in Xenomouse II are the highest yet reported for Ig-transgenic mice, representing a several-fold increase over the levels shown for previous mice and approaching those of wildtype mice. In particular, the levels of the human IgG were more than 100 fold higher than those reported for mice bearing minilocus Ig transgenes with human γ1 gene (Lonberg et al., 1994). The more efficient class switching in Xenomouse II was likely the result of the inclusion of the entire switch regions, with all of their regulatory elements, as well as the additional control elements on yH2, which may be important to support and maintain proper class switching. The elevated levels of mature B-cells in Xenomouse II strains are likely to result from the higher rearrangement frequency and thus improved B-cell development in the bone marrow due to the increased V gene repertoire. B-cell reconstitution is expected to be even more pronounced in XenoMouse II strains that are homozygous for the human heavy chain locus.

The ratio of human κ to mouse λ light chain expression by circulating B-cells provides a useful internal measure of the utilization of the transgenic kappa chain locus. Whereas in mice containing one allele of smaller Ig YACs, an approximately equal distribution of human κ and mouse λ was observed, a significant preponderance of human κ was detected in Xenomouse II strains. Moreover, in animals homozygous for yK2 possessed a κ:λ ratio that is identical to wild type mice. These observations together with the broad Vκ gene usage strongly suggest that the human proximal Vκ genes in the Xenomouse II are sufficient to support a diverse light chain response and are consistent with the bias toward proximal Vκ gene usage in humans (Cox et al., 1994).

Xenomouse II strains exhibited highly increased antibody diversity with V, D, and J genes across the entire span of the loci accessed by the recombination mechanism and incorporated into mature antibodies. Once triggered by antigen binding, extensive somatic hypermutation occurs, leading to affinity maturation of the antibodies.

The utilization pattern of V, D, J genes in Xenomouse II also indicated they are available and utilized in a manner reminiscent of their utilization in humans, yielding an adult-like human antibody repertoire, which is different from the fetal-like, position-biased usage observed in Ig minigene-bearing mice (Taylor et al., 1992; Taylor et al., 1994; Tuaillon et al., 1993). The broad utilization of many of the functional $V_H$ and Vκ genes together with the multiplicity of antigens recognized by the mice underscores the importance of the large V gene repertoire to successfully reconstituting a functional antibody response.

The ultimate test for the extent of reconstitution of the human immune response in mice is the spectrum of antigens to which the mice will elicit an antibody response and the ease with which antigen-specific high affinity Mabs can be generated to different antigens. Unlike mice engineered with smaller human Ig YACs or minigenes, which yielded to date only a limited number of antigen-specific human Mabs (Lonberg et al., 1994; Green et al., 1994; Fishwild et al., 1996), Xenomouse II generated Mabs to all human antigens tested to date. Xenomouse II strains mounted a strong human antibody response to different human antigens, presented either as soluble proteins or expressed on the surfaces of cells. Immunization with each of the three human antigens tested yielded a panel of 10–25 antigen-specific human $IgG_2$κ Mabs. For each antigen, a set of antibodies with affinities in the range of $10^9$–10 $M^{-1}$ was obtained. Several measures were taken to confirm that the affinity values represent univalent binding kinetics rather than avidity: BIAcore assays with intact antibodies were carried out with sensor chips coated at low antigen density to minimize the probability of bivalent binding; for two antibodies, the assay was repeated with monovalent Fab fragments; some of the antibodies were also tested by solution radioimmunoassay. From the results of these measurements, we conclude that antibodies with affinities in the range of $10^{10}$ $M^{-1}$ are readily attainable with the XenoMouse. The affinity values obtained for XenoMouse-derived antibodies are the highest to be reported for human antibodies against human antigens produced from either engineered mice (Lonberg et al., Fishwild et al., 1996) or from combinatorial libraries (Vaughan et al., 1996). These high affinities combined with the extensive amino acid substitution as a result of somatic mutation in the V genes confirms that the mechanism of affinity maturation is intact in Xenomouse II and comparable to that in wildtype mice.

These results show that the large antibody repertoire on the human Ig YACs is being properly exploited by the mouse machinery for antibody diversification and selection, and, due to the lack of immunological tolerance to human proteins, can yield high affinity antibodies against any antigen of interest, including human antigens. The facility with which antibodies to human antigens can be generated by the human immunoglobulin genes in these mice provides further confirmation that self tolerance at the B-cell level is acquired and not inherited.

The ability to generate high affinity fully human antibodies to human antigens has obvious practical implications. Fully human antibodies are expected to minimize the immunogenic and allergic responses intrinsic to mouse or mouse-derivatized Mabs and thus to increase the efficacy and safety of the administered antibodies. Xenomouse II offers the opportunity of providing a substantial advantage in the treatment of chronic and recurring human diseases, such as inflammation, autoimmunity, and cancer, which require repeated antibody administrations. The rapidity and reproducibility with which XenoMouse II yields a panel of fully human high affinity antibodies indicates the potential advance it offers over other technologies for human antibody production. For example, in contrast to phage display, which requires intensive efforts to enhance the affinity of many of its derived antibodies and yields single chain Fvs or Fabs, Xenomouse II antibodies are high affinity fully intact immunoglobulins which can be produced from hybridomas without further engineering.

The strategy described here for creation of an authentic human humoral immune system in mice can be applied towards humanization of other multi-gene loci, such as the T cell receptor or the major histocompatibility complex, that govern other compartments of the mouse immune system (Jakobovits, 1994). Such mice would be valuable for elucidating the structure-function relationships of the human loci and their involvement in the evolution of the immune system.

INCORPORATION BY REFERENCE

All references cited herein, including patents, patent applications, papers, text books, and the like, and the references cited therein, to the extent that they are not already, are hereby incorporated herein by reference in their entirety. In addition, the following references are also incorporated by reference herein in their entirety, including the references cited in such references:

Albertsen et al., "Construction and characterization of a yeast artificial chromosome library containing seven haploid human genome equivalents." *Proc. Natl. Acad. Sci.* 87:4256 (1990).

Anand et al., "Construction of yeast artificial chromosome libraries with large inserts using fractionation by pulsed-field gel electrophoresis." *Nucl. Acids Res.* 17:3425–3433 (1989).

Berman et al. "Content and organization of the human Ig VH locus: definition of three new $V_H$ families and linkage to the Ig CH locus." *EMBO J.* 7:727–738 (1988).

Brezinschek et al., "Analysis of the heavy chain repertoire of human peripheral B-cells using single-cell polymerase chain reaction." *J. Immunol.* 155:190–202 (1995).

Brownstein et al., "Isolation of single-copy human genes from a library of yeast artificial chromosome clones." *Science* 244:1348–1351 (1989).

Bruggemann et al. *PNAS USA* 86:6709–6713 (1989).

Bruggemann et al., "Human antibody production in transgenic mice: expression from 100 kb of the human IgH locus." *Eur. J. Immunol.* 21:1323–1326 (1991).

Bruggeman, M. and Neuberger, M. S. in *Methods: A companion to Methods in Enzymology* 2:159–165 (Lerner et al. eds. Academic Press (1991)).

Bruggemann, M. and Neuberger, M. S. "Strategies for expressing human antibody repertoires in transgenic mice." *Immunology Today* 17:391–397 (1996).

Chen et al. "Immunoglobulin gene rearrangement in B-cell deficient mice generated by targeted deletion of the $J_H$ locus." *International Immunology* 5:647–656 (1993).

Choi et al. "Transgenic mice containing a human heavy chain immunoglobulin gene fragment cloned in a yeast artificial chromosome." *Nature Genetics* 4:117–123 (1993).

Coligan et al., Unit 2.1, "Enzyme-linked immunosorbent assays," in *Current protocols in immunology* (1994).

Cook, G. P. and Tomlinson, I. M., "The human immunoglobulin $V_H$ repertoire." *Immunology Today* 16:237–242 (1995).

Cox et al., "A directory of human germ-line Vx segments reveals a strong bias in their usage." *Eur. J. Immunol.* 24:827–836 (1994).

Dariavach et al., "The mouse IgH 3'-enhancer." *Eur. J. Immunol.* 21:1499–1504 (1991).

Den Dunnen et al., "Reconstruction of the 2.4 Mb human DMD-gene by homologous YAC recombination." *Human Molecular Genetics* 1:19–28 (1992).

Feeney, A. J. "Lack of N regions in fetal and neonatal mouse immunoglobulin V-D-J junctional sequences." *J. Exp. Med.* 172:137–1390 (1990).

Fishwild et al., "High-avidity human IgGκ monoclonal antibodies from a novel strain of minilocus transgenic mice." *Nature Biotech.* 14:845–851 (1996).

Flanagan, J. G. and Rabbitts, T. H., "Arrangement of human immunoglobulin heavy chain constant region genes implies evolutionary duplication of a segment containing γ, ∈, and α genes." *Nature* 300:709–713 (1982).

Galfre, G. and Milstein, C., "Preparation of monoclonal antibodies: strategies and procedures." *Methods Enzymol.* 73:3–46(1981).

Gemmill et al., "Protocols for pulsed field gel electrophoresis: Separation and detection of large DNA molecules." *Advances in Genome Biology* 1:217–251 (1991).

Gill et al., "Monoclonal anti-epidermal growth factor receptor antibodies which are inhibitors of epidermal growth factor binding and antagonists of epidermal growth factor-stimulated tyrosine protein kinase activity." *J. Biol. Chem.* 259:7755 (1984).

Green et al., "Antigen-specific human monoclonal antibodies from mice engineered with human Ig heavy and light chain YACs." *Nature Genetics* 7:13–21 (1994).

Hermanson et al., "Rescue of end fragments of yeast artificial chromosomes by homologous recombination in yeast." *Nucleic Acids Res.* 19:4943–4948 (1991).

Huber et al., "The human immunoglobulin κ locus. Characterization of the partially duplicated L regions." *Eur. J. Immunol.* 23:2860–2967 (1993).

Jakobovits, A., "Humanizing the mouse genome." *Current Biology* 4:761–763 (1994).

Jakobovits, A., "Production of fully human antibodies by transgenic mice." *Current Opinion in Biotechnology* 6:561–566 (1995).

Jakobovits et al., "Germ-line transmission and expression of a human-derived yeast artificial-chromosome." *Nature* 362:255–258 (1993).

Jakobovits, A. et al., "Analysis of homozygous mutant chimeric mice: Deletion of the immunoglobulin heavy-chain joining region blocks B-cell development and antibody production." *Proc. Natl. Acad. Sci. USA* 90:2551–2555 (1993).

Kawamoto et al., "Growth stimulation of A431 cells by epidermal growth factor: Identification of high affinity receptors for EGF by an anti-receptor monoclonal antibody." *Proc. Nat. Acad. Sci., USA* 80:1337–1341 (1983).

Lonberg et al., "Antigen-specific human antibodies from mice comprising four distinct genetic modifications." *Nature* 368:856–859 (1994).

Lusti-Marasimhan et al., "Mutation of Leu25 and Val27 introduces CC chemokine activity into interleukin-8." *J. Biol. Chem.* 270:2716–2721 (1995).

Marks et al., "Oligonucleotide primers for polymerase chain reaction amplification of human immunoglobulin variable genes and design of family-specific oligonucleotide probes." *Eur. J. Immunol.* 21:985–991 (1991).

Matsuda et al., "Structure and physical map of 64 variable segments in the 3' 0.8-megabase region of the human immunoglobulin heavy-chain locus." *Nature Genetics* 3:88–94 (1993).

Max, E. *Molecular genetics of immunoglobulins. Fundamental Immunology.* 315–382 (Paul, W. E., ed., New York: Raven Press (1993)).

Mendez et al., "A set of YAC targeting vectors for the interconversion of centric and acentric arms." *Cold Spring Harbor Laboratory Press, Genome Mapping and Sequencing meeting,* 163 (1993).

Mendez et al., "Analysis of the structural integrity of YACs comprising human immunoglobulin genes in yeast and in embryonic stem cells." *Genomics* 26:294–307 (1995).

Ray, S. and Diamond, B., "Generation of a fusion partner to sample the repertoire of Splenic B-cells destined for apoptosis." *Proc. Natl. Acad. Sci. USA* 91:5548–5551 (1994).

Sato et al., "Biological effects in vitro of monoclonal antibodies to human epidermal growth factor receptors" *Mol. Biol. Med.* 1:511–529 (1983).

Schiestl, R. H. and Gietz, R. D., "High efficiency transformation of intact yeast cells using stranded nucleic acids as a carrier." *Curr. Genet.* 16:339–346 (1989).

Sherman et al., "Laboratory Course Manual for Methods in Yeast Genetics." (Cold Spring Harbor Laboratory Press, Cold Spring Harbor, N.Y. (1986)).

Silverman et al., "Meiotic recombination between yeast artificial chromosomes yields a single clone containing the entire BCL2 protooncogene." *Proc. Natl. Acad. Sci. USA* 87:9913–9917

What is claimed is:

1. A transgenic mouse whose genome comprises a fragment of human chromosome 14 from the five most proximal $V_H$ gene segments, continuing through the D segment genes, the J segment genes and the constant region genes through Cδ of the human immunoglobulin heavy chain locus, wherein said fragment does not contain a Cγ gene, and wherein said fragment is operably linked to a human Cγ gene selected from the group consisting of: a human Cγ1 gene, a human Cγ3 gene, and a human Cγ4 gene said transgenic mouse producing fully human antibodies having IgG1, IgG3, or IgG4 heavy chains, respectively, specific for a desired antigen when immunized with said desired antigen.

2. The transgenic mouse according to claim 1, wherein said mouse further comprises a fragment of human chromosome 2 comprising human $V_\kappa$, human $J_\kappa$ and human $C_\kappa$ gene segments of an immunoglobulin kappa light chain locus said transgenic mouse producing fully human antibodies having IgG1, IgG3, or IgG4 heavy chains, respectively, specific for a desired antigen when immunized with said desired antigen.

3. The transgenic mouse according to claim 2, wherein said fragment of human chromosome 2 extends from the three most proximal $V_\kappa$ gene segments, continuing through the $J_\kappa$ and $C_\kappa$ gene segments, through the human kappa deleting element.

4. The transgenic mouse according to any one of claims 1–3, wherein said mouse further comprises:

a) inactivated endogenous immunoglobulin heavy chain loci in which all of the J segment genes are deleted to prevent rearrangement and to prevent formation of a transcript of a rearranged locus and the expression of an endogenous immunoglobulin heavy chain; and b) inactivated endogenous immunoglobulin light chain loci in which the $C_\kappa$ gene is deleted to prevent rearrangement and to prevent formation of a transcript of a rearranged locus and the expression of an endogenous immunoglobulin light chain;

wherein said transgenic mouse lacks expression of endogenous immunoglobulin heavy and kappa light chains.

5. A method for producing a fully human IgG antibody specific for a desired antigen, comprising:

(a) immunizing a transgenic mouse according to any one of claims 1–3 with said desired antigen; and (b) recovering the antibody.

6. A method for producing a fully human IgG antibody specific for a desired antigen, comprising:

(a) immunizing a transgenic mouse according to claim 4 with said desired antigen; and (b) recovering the antibody.

* * * * *

SEQUENCE LISTING

```
<160> NUMBER OF SEQ ID NOS: 79

<210> SEQ ID NO 1
<211> LENGTH: 20
<212> TYPE: PRT
<213> ORGANISM: Homo sapiens

<400> SEQUENCE: 1

Ala Ser Thr Lys Gly Pro Ser Val Phe Pro Leu Ala Pro Cys Ser Arg
 1               5                  10                  15

Ser Thr Ser Thr
            20

<210> SEQ ID NO 2
<211> LENGTH: 80
<212> TYPE: PRT
<213> ORGANISM: Homo sapiens

<400> SEQUENCE: 2

Leu Ser Leu Thr Cys Ala Val Tyr Gly Gly Ser Phe Ser Gly Tyr Tyr
 1               5                  10                  15

Trp Ser Trp Ile Arg Gln Pro Pro Gly Lys Gly Leu Glu Trp Ile Gly
            20                  25                  30

Glu Ile Asn His Ser Gly Ser Thr Asn Tyr Asn Pro Ser Leu Lys Ser
        35                  40                  45

Arg Val Thr Ile Ser Val Asp Thr Ser Lys Asn Gln Phe Ser Leu Lys
    50                  55                  60

Leu Ser Ser Val Thr Ala Ala Asp Thr Ala Val Tyr Tyr Cys Ala Arg
65                  70                  75                  80

<210> SEQ ID NO 3
<211> LENGTH: 119
<212> TYPE: PRT
<213> ORGANISM: Homo sapiens

<400> SEQUENCE: 3

Leu Ser Leu Thr Cys Ala Val Tyr Gly Gly Ser Phe Ser Gly Tyr Tyr
 1               5                  10                  15

Trp Ser Trp Ile Arg Gln Pro Pro Gly Lys Gly Leu Glu Trp Ile Gly
            20                  25                  30
```

-continued

Glu Ile Asn Gln Ser Gly Ser Thr Asn Tyr Asn Pro Ser Leu Lys Ser
            35                  40                  45

Arg Val Ile Ile Ser Ile Asp Thr Ser Lys Thr Gln Phe Ser Leu Lys
    50                  55                  60

Leu Ser Ser Val Thr Ala Ala Asp Thr Ala Val Tyr Tyr Cys Ala Arg
65                  70                  75                  80

Glu Thr Pro His Ala Phe Asp Ile Trp Gly Gln Gly Thr Met Val Thr
                85                  90                  95

Val Ser Ser Ala Ser Thr Lys Gly Pro Ser Val Phe Pro Leu Ala Pro
            100                 105                 110

Cys Ser Arg Ser Thr Ser Thr
            115

<210> SEQ ID NO 4
<211> LENGTH: 120
<212> TYPE: PRT
<213> ORGANISM: Homo sapiens

<400> SEQUENCE: 4

Leu Ser Leu Thr Cys Ala Val Tyr Gly Gly Ser Phe Ser Gly Tyr Tyr
1               5                   10                  15

Trp Thr Trp Ile Arg Gln Pro Pro Gly Lys Gly Leu Glu Trp Ile Gly
            20                  25                  30

Glu Ile Ile His His Gly Asn Thr Asn Tyr Asn Pro Ser Leu Lys Ser
            35                  40                  45

Arg Val Ser Ile Ser Val Asp Thr Ser Thr Asn Gln Phe Ser Leu Thr
    50                  55                  60

Leu Ser Ser Val Thr Ala Ala Asp Thr Ala Val Tyr Tyr Cys Ala Arg
65                  70                  75                  80

Gly Gly Ala Val Ala Ala Phe Asp Tyr Trp Gly Gln Gly Thr Leu Val
                85                  90                  95

Thr Val Ser Ser Ala Ser Thr Lys Gly Pro Ser Val Phe Pro Leu Ala
            100                 105                 110

Pro Cys Ser Arg Ser Thr Ser Thr
            115                 120

<210> SEQ ID NO 5
<211> LENGTH: 82
<212> TYPE: PRT
<213> ORGANISM: Homo sapiens

<400> SEQUENCE: 5

Ser Leu Lys Ile Ser Cys Lys Gly Ser Gly Tyr Ser Phe Thr Ser Tyr
1               5                   10                  15

Trp Ile Gly Trp Val Arg Gln Met Pro Gly Lys Gly Leu Glu Trp Met
            20                  25                  30

Gly Ile Ile Tyr Pro Gly Asp Ser Asp Thr Arg Tyr Ser Pro Ser Phe
            35                  40                  45

Gln Gly Gln Val Thr Ile Ser Ala Asp Lys Ser Ile Ser Thr Ala Tyr
    50                  55                  60

Leu Gln Trp Ser Ser Leu Lys Ala Ser Asp Thr Ala Met Tyr Tyr Cys
65                  70                  75                  80

Ala Arg

<210> SEQ ID NO 6
<211> LENGTH: 121
<212> TYPE: PRT

-continued

<213> ORGANISM: Homo sapiens

<400> SEQUENCE: 6

Ser Leu Lys Ile Ser Cys Lys Gly Ser Gly Tyr Ser Phe Thr Ser Tyr
1               5                   10                  15

Trp Ile Gly Trp Val Arg Gln Met Pro Gly Lys Gly Leu Glu Trp Met
            20                  25                  30

Gly Ile Ile Tyr Pro Gly Asp Ser Asp Thr Arg Tyr Ser Pro Ser Phe
        35                  40                  45

Gln Gly Gln Val Thr Ile Ser Ala Asp Lys Ser Ile Ser Thr Ala Tyr
    50                  55                  60

Leu Gln Trp Ser Ser Leu Lys Ala Ser Asp Thr Ala Met Tyr Tyr Cys
65                  70                  75                  80

Ala Arg Gln Asp Gly Asp Ser Phe Asp Tyr Trp Gly Gln Gly Thr Leu
                85                  90                  95

Val Thr Val Ser Ser Ala Ser Thr Lys Gly Pro Ser Val Phe Pro Leu
            100                 105                 110

Ala Pro Cys Ser Arg Ser Thr Ser Thr
        115                 120

<210> SEQ ID NO 7
<211> LENGTH: 83
<212> TYPE: PRT
<213> ORGANISM: Homo sapiens
<220> FEATURE:
<221> NAME/KEY: MOD_RES
<222> LOCATION: (22)
<223> OTHER INFORMATION: Variable amino acid

<400> SEQUENCE: 7

Arg Ser Leu Arg Leu Ser Cys Ala Ala Ser Gly Phe Thr Phe Ser Ser
1               5                   10                  15

Tyr Gly Met His Trp Xaa Arg Gln Ala Pro Gly Lys Gly Leu Glu Trp
            20                  25                  30

Val Ala Val Ile Ser Tyr Asp Gly Ser Asn Lys Tyr Tyr Ala Asp Ser
        35                  40                  45

Val Lys Gly Arg Phe Thr Ile Ser Arg Asp Asn Ser Lys Asn Thr Leu
    50                  55                  60

Tyr Leu Gln Met Asn Ser Leu Arg Ala Glu Asp Thr Ala Val Tyr Tyr
65                  70                  75                  80

Cys Ala Arg

<210> SEQ ID NO 8
<211> LENGTH: 122
<212> TYPE: PRT
<213> ORGANISM: Homo sapiens
<220> FEATURE:
<221> NAME/KEY: MOD_RES
<222> LOCATION: (22)
<223> OTHER INFORMATION: Variable amino acid

<400> SEQUENCE: 8

Arg Ser Leu Arg Leu Ser Cys Ala Ala Ser Gly Phe Thr Phe Ser Ser
1               5                   10                  15

Tyr Gly Met His Trp Xaa Arg Gln Ala Pro Gly Lys Gly Leu Glu Trp
            20                  25                  30

Val Ala Glu Ile Ser Tyr Asp Gly Ser Asn Lys Tyr Tyr Val Asp Ser
        35                  40                  45

Val Lys Gly Arg Leu Thr Ile Ser Arg Asp Asn Ser Lys Asn Thr Leu

```
                 50                  55                  60
Tyr Leu Gln Met Asn Ser Leu Arg Ala Glu Asp Thr Ala Val Tyr Tyr
 65                  70                  75                  80

Cys Ala Arg Asp Arg Leu Gly Ile Phe Asp Tyr Trp Gly Gln Gly Thr
                 85                  90                  95

Leu Val Thr Val Ser Ser Ala Ser Thr Lys Gly Pro Ser Val Phe Pro
            100                 105                 110

Leu Ala Pro Cys Ser Arg Ser Thr Ser Thr
            115                 120
```

<210> SEQ ID NO 9
<211> LENGTH: 17
<212> TYPE: PRT
<213> ORGANISM: Homo sapiens

<400> SEQUENCE: 9

```
Arg Thr Val Ala Ala Pro Ser Val Phe Ile Phe Pro Pro Ser Asp Glu
  1               5                  10                  15

Gln
```

<210> SEQ ID NO 10
<211> LENGTH: 76
<212> TYPE: PRT
<213> ORGANISM: Homo sapiens

<400> SEQUENCE: 10

```
Thr Ile Thr Cys Gln Ala Ser Gln Asp Ile Ser Asn Tyr Leu Asn Trp
  1               5                  10                  15

Tyr Gln Gln Lys Pro Gly Lys Ala Pro Lys Leu Leu Ile Tyr Asp Ala
                 20                  25                  30

Ser Asn Leu Glu Thr Gly Val Pro Ser Arg Phe Ser Gly Ser Gly Ser
             35                  40                  45

Gly Asp Thr Asp Phe Thr Phe Thr Ile Ser Ser Leu Gln Pro Glu Asp
 50                  55                  60

Ile Ala Thr Tyr Tyr Cys Gln Gln Asp Asn Leu Pro
 65                  70                  75
```

<210> SEQ ID NO 11
<211> LENGTH: 105
<212> TYPE: PRT
<213> ORGANISM: Homo sapiens

<400> SEQUENCE: 11

```
Thr Ile Thr Cys Gln Ala Ser Gln Asp Ile Lys Phe Tyr Leu Ser Trp
  1               5                  10                  15

Phe Gln Gln Lys Pro Gly Lys Ala Pro Lys Leu Leu Ile Tyr Gly Thr
                 20                  25                  30

Ser Tyr Leu Glu Thr Gly Val Pro Ser Ser Phe Ser Gly Ser Gly Ser
             35                  40                  45

Gly Asp Thr Asp Phe Thr Leu Thr Ile Ser Ser Leu Gln Pro Glu Asp
 50                  55                  60

Val Ala Thr Tyr Phe Cys Gln Gln Asp Asp Leu Pro Tyr Thr Phe Gly
 65                  70                  75                  80

Pro Gly Thr Lys Val Asp Ile Lys Arg Thr Val Ala Ala Pro Ser Val
                 85                  90                  95

Phe Ile Phe Pro Pro Ser Asp Glu Gln
            100                 105
```

<210> SEQ ID NO 12
<211> LENGTH: 105
<212> TYPE: PRT
<213> ORGANISM: Homo sapiens

<400> SEQUENCE: 12

Thr Ile Thr Cys Gln Ala Ser Gln Asp Ile Ser Asn Tyr Leu Asn Trp
1               5                   10                  15

Tyr Gln Gln Lys Ala Gly Lys Ala Pro Lys Val Leu Ile Tyr Ala Ala
            20                  25                  30

Ser Asn Leu Glu Ala Gly Val Pro Ser Arg Phe Ser Gly Ser Gly Ser
        35                  40                  45

Gly Asp Thr Asp Phe Thr Phe Thr Ile Ser Ser Leu Gln Pro Glu Asp
    50                  55                  60

Ile Ala Thr Tyr Tyr Cys Gln His Asp Asn Leu Pro Leu Thr Phe Gly
65                  70                  75                  80

Gly Gly Thr Lys Val Glu Ile Lys Arg Thr Val Ala Ala Pro Ser Val
                85                  90                  95

Phe Ile Phe Pro Pro Ser Asp Glu Gln
            100                 105

<210> SEQ ID NO 13
<211> LENGTH: 73
<212> TYPE: PRT
<213> ORGANISM: Homo sapiens

<400> SEQUENCE: 13

Thr Cys Arg Ala Ser Gln Ser Ile Ser Ser Tyr Leu Asn Trp Tyr Gln
1               5                   10                  15

Gln Lys Pro Gly Lys Ala Pro Lys Leu Leu Ile Tyr Ala Ala Ser Ser
            20                  25                  30

Leu Gln Ser Gly Val Pro Ser Arg Phe Ser Gly Ser Ser Gly Thr Asp
        35                  40                  45

Phe Thr Leu Thr Ile Ser Ser Leu Gln Pro Glu Asp Phe Ala Thr Tyr
    50                  55                  60

Tyr Cys Gln Gln Ser Tyr Ser Thr Pro
65                  70

<210> SEQ ID NO 14
<211> LENGTH: 102
<212> TYPE: PRT
<213> ORGANISM: Homo sapiens
<220> FEATURE:
<221> NAME/KEY: MOD_RES
<222> LOCATION: (81)
<223> OTHER INFORMATION: Variable amino acid

<400> SEQUENCE: 14

Thr Cys Arg Ala Ser Gln Ser Ile Ser Asn Tyr Leu Asn Trp Tyr Gln
1               5                   10                  15

Gln Lys Pro Gly Lys Ala Pro Lys Phe Leu Ile Tyr Gly Ala Ser Ser
            20                  25                  30

Leu Glu Ser Gly Val Pro Ser Arg Phe Ser Gly Ser Ser Gly Thr Asp
        35                  40                  45

Phe Thr Leu Thr Ile Ser Ser Leu Gln Pro Glu Asp Phe Ala Thr Tyr
    50                  55                  60

Tyr Cys Gln Gln Ser Tyr Ser Asn Pro Leu Thr Phe Gly Gly Gly Thr
65                  70                  75                  80

```
Xaa Val Glu Ile Lys Arg Thr Val Ala Ala Pro Ser Val Phe Ile Phe
             85                  90                  95

Pro Pro Ser Asp Glu Gln
            100
```

<210> SEQ ID NO 15
<211> LENGTH: 82
<212> TYPE: PRT
<213> ORGANISM: Homo sapiens

<400> SEQUENCE: 15

```
Thr Ile Asn Cys Lys Ser Ser Gln Ser Val Leu Tyr Ser Ser Asn Asn
 1               5                  10                  15

Lys Asn Tyr Leu Ala Trp Tyr Gln Gln Lys Pro Gly Gln Pro Pro Lys
            20                  25                  30

Leu Leu Ile Tyr Trp Ala Ser Thr Arg Glu Ser Gly Val Pro Asp Arg
        35                  40                  45

Phe Ser Gly Ser Gly Ser Gly Thr Asp Phe Thr Leu Thr Ile Ser Ser
    50                  55                  60

Leu Gln Ala Glu Asp Val Ala Val Tyr Tyr Cys Gln Gln Tyr Tyr Ser
65                  70                  75                  80

Thr Pro
```

<210> SEQ ID NO 16
<211> LENGTH: 111
<212> TYPE: PRT
<213> ORGANISM: Homo sapiens

<400> SEQUENCE: 16

```
Thr Ile Asn Cys Lys Ser Ser Gln Ser Val Leu Tyr Ile Ser Asn Asn
 1               5                  10                  15

Lys Asn Tyr Leu Ala Trp Tyr Gln Gln Lys Pro Gly Gln Ser Pro Lys
            20                  25                  30

Leu Leu Ile Tyr Trp Ala Ser Thr Arg Lys Ser Gly Val Pro Asp Arg
        35                  40                  45

Phe Ser Gly Ser Gly Ser Gly Thr Asp Phe Thr Leu Thr Ile Ser Ser
    50                  55                  60

Leu Gln Ala Glu Asp Val Ala Val Tyr Tyr Cys Gln Gln Tyr Tyr Asp
65                  70                  75                  80

Thr Pro Phe Thr Phe Gly Pro Gly Thr Lys Val Asp Ile Lys Arg Thr
            85                  90                  95

Val Ala Ala Pro Ser Val Phe Ile Phe Pro Pro Ser Asp Glu Gln
            100                 105                 110
```

<210> SEQ ID NO 17
<211> LENGTH: 20
<212> TYPE: PRT
<213> ORGANISM: Homo sapiens

<400> SEQUENCE: 17

```
Ala Ser Thr Lys Gly Pro Ser Val Phe Pro Leu Ala Pro Cys Ser Arg
 1               5                  10                  15

Ser Thr Ser Thr
            20
```

<210> SEQ ID NO 18
<211> LENGTH: 76
<212> TYPE: PRT
<213> ORGANISM: Homo sapiens

```
<400> SEQUENCE: 18

Val Ser Gly Gly Ser Ile Ser Ser Gly Gly Tyr Tyr Trp Ser Trp Ile
  1               5                  10                  15

Arg Gln His Pro Gly Lys Gly Leu Glu Trp Ile Gly Tyr Ile Tyr Tyr
             20                  25                  30

Ser Gly Ser Thr Tyr Tyr Asn Pro Ser Leu Lys Ser Arg Val Thr Ile
         35                  40                  45

Ser Val Asp Thr Ser Lys Asn Gln Phe Ser Leu Lys Leu Ser Ser Val
     50                  55                  60

Thr Ala Ala Asp Thr Ala Val Tyr Tyr Cys Ala Arg
 65                  70                  75

<210> SEQ ID NO 19
<211> LENGTH: 118
<212> TYPE: PRT
<213> ORGANISM: Homo sapiens

<400> SEQUENCE: 19

Val Ser Gly Gly Ser Ile Asn Ser Gly Asp Tyr Tyr Trp Ser Trp Ile
  1               5                  10                  15

Arg Gln His Pro Gly Lys Gly Leu Asp Cys Ile Gly Tyr Ile Tyr Tyr
             20                  25                  30

Ser Gly Ser Thr Tyr Tyr Asn Pro Phe Leu Lys Thr Arg Val Thr Ile
         35                  40                  45

Ser Val Asp Thr Ser Lys Asn Gln Phe Ser Leu Lys Leu Ser Ser Val
     50                  55                  60

Thr Ala Ala Asp Thr Ala Val Tyr Tyr Cys Ala Arg Ser Thr Val Val
 65                  70                  75                  80

Asn Pro Gly Trp Phe Asp Pro Trp Gly Gln Gly Tyr Leu Val Thr Val
                 85                  90                  95

Ser Ser Ala Ser Thr Lys Gly Pro Ser Val Phe Pro Leu Ala Pro Cys
            100                 105                 110

Ser Arg Ser Thr Ser Thr
            115

<210> SEQ ID NO 20
<211> LENGTH: 117
<212> TYPE: PRT
<213> ORGANISM: Homo sapiens

<400> SEQUENCE: 20

Val Ser Gly Gly Ser Ile Asn Ser Gly Asp Tyr Tyr Trp Ser Trp Ile
  1               5                  10                  15

Arg Gln His Pro Gly Lys Gly Leu Glu Trp Ile Gly Ser Ile Tyr Tyr
             20                  25                  30

Ser Gly Asn Thr Tyr Phe Asn Pro Ser Leu Lys Ser Arg Val Thr Ile
         35                  40                  45

Ser Leu Asp Thr Ser Lys Asn Gln Phe Ser Leu Lys Leu Ser Ser Val
     50                  55                  60

Thr Ala Ala Asp Thr Ala Val Cys Tyr Cys Ala Arg Asn Ile Val Thr
 65                  70                  75                  80

Thr Gly Ala Phe Asp Ile Trp Gly Gln Gly Thr Met Val Thr Val Ser
                 85                  90                  95

Ser Ala Ser Thr Lys Gly Pro Ser Val Phe Pro Leu Ala Pro Cys Ser
            100                 105                 110
```

```
Arg Ser Thr Ser Thr
        115

<210> SEQ ID NO 21
<211> LENGTH: 116
<212> TYPE: PRT
<213> ORGANISM: Homo sapiens

<400> SEQUENCE: 21

Val Ser Gly Gly Ser Ile Ser Ser Gly Asp Tyr Tyr Trp Thr Trp Ile
 1               5                  10                  15

Arg Gln His Pro Gly Lys Gly Leu Glu Trp Ile Gly Tyr Ile Tyr Tyr
            20                  25                  30

Ser Gly Asn Thr Tyr Tyr Asn Pro Ser Leu Lys Ser Arg Val Ser Met
        35                  40                  45

Ser Ile Asp Thr Ser Glu Asn Gln Phe Ser Leu Lys Leu Ser Ser Val
    50                  55                  60

Thr Ala Ala Asp Thr Ala Val Tyr Tyr Cys Ala Arg Lys Pro Val Thr
65                  70                  75                  80

Gly Gly Glu Asp Tyr Trp Gly Gln Gly Thr Leu Val Thr Val Ser Ser
                85                  90                  95

Ala Ser Thr Lys Gly Pro Ser Val Phe Pro Leu Ala Pro Cys Ser Arg
            100                 105                 110

Ser Thr Ser Thr
        115

<210> SEQ ID NO 22
<211> LENGTH: 76
<212> TYPE: PRT
<213> ORGANISM: Homo sapiens

<400> SEQUENCE: 22

Val Ser Gly Gly Ser Val Ser Ser Gly Ser Tyr Tyr Trp Ser Trp Ile
 1               5                  10                  15

Arg Gln Pro Pro Gly Lys Gly Leu Glu Trp Ile Gly Tyr Ile Tyr Tyr
            20                  25                  30

Ser Gly Ser Thr Asn Tyr Asn Pro Ser Leu Lys Ser Arg Val Thr Ile
        35                  40                  45

Ser Val Asp Thr Ser Lys Asn Gln Phe Ser Leu Lys Leu Ser Ser Val
    50                  55                  60

Thr Ala Ala Asp Thr Ala Val Tyr Tyr Cys Ala Arg
65                  70                  75

<210> SEQ ID NO 23
<211> LENGTH: 117
<212> TYPE: PRT
<213> ORGANISM: Homo sapiens

<400> SEQUENCE: 23

Val Ser Gly Gly Ser Val Ser Ser Gly Asp Tyr Tyr Trp Ser Trp Ile
 1               5                  10                  15

Arg Gln Pro Pro Gly Lys Gly Leu Glu Trp Ile Gly His Leu Tyr Tyr
            20                  25                  30

Ser Gly Asn Thr Asn Tyr Asn Pro Ser Leu Lys Ser Arg Val Thr Ile
        35                  40                  45

Ser Leu Asp Thr Ser Lys Asn Gln Phe Ser Leu Lys Leu Ser Ser Val
    50                  55                  60

Thr Ala Ala Asp Thr Ala Val Tyr Tyr Cys Ala Arg Asp Phe Leu Thr
```

-continued

```
                65                  70                  75                  80
Gly Ser Phe Phe Asp Tyr Trp Gly Gln Gly Thr Leu Val Thr Val Ser
                        85                  90                  95
Ser Ala Ser Thr Lys Gly Pro Ser Val Phe Pro Leu Ala Pro Cys Ser
                100                 105                 110
Arg Ser Thr Ser Thr
        115

<210> SEQ ID NO 24
<211> LENGTH: 17
<212> TYPE: PRT
<213> ORGANISM: Homo sapiens

<400> SEQUENCE: 24

Arg Thr Val Ala Ala Pro Ser Val Phe Ile Phe Pro Pro Ser Asp Glu
  1               5                   10                  15
Gln

<210> SEQ ID NO 25
<211> LENGTH: 75
<212> TYPE: PRT
<213> ORGANISM: Homo sapiens

<400> SEQUENCE: 25

Thr Ile Thr Cys Gln Ala Ser Gln Asp Ile Ser Asn Tyr Leu Asn Trp
  1               5                   10                  15
Tyr Gln Gln Lys Pro Gly Lys Ala Pro Lys Leu Leu Ile Tyr Asp Ala
            20                  25                  30
Ser Asn Leu Glu Thr Gly Val Pro Ser Arg Phe Ser Gly Ser Gly Ser
        35                  40                  45
Gly Thr Asp Phe Thr Phe Thr Ile Ser Ser Leu Gln Pro Glu Asp Ile
    50                  55                  60
Ala Thr Tyr Tyr Cys Gln Gln Asp Asn Leu Pro
 65                  70                  75

<210> SEQ ID NO 26
<211> LENGTH: 103
<212> TYPE: PRT
<213> ORGANISM: Homo sapiens

<400> SEQUENCE: 26

Thr Ile Thr Cys Gln Ala Ser Gln Asp Ile Asn Asn Tyr Leu Asn Trp
  1               5                   10                  15
Phe Gln Gln Lys Pro Gly Lys Ala Pro Lys Val Leu Ile His Asp Ala
            20                  25                  30
Ser Asn Leu Glu Thr Gly Gly Pro Ser Arg Phe Ser Gly Ser Gly Ser
        35                  40                  45
Gly Thr Asp Phe Thr Phe Thr Ile Ser Gly Leu Gln Pro Glu Asp Ile
    50                  55                  60
Ala Thr Tyr Tyr Cys Gln Gln Glu Ser Leu Pro Leu Thr Phe Gly Gly
 65                  70                  75                  80
Gly Thr Lys Glu Ile Lys Arg Thr Val Ala Ala Pro Ser Val Phe Ile
                85                  90                  95
Phe Pro Pro Ser Asp Glu Gln
            100

<210> SEQ ID NO 27
<211> LENGTH: 104
```

```
<212> TYPE: PRT
<213> ORGANISM: Homo sapiens

<400> SEQUENCE: 27

Thr Ile Thr Cys Gln Ala Ser Gln Asp Ile Thr Ile Tyr Leu Asn Trp
 1               5                  10                  15

Tyr Gln Gln Lys Pro Gly Lys Ala Pro Lys Leu Leu Ile Asn Asp Ala
             20                  25                  30

Ser Ser Leu Glu Thr Gly Val Pro Leu Arg Phe Ser Gly Ser Gly Ser
         35                  40                  45

Gly Thr Asp Phe Thr Phe Thr Ile Ser Ser Leu Gln Pro Glu Asp Ile
     50                  55                  60

Ala Thr Tyr Tyr Cys Gln Gln Asp Asn His Pro Leu Thr Phe Gly Gly
 65                  70                  75                  80

Gly Thr Lys Val Ala Ile Lys Arg Thr Val Ala Ala Pro Ser Val Phe
                 85                  90                  95

Ile Phe Pro Pro Ser Asp Glu Gln
             100

<210> SEQ ID NO 28
<211> LENGTH: 104
<212> TYPE: PRT
<213> ORGANISM: Homo sapiens

<400> SEQUENCE: 28

Thr Ile Thr Cys Gln Ala Ser Gln Asp Ile Ser Asn Tyr Leu Asn Trp
 1               5                  10                  15

Tyr Gln Gln Lys Pro Gly Lys Ala Pro Lys Leu Leu Ile Tyr Asp Ala
             20                  25                  30

Ser Asn Leu Glu Thr Gly Val Pro Ser Arg Phe Ser Gly Ser Gly Ser
         35                  40                  45

Gly Thr Asp Phe Thr Phe Thr Ile Ser Ser Leu Gln Pro Glu Asp Val
     50                  55                  60

Gly Thr Tyr Val Cys Gln Gln Glu Ser Leu Pro Cys Gly Phe Gly Gln
 65                  70                  75                  80

Gly Thr Lys Leu Glu Ile Lys Arg Thr Val Ala Ala Pro Ser Val Phe
                 85                  90                  95

Ile Phe Pro Pro Ser Asp Glu Gln
             100

<210> SEQ ID NO 29
<211> LENGTH: 104
<212> TYPE: PRT
<213> ORGANISM: Homo sapiens

<400> SEQUENCE: 29

Thr Ile Thr Cys Gln Ala Ser Gln Asp Ile Ser Asn Tyr Leu Asn Trp
 1               5                  10                  15

Tyr Gln Gln Lys Pro Gly Lys Ala Pro Lys Leu Leu Ile Asn Asp Ala
             20                  25                  30

Ser Asp Leu Glu Thr Gly Ile Pro Ser Arg Phe Ser Gly Ser Gly Ser
         35                  40                  45

Gly Thr Asp Phe Thr Phe Thr Ile Ser Asn Leu Gln Pro Glu Asp Ile
     50                  55                  60

Ala Thr Tyr Tyr Cys Gln Gln Asp Asn Ser Pro Leu Thr Phe Gly Gly
 65                  70                  75                  80

Gly Thr Lys Val Glu Ile Arg Arg Thr Val Ala Ala Pro Ser Val Phe
```

-continued

```
                85                  90                  95
Ile Phe Pro Pro Ser Asp Glu Gln
            100

<210> SEQ ID NO 30
<211> LENGTH: 15
<212> TYPE: DNA
<213> ORGANISM: Homo sapiens

<400> SEQUENCE: 30
ttactgtgcg agaca                                                     15

<210> SEQ ID NO 31
<211> LENGTH: 15
<212> TYPE: DNA
<213> ORGANISM: Homo sapiens

<400> SEQUENCE: 31
ttactgtgcg agaga                                                     15

<210> SEQ ID NO 32
<211> LENGTH: 15
<212> TYPE: DNA
<213> ORGANISM: Homo sapiens

<400> SEQUENCE: 32
ttactgtacc acaga                                                     15

<210> SEQ ID NO 33
<211> LENGTH: 15
<212> TYPE: DNA
<213> ORGANISM: Homo sapiens

<400> SEQUENCE: 33
ttactgtgcg agaga                                                     15

<210> SEQ ID NO 34
<211> LENGTH: 14
<212> TYPE: DNA
<213> ORGANISM: Homo sapiens

<400> SEQUENCE: 34
ttactgtgcg agag                                                      14

<210> SEQ ID NO 35
<211> LENGTH: 15
<212> TYPE: DNA
<213> ORGANISM: Homo sapiens

<400> SEQUENCE: 35
ttactgtgcg agaga                                                     15

<210> SEQ ID NO 36
<211> LENGTH: 15
<212> TYPE: DNA
<213> ORGANISM: Homo sapiens

<400> SEQUENCE: 36
ttactgtgcg agaga                                                     15

<210> SEQ ID NO 37
<211> LENGTH: 15
<212> TYPE: DNA
```

```
<213> ORGANISM: Homo sapiens

<400> SEQUENCE: 37
ttactgtgcg agaga                                                    15

<210> SEQ ID NO 38
<211> LENGTH: 12
<212> TYPE: DNA
<213> ORGANISM: Homo sapiens

<400> SEQUENCE: 38
attactgtgc ga                                                       12

<210> SEQ ID NO 39
<211> LENGTH: 14
<212> TYPE: DNA
<213> ORGANISM: Homo sapiens

<400> SEQUENCE: 39
tattactgtg cgag                                                     14

<210> SEQ ID NO 40
<211> LENGTH: 12
<212> TYPE: DNA
<213> ORGANISM: Homo sapiens

<400> SEQUENCE: 40
tattactgtg cg                                                       12

<210> SEQ ID NO 41
<211> LENGTH: 15
<212> TYPE: DNA
<213> ORGANISM: Homo sapiens

<400> SEQUENCE: 41
ttactgtgcg agaca                                                    15

<210> SEQ ID NO 42
<211> LENGTH: 10
<212> TYPE: DNA
<213> ORGANISM: Homo sapiens

<400> SEQUENCE: 42
taggagtgtt                                                          10

<210> SEQ ID NO 43
<211> LENGTH: 17
<212> TYPE: DNA
<213> ORGANISM: Homo sapiens

<400> SEQUENCE: 43
gtagtaccag ctgctat                                                  17

<210> SEQ ID NO 44
<211> LENGTH: 10
<212> TYPE: DNA
<213> ORGANISM: Homo sapiens

<400> SEQUENCE: 44
gcagcagctg                                                          10

<210> SEQ ID NO 45
<211> LENGTH: 15
```

```
<212> TYPE: DNA
<213> ORGANISM: Homo sapiens

<400> SEQUENCE: 45
gatattttga ctggt                                                15

<210> SEQ ID NO 46
<211> LENGTH: 16
<212> TYPE: DNA
<213> ORGANISM: Homo sapiens

<400> SEQUENCE: 46
tatagcagtg gctggt                                               16

<210> SEQ ID NO 47
<211> LENGTH: 14
<212> TYPE: DNA
<213> ORGANISM: Homo sapiens

<400> SEQUENCE: 47
ggatatagta gtgg                                                 14

<210> SEQ ID NO 48
<211> LENGTH: 12
<212> TYPE: DNA
<213> ORGANISM: Homo sapiens

<400> SEQUENCE: 48
gggagctacg gg                                                   12

<210> SEQ ID NO 49
<211> LENGTH: 11
<212> TYPE: DNA
<213> ORGANISM: Homo sapiens

<400> SEQUENCE: 49
actaactacc c                                                    11

<210> SEQ ID NO 50
<211> LENGTH: 12
<212> TYPE: DNA
<213> ORGANISM: Homo sapiens

<400> SEQUENCE: 50
gactactggg gc                                                   12

<210> SEQ ID NO 51
<211> LENGTH: 16
<212> TYPE: DNA
<213> ORGANISM: Homo sapiens

<400> SEQUENCE: 51
ctttgactac tggggc                                               16

<210> SEQ ID NO 52
<211> LENGTH: 16
<212> TYPE: DNA
<213> ORGANISM: Homo sapiens

<400> SEQUENCE: 52
ctactactac tacggt                                               16

<210> SEQ ID NO 53
```

-continued

```
<211> LENGTH: 17
<212> TYPE: DNA
<213> ORGANISM: Homo sapiens

<400> SEQUENCE: 53
actactacta ctacggt                                                  17

<210> SEQ ID NO 54
<211> LENGTH: 16
<212> TYPE: DNA
<213> ORGANISM: Homo sapiens

<400> SEQUENCE: 54
ctttgactac tggggc                                                   16

<210> SEQ ID NO 55
<211> LENGTH: 16
<212> TYPE: DNA
<213> ORGANISM: Homo sapiens

<400> SEQUENCE: 55
ctactactac tacggt                                                   16

<210> SEQ ID NO 56
<211> LENGTH: 15
<212> TYPE: DNA
<213> ORGANISM: Homo sapiens

<400> SEQUENCE: 56
tttgactact ggggc                                                    15

<210> SEQ ID NO 57
<211> LENGTH: 18
<212> TYPE: DNA
<213> ORGANISM: Homo sapiens

<400> SEQUENCE: 57
tactactact actacggt                                                 18

<210> SEQ ID NO 58
<211> LENGTH: 16
<212> TYPE: DNA
<213> ORGANISM: Homo sapiens

<400> SEQUENCE: 58
ctttgactac tggggc                                                   16

<210> SEQ ID NO 59
<211> LENGTH: 12
<212> TYPE: DNA
<213> ORGANISM: Homo sapiens

<400> SEQUENCE: 59
gactactggg gc                                                       12

<210> SEQ ID NO 60
<211> LENGTH: 16
<212> TYPE: DNA
<213> ORGANISM: Homo sapiens

<400> SEQUENCE: 60
ctttgactac tggggc                                                   16
```

```
<210> SEQ ID NO 61
<211> LENGTH: 18
<212> TYPE: DNA
<213> ORGANISM: Homo sapiens

<400> SEQUENCE: 61
atgctttgat atctgggg                                                 18

<210> SEQ ID NO 62
<211> LENGTH: 18
<212> TYPE: DNA
<213> ORGANISM: Homo sapiens

<400> SEQUENCE: 62
ttaaacgaac agtacccc                                                 18

<210> SEQ ID NO 63
<211> LENGTH: 20
<212> TYPE: DNA
<213> ORGANISM: Homo sapiens

<400> SEQUENCE: 63
acaggctaac agtttccctc                                               20

<210> SEQ ID NO 64
<211> LENGTH: 17
<212> TYPE: DNA
<213> ORGANISM: Homo sapiens

<400> SEQUENCE: 64
aagtataaca gtgcccc                                                  17

<210> SEQ ID NO 65
<211> LENGTH: 18
<212> TYPE: DNA
<213> ORGANISM: Homo sapiens

<400> SEQUENCE: 65
acagtatgat aatctccc                                                 18

<210> SEQ ID NO 66
<211> LENGTH: 18
<212> TYPE: DNA
<213> ORGANISM: Homo sapiens

<400> SEQUENCE: 66
aaagtataat agttaccc                                                 18

<210> SEQ ID NO 67
<211> LENGTH: 17
<212> TYPE: DNA
<213> ORGANISM: Homo sapiens

<400> SEQUENCE: 67
cagcataata gttaccc                                                  17

<210> SEQ ID NO 68
<211> LENGTH: 16
<212> TYPE: DNA
<213> ORGANISM: Homo sapiens

<400> SEQUENCE: 68
aatattatag tactcc                                                   16
```

```
<210> SEQ ID NO 69
<211> LENGTH: 19
<212> TYPE: DNA
<213> ORGANISM: Homo sapiens

<400> SEQUENCE: 69
cagtatggta gctcacctc                                                 19

<210> SEQ ID NO 70
<211> LENGTH: 16
<212> TYPE: DNA
<213> ORGANISM: Homo sapiens

<400> SEQUENCE: 70
gatcaccttc ggccaa                                                    16

<210> SEQ ID NO 71
<211> LENGTH: 14
<212> TYPE: DNA
<213> ORGANISM: Homo sapiens

<400> SEQUENCE: 71
ggacgttcgg ccaa                                                      14

<210> SEQ ID NO 72
<211> LENGTH: 16
<212> TYPE: DNA
<213> ORGANISM: Homo sapiens

<400> SEQUENCE: 72
attcactttc ggccct                                                    16

<210> SEQ ID NO 73
<211> LENGTH: 16
<212> TYPE: DNA
<213> ORGANISM: Homo sapiens

<400> SEQUENCE: 73
gctcactttc ggcgga                                                    16

<210> SEQ ID NO 74
<211> LENGTH: 16
<212> TYPE: DNA
<213> ORGANISM: Homo sapiens

<400> SEQUENCE: 74
gatcaccttc ggccaa                                                    16

<210> SEQ ID NO 75
<211> LENGTH: 16
<212> TYPE: DNA
<213> ORGANISM: Homo sapiens

<400> SEQUENCE: 75
attcactttc ggccct                                                    16

<210> SEQ ID NO 76
<211> LENGTH: 16
<212> TYPE: DNA
<213> ORGANISM: Homo sapiens

<400> SEQUENCE: 76
gctcactttc ggcgga                                                    16
```

```
<210> SEQ ID NO 77
<211> LENGTH: 13
<212> TYPE: DNA
<213> ORGANISM: Homo sapiens

<400> SEQUENCE: 77
cacttttggc cag                                                          13

<210> SEQ ID NO 78
<211> LENGTH: 23
<212> TYPE: DNA
<213> ORGANISM: Artificial Sequence
<220> FEATURE:
<223> OTHER INFORMATION: Description of Artificial Sequence: Primer
<220> FEATURE:
<221> NAME/KEY: modified_base
<222> LOCATION: (21)
<223> OTHER INFORMATION: i

<400> SEQUENCE: 78
caggtgcagc tggagcagtc ngg                                               23

<210> SEQ ID NO 79
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 79
gctgagggag tagagtcctg agga                                              24
```